United States Patent
Ruiz

(10) Patent No.: US 9,078,792 B2
(45) Date of Patent: Jul. 14, 2015

(54) TWO-PIECE WEARABLE ABSORBENT ARTICLE HAVING ADVANTAGEOUS FRONT WAIST REGION AND LANDING ZONE CONFIGURATION

(75) Inventor: Oscar Antonio Ruiz, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 743 days.

(21) Appl. No.: 13/275,365

(22) Filed: Oct. 18, 2011

(65) Prior Publication Data

US 2013/0006209 A1 Jan. 3, 2013

Related U.S. Application Data

(60) Provisional application No. 61/503,189, filed on Jun. 30, 2011, provisional application No. 61/503,215, filed on Jun. 30, 2011.

(51) Int. Cl.
| | | |
|---|---|---|
| *A61F 13/15* | (2006.01) | |
| *A61F 13/20* | (2006.01) | |
| *A61F 13/505* | (2006.01) | |
| *A61F 13/49* | (2006.01) | |
| *A61F 13/68* | (2006.01) | |
| *A61F 13/74* | (2006.01) | |

(52) U.S. Cl.
CPC ......... *A61F 13/505* (2013.01); *A61F 13/15203* (2013.01); *A61F 13/49004* (2013.01); *A61F 13/68* (2013.01); *A61F 13/74* (2013.01); *A61F 13/15268* (2013.01); *A61F 2013/15276* (2013.01); *A61F 2013/15357* (2013.01); *A61F 2013/5055* (2013.01)

(58) Field of Classification Search
CPC ............ A61F 13/505; A61F 13/49004; A61F 13/15268; A61F 13/15756; A61F 13/539; A61F 13/4906; A61F 13/56; A61F 13/5611; A61F 13/66; A61F 13/74; A61F 13/82; A61F 13/49061; A61F 2013/505; A44B 18/00
USPC .................. 604/386–387, 390–391, 397–398
See application file for complete search history.

(56) References Cited

U.S. PATENT DOCUMENTS

| | | | |
|---|---|---|---|
| 2,119,610 A | 6/1938 | Robert | |
| 2,530,647 A | 11/1950 | Buchler | |

(Continued)

FOREIGN PATENT DOCUMENTS

| | | |
|---|---|---|
| AU | 642 386 | 10/1993 |
| CA | 2 103 537 | 2/1995 |

(Continued)

OTHER PUBLICATIONS www.gdiapers.com—Web pages dated Nov. 23, 2009.

(Continued)

*Primary Examiner* — Michele M Kidwell
(74) *Attorney, Agent, or Firm* — Christian M. Best; William E. Gallagher

(57) ABSTRACT

A two-piece wearer absorbent article having an outer cover and an absorbent insert is disclosed. The outer cover has a landing zone comprising a loops material disposed on the front waist region, and extending laterally across substantially all of the front waist region. The inner surface of the outer cover has an insert fastener component disposed in the front region thereof, and the insert fastener component is secured directly to the loops material.

12 Claims, 35 Drawing Sheets

(56) References Cited

U.S. PATENT DOCUMENTS

| | | |
|---|---|---|
| 2,688,328 A | 9/1954 | Marcus |
| 2,793,642 A | 5/1957 | Andruhovici |
| 3,050,063 A * | 8/1962 | Margraf .................. 604/399 |
| 3,077,193 A | 2/1963 | Mann |
| 3,496,259 A | 2/1970 | Guenther |
| 3,560,292 A | 2/1971 | Butter |
| 3,719,736 A | 3/1973 | Woodruff |
| 3,735,424 A | 5/1973 | Maggio et al. |
| 3,860,003 A | 1/1975 | Buell |
| 3,911,173 A | 10/1975 | Sprague, Jr. |
| 3,926,189 A | 12/1975 | Taylor |
| 3,929,135 A | 12/1975 | Thompson |
| 3,955,575 A | 5/1976 | Okuda |
| 4,022,210 A | 5/1977 | Glassman |
| 4,072,150 A | 2/1978 | Glassman |
| 4,081,301 A | 3/1978 | Buell |
| 4,116,892 A | 9/1978 | Schwarz |
| 4,195,634 A | 4/1980 | DiSalvo et al. |
| 4,223,059 A | 9/1980 | Schwarz |
| 4,265,245 A | 5/1981 | Glassman |
| 4,284,454 A | 8/1981 | Joa |
| 4,324,246 A | 4/1982 | Mullane et al. |
| 4,326,302 A | 4/1982 | Lowe et al. |
| 4,338,939 A | 7/1982 | Daville |
| 4,342,314 A | 8/1982 | Radel et al. |
| 4,352,356 A | 10/1982 | Tong |
| 4,438,167 A | 3/1984 | Schwarz |
| 4,463,045 A | 7/1984 | Ahr et al. |
| 4,475,912 A | 10/1984 | Coates |
| 4,496,360 A | 1/1985 | Joffe et al. |
| 4,573,986 A | 3/1986 | Minetola et al. |
| 4,578,073 A | 3/1986 | Dysart et al. |
| 4,579,556 A | 4/1986 | McFarland |
| 4,582,550 A | 4/1986 | Sigl |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,615,695 A | 10/1986 | Cooper |
| 4,625,245 A | 11/1986 | White |
| 4,629,643 A | 12/1986 | Curro et al. |
| 4,643,726 A | 2/1987 | Gegelys |
| 4,650,483 A | 3/1987 | Joffe |
| 4,657,539 A | 4/1987 | Hasse |
| 4,661,102 A | 4/1987 | Shikata et al. |
| 4,673,402 A | 6/1987 | Weisman et al. |
| 4,695,278 A | 9/1987 | Lawson |
| 4,701,170 A | 10/1987 | Wilson et al. |
| 4,704,114 A | 11/1987 | Wilson et al. |
| 4,704,116 A | 11/1987 | Enloe |
| 4,710,187 A | 12/1987 | Boland et al. |
| 4,747,846 A | 5/1988 | Boland et al. |
| 4,756,709 A | 7/1988 | Stevens |
| 4,770,656 A | 9/1988 | Proxmire et al. |
| 4,785,996 A | 11/1988 | Ziecker et al. |
| 4,795,452 A | 1/1989 | Blaney et al. |
| 4,795,454 A | 1/1989 | Dragoo |
| 4,808,176 A | 2/1989 | Kielpikowski |
| 4,808,177 A | 2/1989 | Desmarais et al. |
| 4,808,178 A | 2/1989 | Aziz et al. |
| 4,816,026 A | 3/1989 | Richardson |
| 4,834,735 A | 5/1989 | Alemany et al. |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,872,871 A | 10/1989 | Proxmire et al. |
| 4,888,231 A | 12/1989 | Angstadt |
| 4,892,536 A | 1/1990 | Desmarais et al. |
| 4,892,598 A | 1/1990 | Stevens et al. |
| 4,906,243 A | 3/1990 | Dravland |
| 4,908,247 A | 3/1990 | Baird et al. |
| 4,909,803 A | 3/1990 | Aziz et al. |
| 4,955,880 A | 9/1990 | Rodriquez |
| 4,961,736 A | 10/1990 | McCloud |
| 4,964,857 A | 10/1990 | Osborn |
| 4,968,311 A | 11/1990 | Chickering et al. |
| 4,968,312 A | 11/1990 | Khan |
| 4,978,046 A | 12/1990 | Hagmann et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,019,068 A | 5/1991 | Perez et al. |
| 5,021,051 A | 6/1991 | Hiuke |
| 5,032,120 A | 7/1991 | Freeland et al. |
| 5,037,416 A | 8/1991 | Allen et al. |
| 5,069,672 A | 12/1991 | Wippler et al. |
| 5,087,253 A | 2/1992 | Cooper |
| 5,108,385 A | 4/1992 | Snyder |
| 5,127,108 A | 7/1992 | Weiss |
| 5,137,537 A | 8/1992 | Herron et al. |
| 5,141,870 A | 8/1992 | Bedbrook et al. |
| 5,147,345 A | 9/1992 | Young et al. |
| 5,156,793 A | 10/1992 | Buell et al. |
| 5,167,897 A | 12/1992 | Weber et al. |
| 5,185,011 A | 2/1993 | Strasser |
| 5,202,173 A | 4/1993 | Wu et al. |
| 5,207,663 A | 5/1993 | McQueen |
| 5,210,882 A | 5/1993 | Moretz et al. |
| 5,217,447 A | 6/1993 | Gagnon |
| 5,234,423 A | 8/1993 | Alemany et al. |
| 5,254,111 A | 10/1993 | Cancio et al. |
| 5,260,345 A | 11/1993 | Desmarais et al. |
| 5,261,901 A | 11/1993 | Guay |
| 5,269,775 A | 12/1993 | Freeland et al. |
| 5,283,910 A | 2/1994 | Flint |
| 5,290,270 A | 3/1994 | Fisher |
| 5,296,184 A | 3/1994 | Wu et al. |
| 5,306,267 A | 4/1994 | Hahn et al. |
| 5,331,015 A | 7/1994 | Desmarais et al. |
| 5,342,338 A | 8/1994 | Roe |
| 5,354,597 A | 10/1994 | Capik et al. |
| 5,360,422 A | 11/1994 | Brownlee et al. |
| 5,368,584 A | 11/1994 | Clear et al. |
| 5,368,585 A | 11/1994 | Dokken |
| 5,387,207 A | 2/1995 | Dyer et al. |
| 5,401,266 A | 3/1995 | Runeman et al. |
| 5,405,342 A | 4/1995 | Roessler et al. |
| 5,415,650 A | 5/1995 | Sigl |
| 5,435,014 A | 7/1995 | Moretz et al. |
| 5,458,591 A | 10/1995 | Roessler et al. |
| 5,476,457 A | 12/1995 | Roessler et al. |
| 5,509,915 A | 4/1996 | Hanson et al. |
| 5,514,121 A | 5/1996 | Roe et al. |
| 5,518,801 A | 5/1996 | Chappell et al. |
| 5,554,142 A | 9/1996 | Dreier et al. |
| 5,562,648 A | 10/1996 | Peterson |
| 5,571,096 A | 11/1996 | Dobrin et al. |
| 5,607,760 A | 3/1997 | Roe |
| 5,609,587 A | 3/1997 | Roe |
| 5,613,959 A | 3/1997 | Roessler et al. |
| 5,624,425 A | 4/1997 | Gray et al. |
| 5,624,429 A | 4/1997 | Long et al. |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,667,503 A | 9/1997 | Roe et al. |
| 5,671,615 A | 9/1997 | Kjærgaard et al. |
| 5,704,933 A * | 1/1998 | Fell et al. .................. 604/399 |
| 5,716,349 A | 2/1998 | Taylor et al. |
| H1732 H | 6/1998 | Johnson |
| 5,769,838 A | 6/1998 | Buell et al. |
| 5,772,649 A | 6/1998 | Siudzinski |
| 5,776,121 A | 7/1998 | Roe et al. |
| 5,795,347 A | 8/1998 | Roe et al. |
| 5,795,348 A | 8/1998 | Roe et al. |
| 5,814,037 A | 9/1998 | Coates |
| 5,827,261 A | 10/1998 | Osborn et al. |
| 5,843,065 A | 12/1998 | Wyant |
| 5,843,267 A | 12/1998 | Cashaw et al. |
| 5,846,232 A | 12/1998 | Serbiak et al. |
| H1788 H | 2/1999 | Christon et al. |

(56) References Cited

U.S. PATENT DOCUMENTS

| | | |
|---|---|---|
| 5,865,823 A | 2/1999 | Curro |
| 5,906,603 A | 5/1999 | Roe et al. |
| 5,911,713 A | 6/1999 | Yamada et al. |
| 5,938,648 A | 8/1999 | Lavon et al. |
| 5,941,864 A | 8/1999 | Roe |
| 5,947,946 A | 9/1999 | Fisher et al. |
| 5,968,025 A | 10/1999 | Roe et al. |
| 5,984,911 A | 11/1999 | Siebers et al. |
| 6,007,528 A | 12/1999 | Osborn |
| 6,010,491 A | 1/2000 | Roe et al. |
| 6,083,211 A | 7/2000 | Desmarais |
| 6,120,487 A | 9/2000 | Ashton |
| 6,142,983 A | 11/2000 | Suprise et al. |
| 6,207,738 B1 | 3/2001 | Zuckerman et al. |
| 6,213,991 B1 | 4/2001 | Kling et al. |
| 6,218,593 B1 * | 4/2001 | Torimae et al. ............... 604/366 |
| 6,229,061 B1 | 5/2001 | Draggo et al. |
| 6,240,569 B1 | 6/2001 | Van Gompel et al. |
| 6,251,097 B1 | 6/2001 | Kline et al. |
| 6,254,583 B1 | 7/2001 | Coates |
| 6,258,308 B1 | 7/2001 | Brady et al. |
| 6,278,037 B1 | 8/2001 | Schmidt et al. |
| 6,287,169 B1 | 9/2001 | Willms et al. |
| 6,291,039 B1 | 9/2001 | Combe et al. |
| 6,307,119 B1 | 10/2001 | Cammarota et al. |
| 6,368,444 B1 | 4/2002 | Jameson et al. |
| 6,414,215 B1 | 7/2002 | Roe |
| 6,420,627 B1 | 7/2002 | Ohnishi et al. |
| 6,423,042 B1 | 7/2002 | Sasaki |
| 6,423,043 B1 | 7/2002 | Gustafsson |
| 6,432,098 B1 | 8/2002 | Kline et al. |
| 6,468,257 B1 | 10/2002 | Ono et al. |
| 6,482,191 B1 | 11/2002 | Roe et al. |
| 6,514,362 B1 | 2/2003 | Zuckerman et al. |
| 6,526,631 B1 | 3/2003 | Alberg et al. |
| 6,547,773 B2 | 4/2003 | Kleinschmidt et al. |
| 6,547,774 B2 | 4/2003 | Ono et al. |
| 6,562,016 B2 | 5/2003 | Shinkai |
| 6,575,951 B1 | 6/2003 | Ono et al. |
| 6,579,273 B2 | 6/2003 | Dupuy |
| 6,623,466 B1 | 9/2003 | Richardson |
| 6,669,618 B2 | 12/2003 | Reising et al. |
| 6,680,422 B2 | 1/2004 | Roe |
| 6,709,423 B1 | 3/2004 | Herrlein et al. |
| 6,716,441 B1 | 4/2004 | Osborne et al. |
| 6,764,477 B1 | 7/2004 | Chen et al. |
| 6,764,478 B2 | 7/2004 | Ashton et al. |
| 6,786,895 B1 | 9/2004 | Schmitz |
| 6,794,023 B1 | 9/2004 | Melik et al. |
| 6,807,685 B1 | 10/2004 | Hasegawa et al. |
| 6,811,643 B2 | 11/2004 | McAmish et al. |
| 6,817,992 B1 | 11/2004 | Sassak et al. |
| 6,821,612 B1 | 11/2004 | Melik et al. |
| 6,843,949 B2 | 1/2005 | Brady et al. |
| 6,878,647 B1 | 4/2005 | Rezai et al. |
| 6,884,494 B1 | 4/2005 | Curro et al. |
| 6,890,872 B2 | 5/2005 | Bond et al. |
| 6,893,388 B2 | 5/2005 | Reising et al. |
| 6,905,987 B2 | 6/2005 | Noda et al. |
| 6,921,393 B2 | 7/2005 | Tears et al. |
| 6,936,039 B2 | 8/2005 | Kline et al. |
| 6,964,720 B2 | 11/2005 | Schneider et al. |
| 6,966,720 B2 | 11/2005 | Moss |
| 6,980,872 B2 | 12/2005 | Kano et al. |
| 7,037,569 B2 | 5/2006 | Curro et al. |
| 7,060,149 B2 | 6/2006 | Ortega et al. |
| 7,101,359 B2 | 9/2006 | Kline et al. |
| 7,150,334 B2 | 12/2006 | Kodan et al. |
| 7,166,095 B1 | 1/2007 | Coates |
| 7,175,613 B2 | 2/2007 | Sugiyama et al. |
| 7,211,531 B2 | 5/2007 | Schneider et al. |
| 7,223,818 B2 | 5/2007 | Autran et al. |
| 7,250,549 B2 | 7/2007 | Richlen et al. |
| 7,264,615 B2 | 9/2007 | Sherrod et al. |
| 7,322,967 B2 * | 1/2008 | Kondo ................. 604/385.29 |
| 7,344,526 B2 | 3/2008 | Yang et al. |
| 7,387,620 B2 | 6/2008 | Watanabe et al. |
| 7,407,468 B2 | 8/2008 | Reising et al. |
| 7,432,413 B2 | 10/2008 | Roe et al. |
| 7,458,961 B2 | 12/2008 | Carstens |
| 7,462,173 B2 | 12/2008 | Carstens |
| 7,481,801 B2 | 1/2009 | Carstens |
| 7,491,196 B2 | 2/2009 | Frank et al. |
| 7,537,587 B2 | 5/2009 | Carstens |
| 7,576,019 B2 | 8/2009 | Bond et al. |
| 7,591,811 B2 | 9/2009 | Wilkinson |
| 7,629,501 B2 | 12/2009 | Labit et al. |
| 7,666,175 B2 | 2/2010 | Trennepohl |
| 7,695,463 B2 | 4/2010 | Lavon et al. |
| 7,771,406 B2 | 8/2010 | Mueller et al. |
| 7,771,408 B2 | 8/2010 | Mueller et al. |
| 7,776,770 B2 | 8/2010 | Wang et al. |
| 7,776,771 B2 | 8/2010 | Autran et al. |
| 7,785,311 B2 | 8/2010 | Carstens |
| 7,789,867 B2 | 9/2010 | Carstens |
| 7,803,147 B2 | 9/2010 | Carstens |
| 7,820,875 B2 | 10/2010 | Roe et al. |
| 7,824,387 B2 | 11/2010 | LaVon |
| 7,833,211 B2 | 11/2010 | Mansfield |
| 7,842,627 B2 | 11/2010 | Gao et al. |
| 7,872,169 B2 | 1/2011 | Ruiz et al. |
| 7,875,014 B2 | 1/2011 | Hendren et al. |
| 7,887,527 B2 | 2/2011 | Hayashi et al. |
| 7,914,507 B1 | 3/2011 | Magee |
| 7,993,322 B2 | 8/2011 | Brud et al. |
| 8,002,760 B2 | 8/2011 | Ehrnsperger et al. |
| 8,016,803 B2 | 9/2011 | Mueller et al. |
| 8,017,827 B2 | 9/2011 | Hundorf et al. |
| 8,062,278 B2 | 11/2011 | Kline et al. |
| 8,066,685 B2 | 11/2011 | Olson et al. |
| 8,118,801 B2 | 2/2012 | Macura et al. |
| 8,158,043 B2 | 4/2012 | Gibson et al. |
| 8,206,366 B2 | 6/2012 | Datta et al. |
| 8,262,635 B2 | 9/2012 | Labit et al. |
| 8,377,023 B2 | 2/2013 | Sawyer et al. |
| 8,568,380 B2 | 10/2013 | Brownlee |
| 8,652,115 B2 * | 2/2014 | Roe et al. ................. 604/385.14 |
| 8,669,409 B2 * | 3/2014 | Roe .............................. 604/367 |
| 8,702,667 B1 * | 4/2014 | Johnson ................. 604/385.09 |
| 2001/0023341 A1 * | 9/2001 | Karami ................... 604/385.03 |
| 2001/0023344 A1 * | 9/2001 | Oba ............................ 604/395 |
| 2002/0010452 A1 | 1/2002 | Dupuy |
| 2002/0035747 A1 | 3/2002 | Kusibojoska et al. |
| 2002/0128619 A1 | 9/2002 | Carlbark et al. |
| 2002/0151858 A1 * | 10/2002 | Karami et al. ............. 604/385.3 |
| 2003/0055394 A1 | 3/2003 | Gibbs |
| 2003/0088220 A1 | 5/2003 | Molander et al. |
| 2003/0091807 A1 | 5/2003 | Desai et al. |
| 2003/0114805 A1 | 6/2003 | Rainville et al. |
| 2003/0125701 A1 | 7/2003 | Widlund |
| 2003/0163104 A1 | 8/2003 | Tears et al. |
| 2003/0163108 A1 | 8/2003 | Tears et al. |
| 2003/0233082 A1 | 12/2003 | Kline et al. |
| 2004/0023771 A1 | 2/2004 | Reising et al. |
| 2004/0127867 A1 | 7/2004 | Odorzynski et al. |
| 2005/0033258 A1 | 2/2005 | Suzuki et al. |
| 2005/0096624 A1 | 5/2005 | Hoshino et al. |
| 2005/0148974 A1 | 7/2005 | Datta et al. |
| 2005/0148980 A1 * | 7/2005 | Fitton ....................... 604/385.3 |
| 2005/0164587 A1 | 7/2005 | Melik et al. |
| 2005/0177123 A1 | 8/2005 | Catalan |
| 2005/0215965 A1 | 9/2005 | Schmidt et al. |
| 2005/0215968 A1 | 9/2005 | Henderson |
| 2005/0215970 A1 | 9/2005 | Kline et al. |
| 2005/0215971 A1 | 9/2005 | Roe et al. |
| 2005/0234411 A1 | 10/2005 | Ashton et al. |
| 2006/0035055 A1 | 2/2006 | Schneider et al. |
| 2006/0047260 A1 | 3/2006 | Ashton et al. |
| 2006/0058766 A1 | 3/2006 | Mueller et al. |
| 2006/0069372 A1 | 3/2006 | Chakavarty et al. |
| 2006/0087053 A1 | 4/2006 | O'Donnell et al. |
| 2006/0095012 A1 | 5/2006 | Cohen |
| 2006/0107505 A1 | 5/2006 | Desai et al. |
| 2006/0129114 A1 | 6/2006 | Mason et al. |

(56) References Cited

U.S. PATENT DOCUMENTS

| | | |
|---|---|---|
| 2006/0129116 A1 | 6/2006 | Hughes et al. |
| 2006/0178652 A1 | 8/2006 | Miller |
| 2006/0189956 A1 | 8/2006 | Catalan |
| 2006/0229582 A1* | 10/2006 | LaVon .................. 604/385.14 |
| 2006/0247599 A1 | 11/2006 | Mullen et al. |
| 2006/0259001 A1* | 11/2006 | Roehrl et al. ........... 604/385.11 |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2006/0264885 A1 | 11/2006 | Carstens |
| 2006/0282056 A1 | 12/2006 | McDonald |
| 2006/0293637 A1 | 12/2006 | La Von et al. |
| 2007/0005038 A1 | 1/2007 | Mansfield et al. |
| 2007/0032772 A1 | 2/2007 | Ehrnsperger et al. |
| 2007/0123834 A1 | 5/2007 | McDowall et al. |
| 2007/0142798 A1 | 6/2007 | Goodlander et al. |
| 2007/0142816 A1 | 6/2007 | Carstens |
| 2007/0191806 A1 | 8/2007 | Mueller et al. |
| 2007/0203301 A1 | 8/2007 | Autran et al. |
| 2007/0239130 A1 | 10/2007 | Trennepohl |
| 2007/0249254 A1 | 10/2007 | Mansfield |
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2007/0293111 A1 | 12/2007 | Mansfield |
| 2008/0004582 A1 | 1/2008 | Lodge et al. |
| 2008/0004583 A1 | 1/2008 | Desai et al. |
| 2008/0004584 A1 | 1/2008 | Langdonl et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0009817 A1 | 1/2008 | Norrby |
| 2008/0015537 A1 | 1/2008 | Lodge et al. |
| 2008/0033388 A1 | 2/2008 | Muellerg et al. |
| 2008/0045917 A1 | 2/2008 | Autran et al. |
| 2008/0069773 A1 | 3/2008 | Franco et al. |
| 2008/0081854 A1 | 4/2008 | Wang et al. |
| 2008/0114327 A1 | 5/2008 | Barge |
| 2008/0119813 A1 | 5/2008 | Carstens |
| 2008/0119814 A1 | 5/2008 | Carstens |
| 2008/0119815 A1 | 5/2008 | Carstens |
| 2008/0119816 A1 | 5/2008 | Carstens |
| 2008/0125739 A1 | 5/2008 | Lodge et al. |
| 2008/0188822 A1 | 8/2008 | Lodge et al. |
| 2008/0215028 A1 | 9/2008 | Brown et al. |
| 2008/0224351 A1 | 9/2008 | Curro et al. |
| 2008/0287983 A1 | 11/2008 | Smith et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0018520 A1* | 1/2009 | Tachibana ................ 604/385.23 |
| 2009/0069722 A1 | 3/2009 | Flaction et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0079778 A1 | 3/2009 | Fellingham et al. |
| 2009/0127742 A1 | 5/2009 | Qureshi et al. |
| 2009/0216209 A1 | 8/2009 | Ekstrom |
| 2010/0004616 A1 | 1/2010 | Nakamura |
| 2010/0005570 A1 | 1/2010 | Rachman |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe |
| 2010/0201024 A1 | 8/2010 | Gibson et al. |
| 2010/0331803 A1 | 12/2010 | Saito |
| 2011/0024940 A1 | 2/2011 | Qureshi et al. |
| 2011/0137277 A1 | 6/2011 | Hough et al. |
| 2011/0172628 A1 | 7/2011 | Roe et al. |
| 2011/0288518 A1 | 11/2011 | Roe et al. |
| 2012/0022481 A1 | 1/2012 | Roe et al. |
| 2012/0022491 A1 | 1/2012 | Roe et al. |
| 2012/0049404 A1 | 3/2012 | Gibson et al. |
| 2012/0123366 A1 | 5/2012 | Brownlee |
| 2013/0006207 A1 | 1/2013 | Roe et al. |
| 2013/0102986 A1 | 4/2013 | Ruiz et al. |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard, IV et al. |
| 2014/0018761 A1 | 1/2014 | Orchard, IV et al. |
| 2014/0018762 A1 | 1/2014 | Vignali et al. |
| 2014/0018763 A1 | 1/2014 | Evenson et al. |
| 2014/0018764 A1 | 1/2014 | Johnston et al. |

FOREIGN PATENT DOCUMENTS

| | | |
|---|---|---|
| CA | 2221209 | 11/1996 |
| CA | 2 365 577 | 6/2003 |
| DE | 103 03 903 A1 | 11/2003 |
| EP | 0 023 804 | 2/1981 |
| EP | 0 187 726 | 7/1986 |
| EP | 319314 A2 | 6/1989 |
| EP | 0667136 | 8/1995 |
| EP | 549988 B1 | 6/1998 |
| EP | 0998892 | 5/2000 |
| EP | 796069 | 8/2000 |
| EP | 796069 B1 | 8/2000 |
| EP | 763353 B1 | 6/2002 |
| FR | 2532337 | 3/1984 |
| GB | 112638 | 1/1918 |
| GB | 2 440 314 | 1/2008 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 62-110903 | 7/1987 |
| JP | 03-091325 | 1/1990 |
| JP | 4-7792 | 11/1990 |
| JP | 06-178795 | 1/1993 |
| JP | 2001-346826 | 12/2001 |
| JP | 2002-325786 | 11/2002 |
| JP | 2003-038564 | 2/2003 |

(56) References Cited

FOREIGN PATENT DOCUMENTS

| | | |
|---|---|---|
| JP | 2003-093438 | 4/2003 |
| JP | 2003-190213 | 7/2003 |
| JP | 2004-261332 | 9/2004 |
| JP | 2005-6827 | 1/2005 |
| JP | 2005-111119 | 4/2005 |
| JP | 2005-118533 | 5/2005 |
| JP | 3109189 | 5/2005 |
| JP | 2007-244506 | 3/2006 |
| JP | 2008-237231 | 10/2008 |
| JP | 2009-153736 | 7/2009 |
| JP | 47-40720 | 8/2011 |
| WO | WO-90/08524 | 8/1990 |
| WO | WO-91/16871 A1 | 11/1991 |
| WO | WO-92/01431 A1 | 2/1992 |
| WO | WO-92/15444 | 9/1992 |
| WO | WO-94/15563 A1 | 7/1994 |
| WO | WO-94/15663 A1 | 7/1994 |
| WO | WO-95/10992 A1 | 4/1995 |
| WO | WO-95/16746 A1 | 6/1995 |
| WO | WO-95/16746 A1 | 6/1995 |
| WO | WO-96/17572 A1 | 6/1996 |
| WO | WO-96/24319 | 8/1996 |
| WO | WO-96/32912 A1 | 10/1996 |
| WO | WO-00/65348 A1 | 11/2000 |
| WO | WO-02/066086 | 8/2002 |
| WO | WO-2004/060229 A2 | 7/2004 |
| WO | WO-2005/039469 | 5/2005 |
| WO | WO-2005/052052 | 6/2005 |
| WO | WO-2005/096855 | 10/2005 |
| WO | WO-2005/097031 | 10/2005 |
| WO | WO-2008/030984 A2 | 3/2008 |
| WO | WO-2008/120959 | 10/2008 |
| WO | WO-2008/142634 | 11/2008 |
| WO | WO-2010/053006 | 5/2010 |
| WO | WO 2010078661 | 7/2010 |
| WO | WO-2012/167844 | 12/2012 |

OTHER PUBLICATIONS www.fuzzibunz.com—Web pages dated Nov. 23, 2009.
www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.
Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2k Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
37 Photographs (obtained from Marketing Technology Service, Inc.) of a product believed to be a product of Kao Corp. and sold in Japan in 1986 (translations provided by Applicants.
Data Sheet, p. V-17, from "Baby Diaper Design Update—1987", publication of Marketing Technology Service, Inc., product believed to be a product of Kao Corp. sold in Japan in 1986 or 1987.
International Search and Written Report, PCT/US2012/044821, date of mailing Dec. 13, 2012.
All Office Actions, Responses and Claims, U.S. Appl. No. 13/183,952.
All Office Actions, Responses and Claims, U.S. Appl. No. 12/687,437.
All Office Actions, Responses and Claims, U.S. Appl. No. 12/687,493.
All Office Actions, Responses and Claims, U.S. Appl. No. 12/687,527.
All Office Actions, Responses and Claims, U.S. Appl. No. 12/687,538.
All Office Actions, Responses and Claims, U.S. Appl. No. 12/687,554.
All Office Actions, Responses and Claims, U.S. Appl. No. 12/687,444.
All Office Actions, Responses and Claims, U.S. Appl. No. 12/785,152.
All Office Actions, Responses and Claims, U.S. Appl. No. 12/785,166.
All Office Actions, Responses and Claims, U.S. Appl. No. 12/785,181.
All Office Actions, Responses and Claims, U.S. Appl. No. 14/053,014.
All Office Actions, Responses and Claims, U.S. Appl. No. 12/841,553.
All Office Actions, Responses and Claims, U.S. Appl. No. 12/841,467.
All Office Actions, Responses and Claims, U.S. Appl. No. 13/859,015.
All Office Actions, Responses and Claims, U.S. Appl. No. 12/841,600.
All Office Actions, Responses and Claims, U.S. Appl. No. 14/014,440.
All Office Actions, Responses and Claims, U.S. Appl. No. 13/537,626.

* cited by examiner

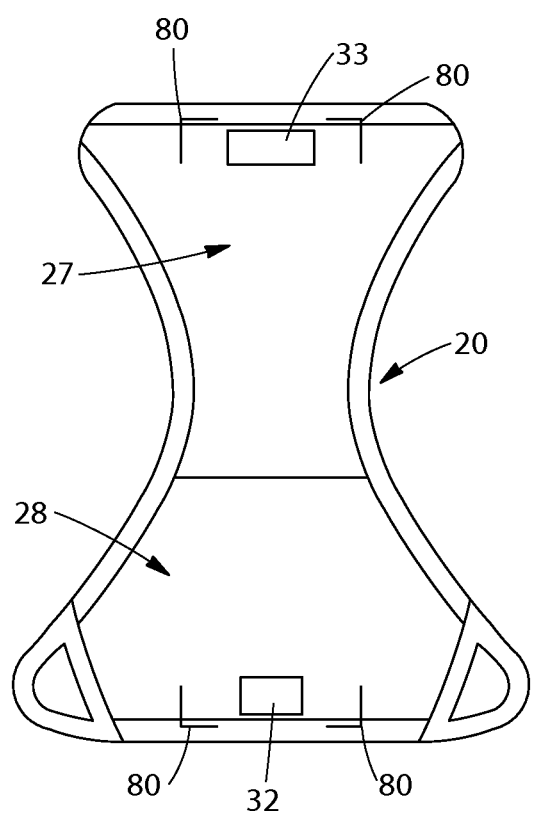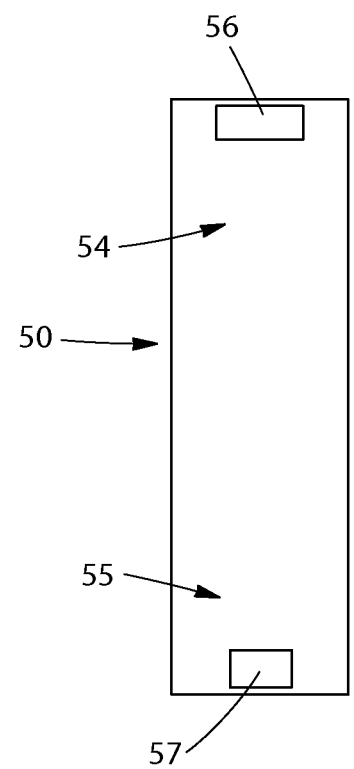
Fig. 2M
Fig. 2N

TWO-PIECE WEARABLE ABSORBENT ARTICLE HAVING ADVANTAGEOUS FRONT WAIST REGION AND LANDING ZONE CONFIGURATION

CROSS REFERENCE TO RELATED APPLICATION

To the extent allowable, this application claims the benefit of the filing date of U.S. Provisional Applications Nos. 61/503,189 and 61/503,215 filed Jun. 30, 2011, the substances of which are incorporated herein by reference.

FIELD OF THE INVENTION

The present invention relates generally to the field of diapers and other wearable absorbent articles having features for the containment and absorption of bodily exudates, and more particularly, to such articles having disposable absorbent inserts and reusable outer covers.

BACKGROUND OF THE INVENTION

It is likely that reusable diapers made of cloth have been in use since the invention of cloth. Reusable cloth diapers, however, present difficulties relating to sanitation needs, in handling, laundering and effectively sanitizing soiled diapers for re-use. Reusable cloth diapers also may be relatively unreliable with respect to containing bodily exudates (i.e., they may tend to leak). Because a wet cloth diaper may be in direct contact with the skin, unless wetness is quickly detected and the wet diaper removed, it may promote over-hydration of the wearer's skin, which makes the skin vulnerable to diaper rash.

The introduction of disposable diapers in relatively recent times has mitigated these disadvantages for many. Generally, upon removal from a wearer, a soiled disposable diaper need not be emptied, laundered or handled to any significant extent, but rather, may be discarded as is. Any soiled areas of the wearer's body may then be cleaned, and a clean new disposable diaper may be placed on the wearer as necessary. Many current disposable diapers have structures that make them relatively more effective at containing exudates than traditional cloth diapers. Many have structures and materials that make them relatively more effective at conveying and storing liquid exudates away from the wearer's skin. Some have features that enable them to "breathe", thereby reducing humidity inside the diaper, and some even include skin care compositions that are transferred to the skin when the diaper is worn. Such features may reduce the likelihood and/or extent of skin over-hydration and otherwise promote or help maintain skin health.

For economic reasons, currently most disposable diapers are made of substantial proportions of materials derived from petroleum, such as polypropylene and/or polyethylene. These materials often appear in the form of spun fibers forming cloth-like nonwoven web materials, or alternatively or in addition, films.

In recent years concerns have arisen concerning the "environmental footprint" of human activities of all kinds. The manufacture and use of diapers is no exception, particularly in view of the growing human population, i.e., the growing number of babies. One view seems to be that use of disposable diapers is detrimental to the environment because the materials of which they are typically made may be derived from non-renewable resources and require substantial amounts of energy in their manufacture. Additionally, because disposable diapers typically are not re-used or recycled, their use may be deemed by some to be unsatisfactorily taxing upon disposal facilities such as landfills. If the alternative is reusable cloth diapers, however, another view seems to be that the increased use of energy (e.g., for operating equipment, heating laundry water, and treating wastewater) and chemicals (e.g., detergents and water treatment agents), necessary for laundering soiled diapers at the rate they are typically used, and treating the associated wastewater, present their own set of stresses on the environment. As may be appreciated, analysis concerning which alternative is more "environmentally friendly" is complicated, and undisputed conclusions either way do not yet appear to exist.

Regardless of which alternative one may believe is more environmentally friendly, however, it appears that in developed nations, today's disposable diapers are generally favored over reusable cloth diapers among caregivers of babies and young children. This is probably attributable to the advantages of reducing or eliminating the unpleasantness, sanitary concerns, and extra work and/or expense associated with handling and laundering soiled reusable cloth diapers, better containment of exudates, and effectiveness at promoting and/or helping maintain skin health.

Manufacture of wholly disposable diapers is generally considered a capital-intensive business. This is a consequence of the complex machinery required to produce product from incoming material streams at economically-feasible production rates, which often exceed 450 or more articles per manufacturing line, per minute. Any innovation that has the potential to simplify the process or the equipment required, or reduce material costs, has the corresponding potential to reduce per-article costs for the manufacturer and the consumer.

Several designs of diapers that include a reusable cloth outer cover and either a reusable or a disposable absorbent insert have been manufactured and marketed. However, for the user, these designs have still presented at least some of the disadvantages of traditional cloth diapers, while not providing some of the advantages available from current disposable diaper designs.

In view of the concerns set forth above, it would be advantageous if a wearable absorbent article were available that provides advantages afforded by both disposable and reusable diapers, while reducing the respective disadvantages of these alternatives. It also would be advantageous if a construction were provided that could simplify manufacturing processes and/or reduce costs.

BRIEF DESCRIPTION OF THE DRAWINGS

FIG. 2M is a plan view of an outer cover opened and laid flat, inner surface facing the viewer;

FIG. 2N is a plan view of an insert opened and laid flat, outer (garment-facing) surface facing the viewer;

DETAILED DESCRIPTION OF THE INVENTION

Definitions

Figure 1:
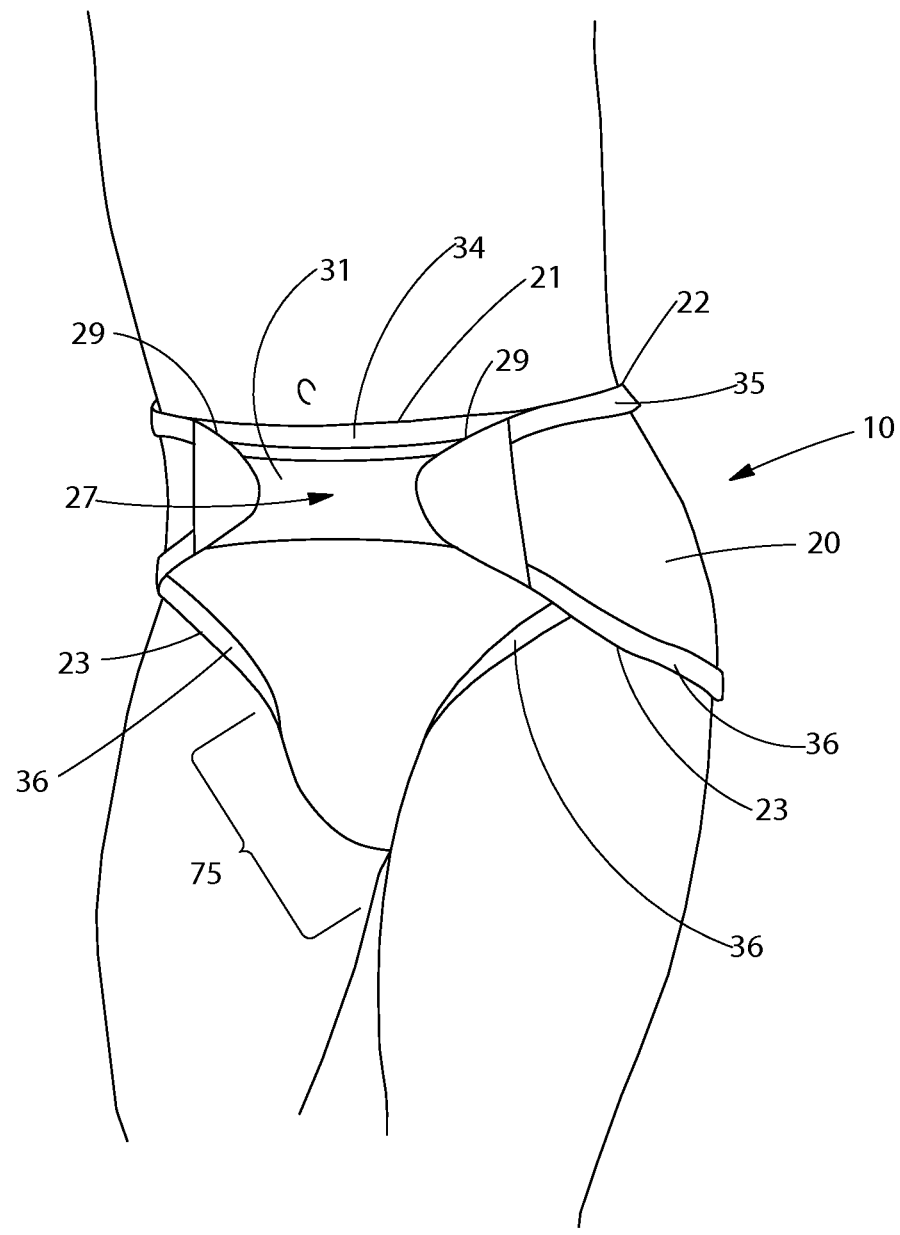
FIG. 1 is a perspective view of a wearable absorbent article as it might appear being worn by a wearer about the lower torso.

For purposes of this description, the following terms have the meanings set forth:

"Absorbent insert" and "insert" mean a component of a wearable absorbent article that is adapted to contain and/or absorb urine, feces, menses or any combination thereof, and is adapted to be installable and removable as a modular unit, from an outer cover. Herein, an absorbent insert may also be referred to as an "absorbent assembly". The terms "absorbent insert," "insert" and "absorbent assembly" may be used interchangeably herein.

"Chassis" means a component of a wearable absorbent article that is adapted to be worn about the lower torso of a wearer, and is adapted to support an absorbent insert and hold the insert next to the wearer's body. Herein, a chassis may also be referred to as an "outer cover". The terms "outer cover" and "chassis" are interchangeable for purposes herein.

"Disposable", when referring to an absorbent insert, means that the absorbent insert is not adapted or intended to be effectively sanitarily laundered in an ordinary household laundering process and ordinary household equipment, and thereby is ordinarily unsuitable for sanitary and effective reuse so as to provide as-new intended functions and performance, following soiling by exudates and removal from an outer cover. By way of non-limiting examples, effective laundering may be frustrated or prevented, causing the insert to be disposable, by inclusion of materials and/or construction: that do not retain their substantial as-new physical shape or structure through ordinary household laundering and drying so as to be effective as-new in reuse; that absorb aqueous liquids and cannot be sufficiently dried/dehydrated in ordinary household drying equipment and ordinary drying cycles so as to be effective as-new in reuse; that dissolve or substantially degrade in ordinary household laundering or drying, causing the insert to be substantially damaged or rendered useless;

and/or that cannot be effectively cleaned of exudate material through ordinary laundering, so as to be sanitary and otherwise acceptable for re-use.

"Fastener component" means any component of a system that effects removable fastening, attachment or holding of a first structure to a second structure. The system may have a single fastener component, for example, an adhesive patch on the first structure adapted to adhere to one or more types of surfaces on the second structure, or a hook, or patch of hooks on the first structure, adapted to catch on one or more types of surfaces on the second structure. By way of further example, any structure such as a pocket, strap, hook, buckle, etc. on a first structure adapted to capture and retain, in whole or in part, the second structure, is a "fastener component" as used herein. The system also may comprise two or more fastener components, for example, respective components of a hook-and-loop fastening system (such as VELCRO), respective surfaces having a cohesive material applied thereto; male and female snap fastener components, a button and button hole, slot or loop, other fastenably cooperating elements, etc. Other examples of fastener components include zipper components, "zip lock" engaging components, loops, posts, pockets, bands or straps, microfasteners, macrofasteners, and fastener components such as described in U.S. Pat. Nos. 6,936,039; 6,893,388; 6,669,618; 6,432,098; and 6,251,097, and U.S. Published Applications, Pub. Nos. 2005/0234419; 2005/0215971; 2005/0215970; 2005/0130821; 2004/0023771; 2003/0233082; 2003/0119641; 2003/0088220; and 2002/0169431.

"Lateral" (and forms thereof), with respect to a wearer, means along a direction generally transverse or across the direction extending from the front to the rear of the wearer, or vice versa. With respect to a component of a wearable absorbent article, "lateral" (and forms thereof), means along a direction generally transverse or across the direction extending along the component as it would be properly situated on a wearer, from the front to the rear of the wearer, or vice versa.

"Longitudinal" (and forms thereof), with respect to a wearer, means along a direction generally extending from the front to the rear of the wearer, or vice versa. With respect to a component of a wearable absorbent article, "longitudinal" (and forms thereof), means along a direction generally extending along the component as it would be properly situated on a wearer, from the front to the rear of the wearer, or vice versa.

"Loops material" refers to any discrete layer of fabric, web or sheet material disposed on, and/or forming a portion of, an outer cover, that may be differentiated from an adjacent discrete material disposed on, and/or forming another portion of, the outer cover, by having a greater uncompressed caliper and/or greater attachment strength per unit surface area, and is present on the outer cover in a position suitable to attachably receive and engage a hooks material, to serve a designed function of the outer cover ("receiving position"). "Greater attachment strength per surface area" means that a sample of the loops material will exhibit greater resistance to separation from an applied facing hooks material of a given surface area, applied to the loops material by an ordinary amount of pressure as would be applied by a person applying the outer cover, by a separating force exerted normal to planes approximated by the respective materials as mounted on respective flat test plates, than a sample of the adjacent discrete material will. By way of non-limiting example, a receiving position may be in the front portion of the outer cover adjacent or near the front waist edge, thus forming a landing zone for receiving hooks material disposed, for example, on fastening members or fastening ears extending laterally from the back region of the outer cover.

"Outer cover" means a component of a wearable absorbent article that is adapted to be worn about the lower torso of a wearer, and is adapted to support an absorbent insert and hold the insert next to the wearer's body. Herein, an outer cover may also be referred to as a "chassis". The terms "outer cover" and "chassis" are interchangeable for purposes herein, and include but are not limited to garments having features as described herein and configured as diapers, diaper covers, underpants, briefs, training pants, shorts, etc.

"Reusable", when referring to an outer cover, means an outer cover that is adapted to permit removal of at least a first insert, and replacement thereof with at least a second insert, without substantial destruction of any components of the outer cover that are necessary to provide the substantial as-new functionality of the outer cover, and without the necessity of any repair or reconstruction following such insert replacement.

"Use," with respect to an outer cover, means one event of the wearing of the outer cover until the time an absorbent insert is replaced.

"User" means a caregiver or other person who may apply a wearable absorbent article to a wearer. Where the wearer is capable of donning the wearable absorbent article him/herself, the wearer is also a "user".

"Wearer" means a person who may wear a wearable absorbent article as described herein.

"Wearable absorbent article" means any article designed to be worn about the lower torso and to contain and/or absorb urine, feces, menses or any combination thereof "Wearable absorbent article" includes but is not limited to baby or children's diapers (of the "tape"-fastenable, otherwise fastenable, "pull-up" or any other variety), training pants and adult incontinence pants, briefs and the like.

Two-Piece Wearable Absorbent Articles

FIG. 1 depicts an example of a wearable absorbent article 10 having certain features, as it might appear while being worn by a wearer. Wearable absorbent article 10 may include an outer cover 20, having front waist edge 21, rear waist edge 22, and a pair of leg opening edges 23.

Figure 2A:
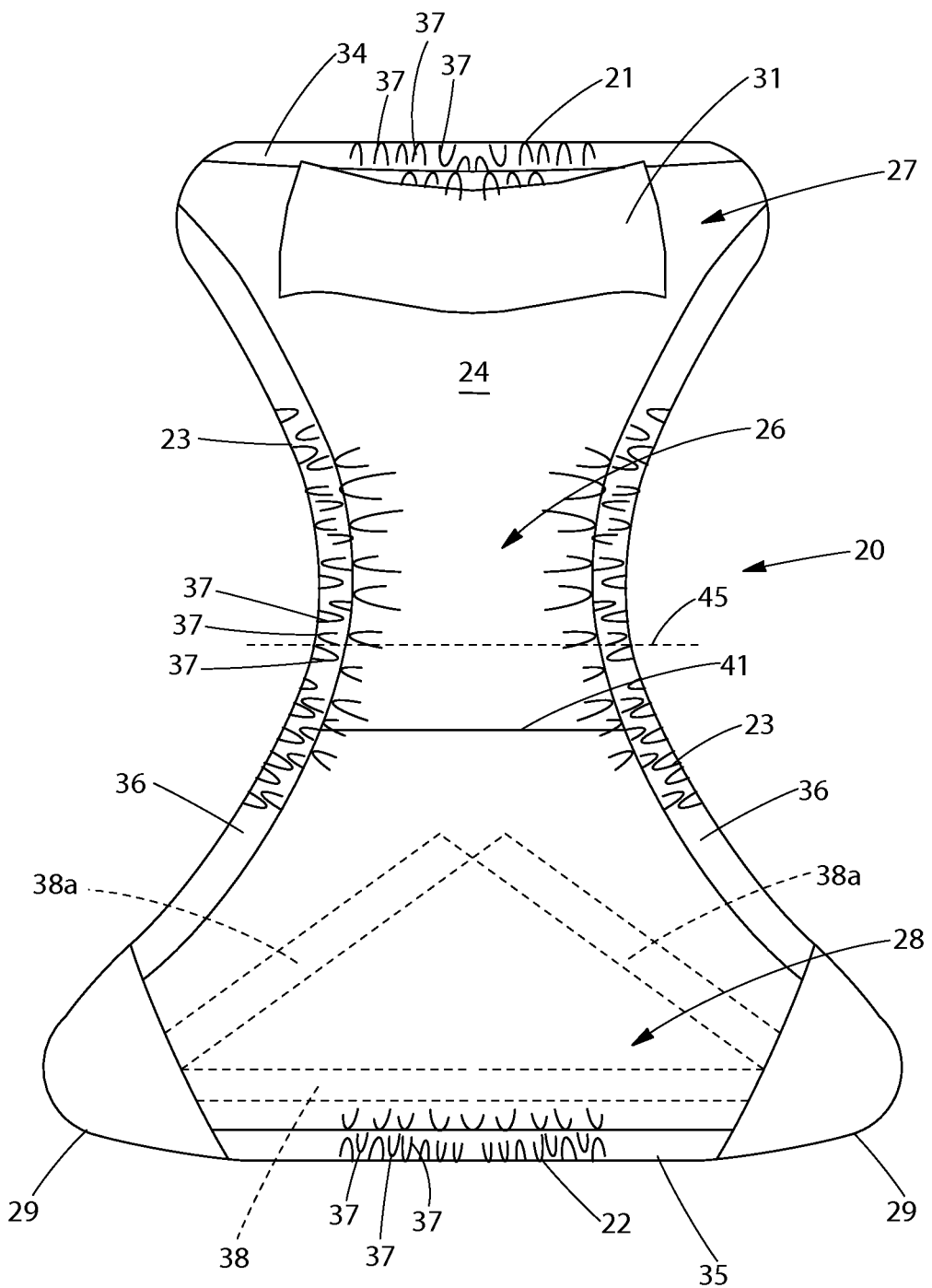
FIG. 2A is a plan view of an outer cover opened and laid flat, outer surface facing the viewer.
Figure 2B:
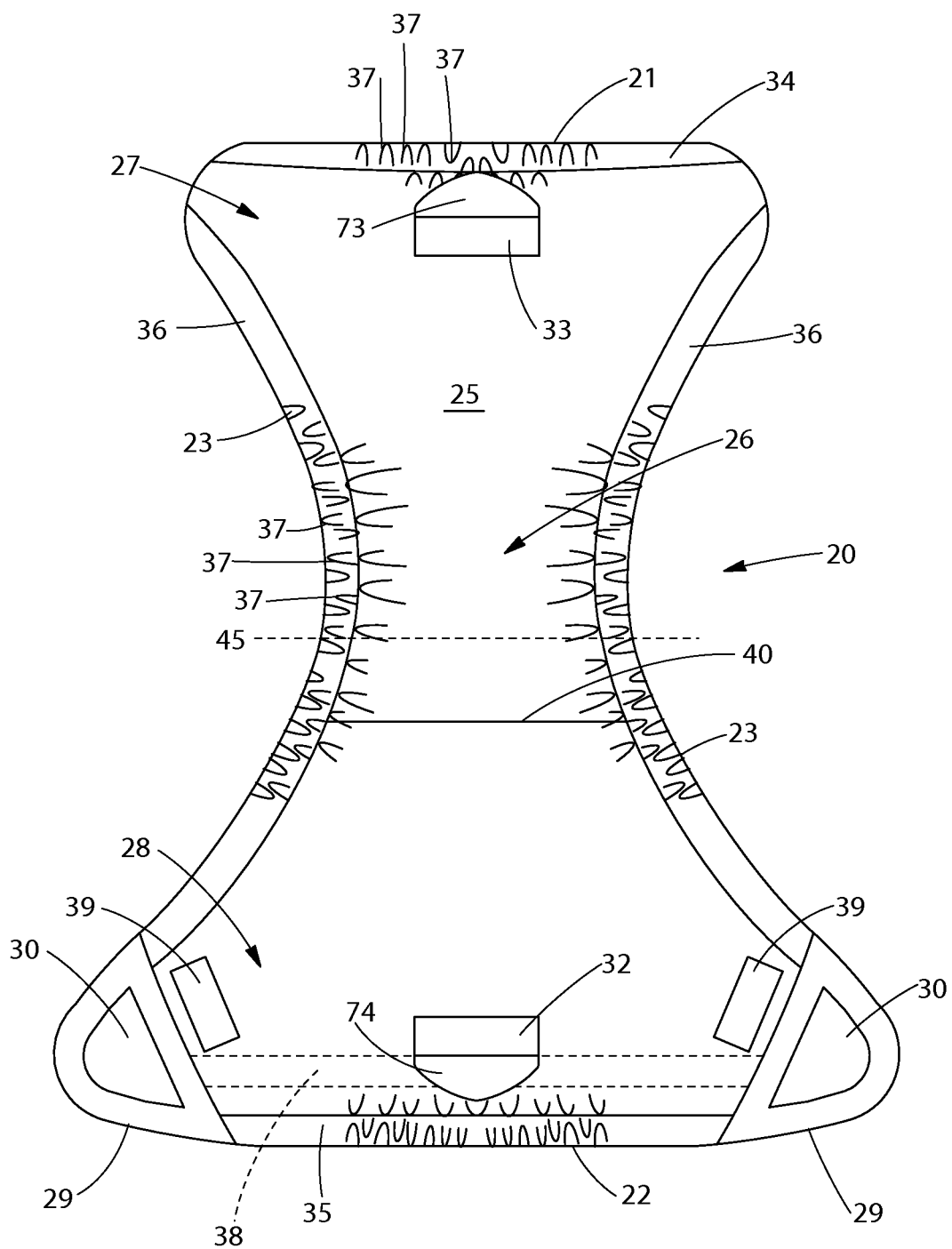
FIG. 2B is a plan view of an outer cover opened and laid flat, inner surface facing the viewer.
Figure 2C:
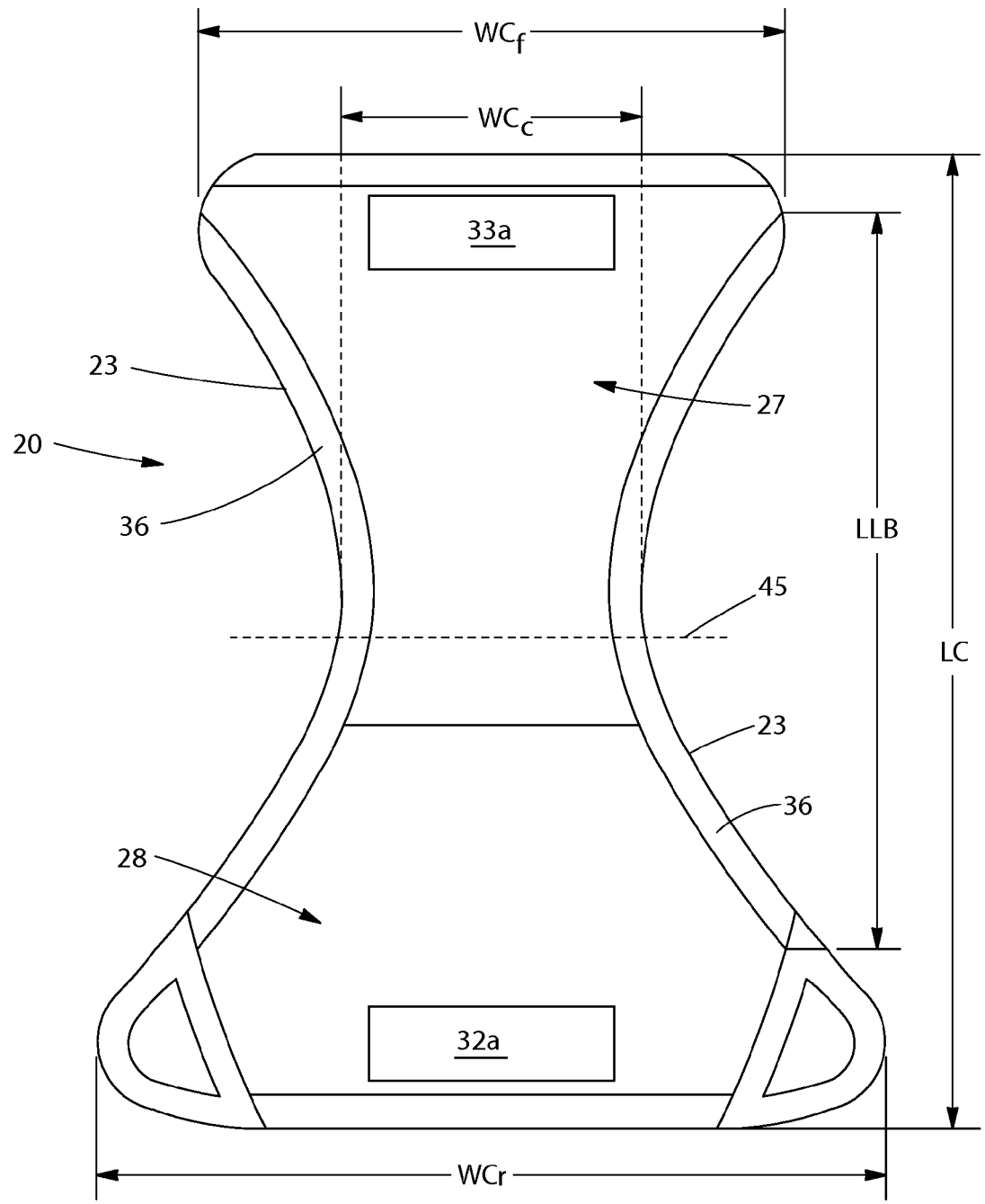
FIG. 2C is a plan view of an outer cover opened and laid flat, inner surface facing the viewer.

FIGS. 2A, 2B and 2C depict an outer cover 20 as it may appear opened and laid flat. In FIG. 2A, the outer, i.e., garment-facing, surfaces of outer cover 20 face the viewer; in FIGS. 2B and 2C, the inner, i.e., wearer-facing, surfaces of outer cover 20 face the viewer. Front and rear waist edges 21, 22 are depicted at the top and bottom of the drawings, respectively. Outer cover 20 may have crotch region 26, front region 27, rear region 28 and a pair of fastening ears 29 laterally extending from rear region 28. Outer cover 20 will have a length LC from the forwardmost portion of front waist edge 21 to the rearwardmost portion of rear waist edge 22, and an outer cover lateral axis 45 equally dividing this length. Thus, front region 27 is forward of outer cover lateral axis 45, and rear region 28 is rearward of outer cover lateral axis 45. Outer cover 20 may have disposed thereon one or more insert fastener components such as front and rear insert fastener components 33, 32.

Figure 3:
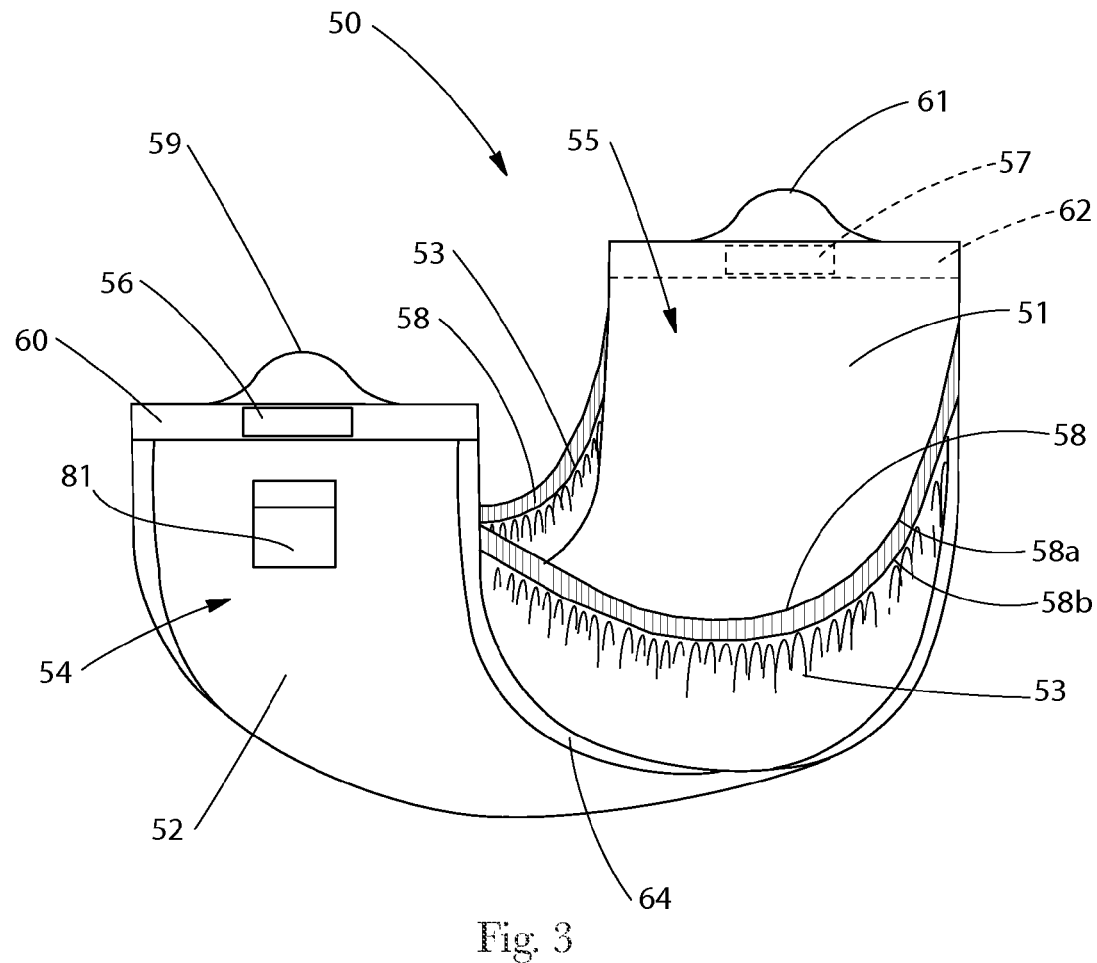
FIG. 3 is a perspective view of a disposable absorbent insert shown apart from an outer cover, as it might appear in a free-standing, relaxed state.
Figure 4:
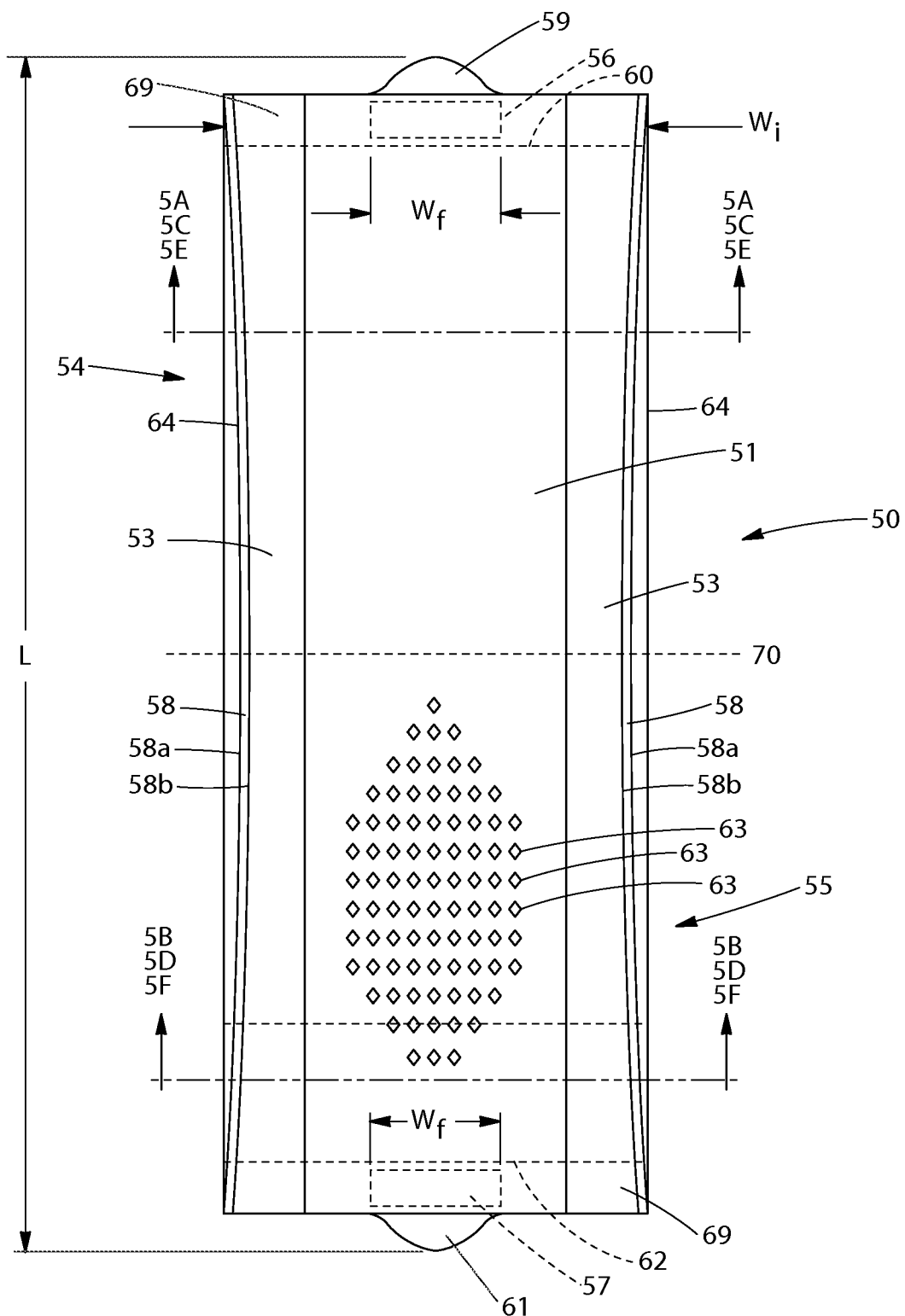
FIG. 4 is a plan view of a disposable absorbent insert shown stretched out and laid flat, body-facing surfaces facing the viewer.

FIG. 3 depicts a disposable absorbent insert 50 that may form an inner component of the wearable absorbent article 10, shown in perspective view as it might appear in a free-standing, relaxed state, apart from outer cover 20. Insert 50 may be designed to contain and/or absorb body exudates, and may be made of pliable materials as will be described further below. Insert 10 has forward region 54 and rearward region 55, and may include front fastener component 56 and rear fastener component 57. Insert 10 may include a body-facing liner or topsheet 51, outer liner or backsheet 52, and a pair of standing cuffs 53. Referring to FIG. 4, insert 50 will have a length L from the forwardmost portion of forward region 54 to the rearwardmost portion of rearward region 55, and an insert lateral axis 70 equally dividing this length. Thus, forward region 54 is forward of insert lateral axis 70, and rearward region 55 is rearward of insert lateral axis 70.

Referring to FIGS. 2B and 3, insert 50 may have rear fastener component 57 disposed thereon. Alternatively, or in addition, outer cover 20 may have rear insert fastener component 32 disposed thereon. Similarly, insert 50 may have front fastener component 56 disposed thereon. Alternatively, or in addition, outer cover 20 may have front insert fastener component 33 disposed thereon. If a two-component fastening system is used, fastener component pairs 57, 32 and 56, 33 may be cooperating components that effect fastening therebetween when these respective components are brought together. Thus, in the example depicted, in order to install absorbent insert 50 into outer cover 20, a user may lay outer cover 20 flat, inner surface 25 facing up, stretch and orient insert 50 such that rear fastener component 57 faces rear insert fastener component 32 and front fastener component 56 faces front insert fastener component 33, and bring these respective fastener component pairs 57, 32 and 56, 33 together to effect fastening therebetween.

If it is desired that outer cover 20 be reusable, for outer cover 20 to remain substantially sanitary and useful (without requiring laundering or disposal) after removal and replacement of an insert, it may be desired that all parts of outer cover 20 remain substantially unsoiled after an exudation of waste (especially fecal matter) by the wearer. Thus, it may be desired that when insert 50 is installed within an outer cover 20, there is no non-removable portion or component of outer cover 20 that lies over or covers a substantial portion of wearer-facing surfaces of insert 50 (expressed differently, no non-removable portion or component of outer cover 20 is situated between a substantial portion of insert 50 and the wearer when the wearable absorbent article is worn), at least in the areas proximate to wearer body features that discharge exudates. Thus, it may be desired that outer cover 20 include no non-removable cover sheet or the like that covers or contains substantial portions of wearer-facing surfaces of insert 50 within outer cover 20, nor any overlying structures such as pockets, straps or flaps that substantially wrap or cover the insert proximate to exudate discharge points, or lie substantially between insert 50 and the wearer's anus and/or genitals, when the wearable absorbent article is worn. If outer cover 20 lacks such overlying structures, this may increase the likelihood that the wearer's exudates will contact only insert 50, and not portions of outer cover 20.

Referring to FIGS. 1, 2A and 2B, it can be seen that wearable absorbent article 10 may be placed on a wearer by wrapping outer cover 20 between the wearer's legs and under the buttocks such that crotch region 26 is between the wearer's legs, bringing front waist edge 21 and rear waist edge 22 into the positions approximately as shown in FIG. 1, and then securing fastening ears 29 to front region 27, thereby forming a pant-like garment about the wearer as suggested in FIG. 1. When insert 50 has been installed into outer cover 20, insert 50 will then be disposed within outer cover 20, next to the wearer, with the standing cuffs 53 oriented and extending longitudinally adjacent the inner portions of leg edges 23 (i.e., longitudinally between the wearer's legs).

Examples of Possible Outer Cover Details

Fastening System

Referring to FIGS. 2A and 2B, to enable fastening of fastening ears 29 to front region 27, fastening ears 29 may have outer cover fastener components 30 disposed thereon. Alternatively, or in addition, front region 27 may have disposed thereon one or more receiving fastener components 31 disposed thereon. Fastener components 30, 31 may be selected so as to be cooperative to effect fastening of ears 29 to front region 27.

In one example, outer cover fastener components 30 may include a patch of hooks, and receiving fastener component 31 may include a patch of loops. An example of a suitable hook-and-loop fastening system is a VELCRO system (a product of Velcro Industries B.V.) A hook-and-loop fastening system provides certain advantages. Because the respective hook and loop components are supplied in sheet form, they may be cut into suitably shaped patches that can be affixed to a cloth or nonwoven substrate by various mechanisms, including adhesive bonding, mechanical bonding, ultrasonic bonding, sewing, stitching, serging, edging, and the like. If patches of hooks or loops are affixed to fastening ears 29 to form outer cover fastener components 30, as suggested by FIG. 2B, a laterally extended patch of cooperating hook or loop material can be affixed to outer cover front region 27 to form a receiving fastener component 31, as suggested by FIG. 2A. By providing for fastening of ears 29 to front region 27 at laterally varying locations thereon, this arrangement provides for easy and simple adjustability of waist opening size of the wearable absorbent article.

In another example, as noted above, the outer cover fastening system may include other types of fastener components. To provide for waist opening size adjustability, fastener components disposed on fastening ears 29 that cooperate with extended surfaces or multiple cooperating fastener components disposed on front region 27 may be used. Receiving fastener components may be multiply disposed on front region 27 in laterally arranged, varying locations, allowing for fastenability of respective ears 29 to front region 27 at laterally varying locations.

Referring to FIG. 2B, outer cover 20 also may have one or more respective fastener protectors 39 disposed thereon. This feature may prevent fastener components having features likely to randomly and unintentionally engage and catch on portions of the outer cover, or other articles, during storage, carrying, laundering and similar/related activities, from doing so, thereby avoiding potential bunching, entangling and/or damage to either outer cover 20 or other articles during such activities. For example, if fastener components 30 are patches of hooks, appropriately placed fastener protectors 39 may include patches of corresponding loops. This will enable the user to fold ears 29 over to engage them with fastener protectors 39, thereby holding them in the folded-over position such that hooks thereon will be concealed and prevented from snagging other articles when outer cover 20 is not being worn.

Materials

Outer cover 20 and/or layers or portions thereof may be made of any knitted, woven or nonwoven textile or textile-like material that is appropriately compatible with skin of the intended wearer(s). Outer cover 20 may be constructed of durable and/or semi-durable materials. Generally, only for purposes of reference in this description, "durable" refers to a woven or knitted textile material of any kind that may be used as a component of a washable clothing article. As used herein, "durable" includes materials which are "launderable" as defined and described in co-pending U.S. application Ser.

Nos. 12/687,412; 12/687,528; and 12/687,425, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on the same day hereof. Generally, only for purposes of this description, "semi-durable" refers to a nonwoven material or laminate thereof that when used as an outer cover material can withstand more than one use with an insert without losing its structural integrity to an extent that renders it unserviceable. As used herein, "semi-durable" includes materials which are "laundering resistant" as defined and described in the co-pending U.S. applications identified immediately above. Thus, outer cover 20 may be constructed of materials and construction that make it reusable and/or washable.

Durable materials of which outer cover 20 may be constructed may include any natural or synthetic textile materials known in the diaper, pant, underwear, performance clothing, sport clothing, or general clothing or textile arts. Durable materials may include woven or knitted textiles made of natural fibers such as cotton, linen, wool, bamboo, hemp, silk, rayon, and the like, as well as blends of any of these fibers with any other(s), or with synthetic fibers. Examples of synthetic fibers suitable for use as components of durable materials include polyester, nylon, spandex and/or other elastomer fibers. Durable outer cover materials also may include breathable water repellent materials such as GORE-TEX (a product of W. L. Gore & Associates, Inc., Elkton, Md.), fabrics comprising microencapsulated phase-change polymer materials such as OUTLAST COMFORTEMP fabrics (products of Outlast Technologies, Boulder, Colo.—see U.S. Pat. No. 6,514,362 and U.S. Pat. No. 6,207,738, for example), COOLMAX (a product of Invista, Wichita, Kans.), and the like.

Suitable durable materials may be formed in any weave or knit fabric form, including birdseye fabric, terry, fleece, flannel, knits, stretch knits, sherpa, suedecloth, microfleece, satin, velour, Burley knits, etc. Suitable examples include POLARTECH POWER DRY, POWER STRETCH and WIND PRO (products of Polartec, LLC, Lawrence, Mass.). Knitted textiles, which may be more inherently stretchable and elastic than woven or nonwoven materials, may impart better fit, comfort and/or appearance to the outer cover. Incorporation of fibers of spandex or other elastomer also may also enhance stretchability and elasticity, and thereby impart better fit, comfort and/or appearance to the outer cover, than textiles not including such elastomeric fibers.

Specific suitable examples for durable outer cover materials include jersey knits of blends of: rayon (93%) and spandex (7%) fibers; modal (94%) and spandex (6%) fibers; cotton and spandex fibers; and bamboo and spandex fibers. Materials that have stretch capability of equal to or greater than about 2× may be desired. Suitable examples of materials may have basis weights of about 0.09-0.15 gram/in.$^2$ per layer, or other basis weights.

Materials and stretch features as described in U.S. Published Applications Nos. 2008/0119813, 2008/0119814, 2008/0119815 and 2008/0119816 may be used in the construction and configuration of outer cover 20 or any portions thereof, such as the crotch region.

Durable outer cover materials may be selected to impart desired comfort, appearance and performance to outer cover 20. In some circumstances it may be desired to select durable outer cover materials which are sufficiently inexpensive to allow for disposal, if soiled extensively or damaged, with minimized issues of cost or conscience.

Semi-durable outer cover materials may include any natural or synthetic nonwoven web and/or film materials known in the diaper or pant arts. Semi-durable materials of which outer cover 20 may be constructed may include non-woven web materials of polypropylene and/or polyethylene fibers, polyester fibers, and any other synthetic fibers used to form non-woven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of outer cover 20.

Non-limiting examples of fibers, nonwovens and laminates of nonwovens and films that might be considered for use as semi-durable outer cover materials may be found in U.S. Pat. Nos. 7,223,818; 7,211,531; 7,060,149; 6,964,720; 6,905,987; 6,890,872; 6,884,494; 6,878,647; and 5,518,801; and U.S. Published Applications Nos. 2008/0319407; 2008/0045917; 2007/0293111; 2007/0287983; 2007/0287348; 2007/0249254; 2007/0203301; and 2005/0164587.

Semi-durable outer cover materials also may be selected to impart desired comfort, appearance and performance to outer cover 20. In some circumstances it also may be desired to select semi-durable outer cover materials which are sufficiently inexpensive to allow for disposal, if soiled extensively or damaged, with minimized issues of cost or conscience.

The outer cover also, or additionally, may include a laminated or substantially separate film layer, which may be elastic, to provide enhanced liquid penetration resistance and/or elastic properties. Elastic properties also can be added or enhanced via the addition of other materials to the outer cover in layer, band or strip fashion, including elastic strands, bands, scrims, and the like. A film layer may be laminated with a durable material or semi-durable material. A film layer may include an elastomer based on KRATON (a product of Kraton Polymers U.S., LLC, Houston, Tex.), or by way of further example, VISTAMAXX available from ExxonMobil Chemical Company, Houston, Tex.; FLEXAIRE, EXTRAFLEX or FABRIFLEX (products of Tredegar Film Products Corporation, Richmond, Va.), and various latex-free elastomeric sheets available from Fulflex Elastomerics Worldwide (Greenville, Tenn.).

Inclusion of an elastomeric material, either as a fibrous component of a cloth or nonwoven layer, or as a film layer, provides for improved stretchability and elasticity where it may be deemed useful to accommodate the wearer's anatomy and movements, such as over the wearer's buttocks and/or around the waist areas, and improved fit and comfort. Additionally, where a film layer may be included, it may impart additional liquid containment capability to the outer cover. A film layer may include a film that is substantially liquid impermeable, but vapor permeable, so as to provide breathability and reduce humidity within the outer cover while it is being worn, reducing chances for over-hydration of the skin where liquid containment capability is desired. A breathable film also may be provided by mechanically perforating or aperturing a film by various processes. Examples of such processes are described in co-pending U.S. application Ser. Nos. 12/366,825 and 12/534,353.

Referring to FIG. 2A, in one example outer surface 24 may be formed by a first layer of a durable or semi-durable material. The material selected may include fibers having hydrophobic properties, providing enhanced liquid containment attributes to such first layer. In another example, however, it may be desirable in some circumstances for the selected material to include hydrophilic fibers, or fibers treated to be hydrophilic, so as will cause the material to more readily absorb and/or transmit liquid therethrough. This may serve to provide supplemental absorbency within the outer cover for the event in which liquid exudates escape the insert, or to provide one way of communicating to the user that liquid exudates have escaped the insert. Additionally, in some circumstances it may be desirable that the material selected have soft tactile properties so as to have a pleasant feel that the user and/or wearer find attractive. The material also may be selected so as to have a desired appearance, including but not limited to coloration, sheen, texture, etc.

Outer cover 20 may be formed of a single layer of a durable or semi-durable material, or may have two or more layers in the front region 27 and/or rear region 28. Accordingly, referring to FIG. 2B, in another example inner surfaces 25 may be formed by a second layer of a durable or semi-durable material. The material selected may include fibers having hydrophobic properties, providing enhanced liquid containment attributes to the second layer. In another example, however, it may be desirable in some circumstances for the selected material to include hydrophilic fibers, or fibers treated to be hydrophilic. This may be desired in some circumstances to cause the material forming inner surfaces 25 to more readily absorb liquid, or transmit liquid therethrough. This may serve to provide supplemental absorbency within the outer cover for an event in which liquid exudates escape the insert, reducing the likelihood that the outer cover will leak. Alternatively, it may provide one way of communicating to the user that liquid exudates have escaped the insert, by causing wetness to be transmitted through to the outer cover outer layer such that wetness is visible on outer surfaces. Alternatively, it may serve to provide a layer that tends to draw moisture away from the skin, for a drier, more comfortable feel.

Additionally, in some circumstances it may be desirable that the material(s) selected for inner surfaces 25 have soft tactile properties so as to have a pleasant feel against the skin, particularly in areas where no portion of an insert is expected to be present between the outer cover and the wearer's skin.

In another example, the second layer of material may be formed of a textile material having enhanced elasticity, such as by inclusion of fibers of an elastomeric material (such as spandex). In another example, an intermediate film layer may be included, laminated or not laminated with another layer.

Forming the outer cover 20 of more than one layer, for example, two, or more, layers, as described above, may provide various benefits. A second layer (and any additional layers) may provide supplemental tensile strength in both the lateral and longitudinal directions across the outer cover 20. Additionally, a first layer may be selected for a first set of properties, and a second layer may be selected for a second set of properties. For example, material forming a first layer may be selected for having comparatively greater elasticity and a particular texture, color and/or other appearance-related properties, and material forming a second layer may be selected for having comparatively greater hydrophobicity, hydrophilicity and/or softness to the skin for purposes of an inner layer, the two layers in combination imparting a combination of desirable attributes to the outer cover. For example, the inner layer may be formed of material(s) and/or treated to be more hydrophilic so as to provide for absorbency and reduced chances of fluid runoff (leakage), while the outer layer may be formed of material(s) that are more hydrophobic, so as to, e.g., resist environmental soiling, or resist liquid transmission from the inner layer to the outer layer. Additionally, a plurality of layers may better serve to conceal bumps, corners, seams or other features of an insert, as compared with a single layer, for a smoother, more attractive appearance.

In addition to forming differing layers of differing materials, it may be desirable to form a single layer of differing materials, for example, differing materials in the respective front, crotch and/or rear regions of the outer cover. Such differing materials may be joined at a seam such as inner seam 40 and/or outer seam 41. For example, the material predominately forming the inner surface of rear region 28 may be selected primarily for its elasticity features, which may better serve to provide snug fit about wearer body contours and accommodate wearer movement (i.e., about the buttocks and hips). By comparison, the material predominately forming the inner surface of front region 27 and/or crotch region 26 might be selected primarily for its hydrophobicity or hydrophilicity, which may better serve to contain liquid exudates.

Layers or other elements of the outer cover may be joined to each other via any suitable mechanism, including, for example, adhesives, mechanical bonding, ultrasonic bonding, sewing, stitching, serging, edging, and the like.

Additionally or alternatively to the constructions and materials described above, the outer cover may be constructed and may include materials and features as described in co-pending U.S. application Ser. Nos. 12/687,412; 12/687,528; and 12/687,425, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on the same day hereof.

Elasticized Waistbands, Leg Bands

Referring again to FIGS. 1, 2A and 2B, front waist band portion 34, rear waist band portion 35, and leg band portions 36 are depicted. One or more of these band portions 34, 35, 36 may be formed of one or more strands or strips including an elastomeric material such as spandex or a blend of spandex and other fibers, enveloped by a nonwoven or textile material, which may include the edges of the material forming the inner and/or outer layers of outer cover 20, to form and elasticize the respective band portions. The elastic material may be affixed to or within an outer cover layer in a strained condition, or at zero applied strain. Textile material(s) enveloping the elastic strand(s) or strip(s) may be sewn around elastic strand(s) or strip(s) to hold them in place within the respective band portions. If the elastic material is strained prior to, and while, being enveloped and affixed to form these band portions during the manufacturing process, upon relaxation the enveloping material and adjacent outer cover material may be caused to gather and form ruffles 37 therealong, which constitute gathered outer cover material. This can serve to promote snug fit, wearer comfort and appearance. The band portion may be disposed along the edge of the outer cover, and in some circumstances it may be desired to have the band portion situated along substantially the entire length of the leg and/or waist openings so as to form bands that substantially or completely encircle the wearer's legs and/or waist while outer cover 20 is worn. The gathered material within ruffles 37 can serve to accommodate stretching of waist band portions 34, 35 and leg band portions 36. This arrangement including elasticized leg band portions 36 as described, not only may provide for better fit about the wearer's legs, but also may enable the outer cover 20, when formed of appropriately sized and shaped material, to form a pouch-like structure 75 in the crotch region (see FIG. 1) when worn, which may serve to provide space within the outer cover to accommodate the insert 50 (FIG. 3) and help hold it in place within outer cover 20, in a substantially laterally centered position within the crotch region. This may be deemed advantageous in examples in which an insert 50 is attached within outer cover 20 by fastener components only located proximate to the respective ends of insert 50, and not at any longitudinally intermediate locations, as described further below. Alternatively, or additionally, the elastic strands or strips in waist band portions 34, 35 and leg band portions 36 may be affixed within the outer cover only at or near their respective ends, e.g., within a pouch, tube or envelope structure formed of outer cover material—referred to herein as a "drawstring elastic". This will allow the elastic material and associated outer cover material to stretch and move freely and independently of each other, which may promote fit and comfort. A snug fit about the wearer's legs provided by such elasticized leg band portions 36 may serve to enhance containment capability of the wearable absorbent article.

One or more of waist band portions 34, 35 and leg band portions 36 may be elasticized in the manner described above, or by other mechanisms. For example, elasticized band/strip material such as that used to form elastic waistbands and leg bands or other banding features of conventional cloth underwear, briefs or other articles of clothing may be separately produced, and affixed to the materials forming outer cover 20 in any suitable manner, during the manufacture thereof.

In another example, one or more of waist band portions 34, 35 and leg band portions 36 may be formed of elastic material simply affixed about the leg opening and/or waist opening edges by use of adhesive and/or compression bonding. In another example, an elastic strip material may formed by affixing a plurality of strained elastomeric strands or strips to one or more strips of unstrained nonwoven web material, or film. When the resulting elastic strip material is allowed to relax, the unstrained material forms transverse rugosities that comprise gathered unstrained material, which will accommodate stretching of the elastic strip material. By affixing the elastic strip material at one or more of waist band portions 34, 35 and/or leg band portions 36, the elastic strip material may be used to form one or more of elasticized waist band portions 34, 35 and/or leg band portions 36.

Anchoring Bands

Outer cover 20 also may include an anchoring supplement such as anchoring band 38 disposed on or in the outer cover rear region 28 as indicated in FIGS. 2A, 2B. As suggested in FIGS. 2A and 2B, anchoring band 38 may be affixed along a layer, or disposed between layers, forming inner surfaces 25 and outer surfaces 24 of outer cover 20. Anchoring band 38 may include an elastomeric or elasticized strip or band of material, affixed to outer cover 20 at locations proximate to its rearward corners or proximate to fastening ears 29. Thus, anchoring band 38 may be partially or substantially force-decoupled from the other layer(s) of the outer cover along its lateral length from the layer(s) forming the inner and outer surfaces of outer cover 20, via attachment to the outer cover only by the ends of anchoring band 38, or only at a limited number of selected intermediate lateral locations along anchoring band 38. For example, anchoring band 38 might be attached to outer cover 20 only at the ends of anchoring band 38. In another example, anchoring band 38 might be attached to outer cover 20 only at the ends and at the lateral center of anchoring band 38. This substantially force-decoupled arrangement allows anchoring band 38 and surrounding portions of outer cover 20 to stretch and move substantially independently of one another, which may promote better fit and comfort. In another example, however, anchoring band 38 may be an elastic band, strip or strap laminated with or otherwise affixed to a layer of stretchable material forming either of or both the inner and outer surfaces of the outer cover, along substantially the entire length of anchoring band 38.

When strained laterally by application to the wearer, anchoring band 38 may serve to provide, or supplement, lateral tensile forces in the article about the wearer's waist, thereby tending to draw the waist opening snug, enhancing fit and enhancing securement of the wearable absorbent article about the wearer's waist. The elastic modulus of the anchoring band may be higher than the elastic modulus of the surrounding, adjacent, or coextensive outer cover materials.

An anchoring band, or system of one or more anchoring band members, may have any additional features described in, for example, co-pending U.S. patent application Ser. Nos. 11/810,741; 11/810,708; 12/101,476; 12/028,317; 11/810,745; 11/810,742; 11/810,734; 11/810,779; 11/810,715; 11/810,733; 11/810,736; 11/810,777; and 11/599,862; 11/810,901 and 11/599,851; 11/899,812; 12/204,844; 12/204,849; 12/204,854; 12/204,858; and 12/204,864; 11/899,810; 11/899,656; and 11/899,811; 11/899,812; 12/204,844; 12/204,849; 12/204,854; 12/204,858; and 12/204,864; and co-pending U.S. application Ser. Nos. 12/687,437; 12/687,554; and 12/687,444, entitled, respectively, "REUSABLE WEARABLE ABSORBENT ARTICLES WITH ANCHORING SYSTEMS," "REUSABLE WEARABLE ABSORBENT ARTICLES WITH ANCHORING SUBSYSTEMS," and "REUSABLE OUTER COVERS FOR WEARABLE ABSORBENT ARTICLES," by Donald C. Roe, filed on the same day hereof.

In another example, instead of, or in addition to, being oriented substantially laterally as suggested by the depicted location of anchoring band 38 in FIGS. 2A and 2B, one or more members forming anchoring bands may be oriented diagonally between the longitudinal and lateral directions. For example, as suggested in FIG. 2A, a pair of diagonal anchoring bands 38a may have respective waist ends thereof affixed at a location area proximate to corners of the outer cover and/or fastening ears 29, and respectively extend toward both the lateral and longitudinal center of outer cover 20, as suggested in FIG. 2A. The respective center ends of bands 38a may be affixed to the outer cover at locations proximate the lateral center of the outer cover as suggested in FIG. 2A, and bands 38a may be either force-decoupled or force-coupled to the outer cover along the lengths of bands 38a, as described above. In an example where an insert is connected to an anchoring band for additional longitudinal support as described further below, diagonal anchoring bands such as diagonal anchoring bands 38a may serve to provide supplementary longitudinal tension along outer cover 20, providing supplemental longitudinal support therewithin.

Outer Cover Asymmetry

In order to enhance and/or maximize fit, wearer comfort and appearance of the outer cover 20, it may be desirable to fashion outer cover 20 so as to accommodate anatomical contours and body movements of the intended wearer. For example, as suggested by FIGS. 2A and 2B, outer cover 20 may have differing shape and/or greater material surface area in the rear region 28 than in the front region 27. Human anatomy in the lower torso/hip/thigh region is asymmetric about the lateral plane of the body, i.e., the geometry of the front of the human body is different than that of the back. To provide for better fit and comfort, the outer cover geometry and functionality, including stretch properties, may be adapted accordingly. Differing shape and/or greater material surface area in the rear region may serve to better cover the buttocks through movements of the wearer (including sitting and/or bending forward at the hips), while lesser material surface area in the front region may serve to avoid material bunching and/or an ill-fitting appearance, particularly when the wearer is in positions including sitting and/or bending forward at the hips. As a result, the outer cover may be asymmetric in shape or surface area across outer cover lateral axis 45.

For purposes of this description, when used with respect to an outer cover, "asymmetric" and "asymmetry" mean that features, geometry (e.g., shape), materials and/or construction on one side of outer cover lateral axis 45 differ substantially in some respect from those on the other side of outer cover lateral axis 45. Such asymmetric construction results from having various features of outer cover 20 designed to accommodate the body features and functions of the intended wearer as they differ front-to-rear, to enhance containment/absorbency performance, comfort, fit and/or appearance of the wearable absorbent article, and/or to economize on use of materials. "Asymmetric" and "asymmetry" do not refer to differences across the outer cover lateral axis that are attributable to features that may be included on an outer cover only for purposes of: purely cosmetic coloration or surface decoration; fastening an insert (such as fastener components described herein); bundling, folding, storing or carrying the outer cover; indicia for orienting an insert within an outer cover or vice versa (such as orientation indicia described herein), or for other purposes substantially unrelated to the body features and functions of the intended wearer as they differ front-to-rear, to affect performance, comfort, fit and/or physical appearance of the wearable absorbent article, and/or to economize on use of materials.

Other asymmetries across outer cover lateral axis 45 may be present as well. For example, as suggested by FIGS. 2A and 2B, relatively localized outer cover fastener components 30 may be respectively disposed on fastening ears 29, while a relatively laterally extended receiving fastener component 31 may be disposed on outer cover front region 27, for purposes of waist opening adjustability as explained above. Fastening ears 29 may form lateral extensions from rear region 28 that are not present in kind on front region 27. These are examples of differences that create functional and structural asymmetries of the outer cover across outer cover lateral axis 45. Because an absorbent article of the type described herein is usually changed while the wearer is substantially facing the user, such arrangement enhances user convenience by locating these fastening and waist opening adjustability features at the wearer's front abdominal region, facing the user.

In another example of asymmetry, materials of differing composition, construction and/or properties may predominately form forward region 27 as compared with rearward region 28. For example, the material(s) forming rear region 28 may be selected for enhanced stretch/elastic properties, as compared with material(s) forming front region 27. In this example, material(s) with enhanced stretch/elastic properties may serve to better accommodate, stretch and contract over contours of the buttocks, and accommodate body movements such as sitting and bending forward at the hips, thereby providing better coverage and fit.

In still another example of asymmetry, outer cover 20 may have structures such as elastic bands, anchoring bands and/or other members which differ between front region 27 and rear region 28.

In still other examples of asymmetry, the materials forming outer cover 20 may have, or be imparted with, differing levels of hydrophilicity and/or hydrophobicity, differing levels of breathability, differing coefficients of friction, and/or other differing functional attributes in the front versus the rear regions.

It will be appreciated, therefore, that outer cover asymmetry across outer cover lateral axis 45 is a result of design and construction of the outer cover so as to have only one front region and only one rear region, i.e., the front and rear regions are not interchangeable, if the fit, comfort, performance and appearance of outer cover 20 are to be optimal.

Additional Outer Cover, Front Waist Region and Landing Zone Details

Figure 14:
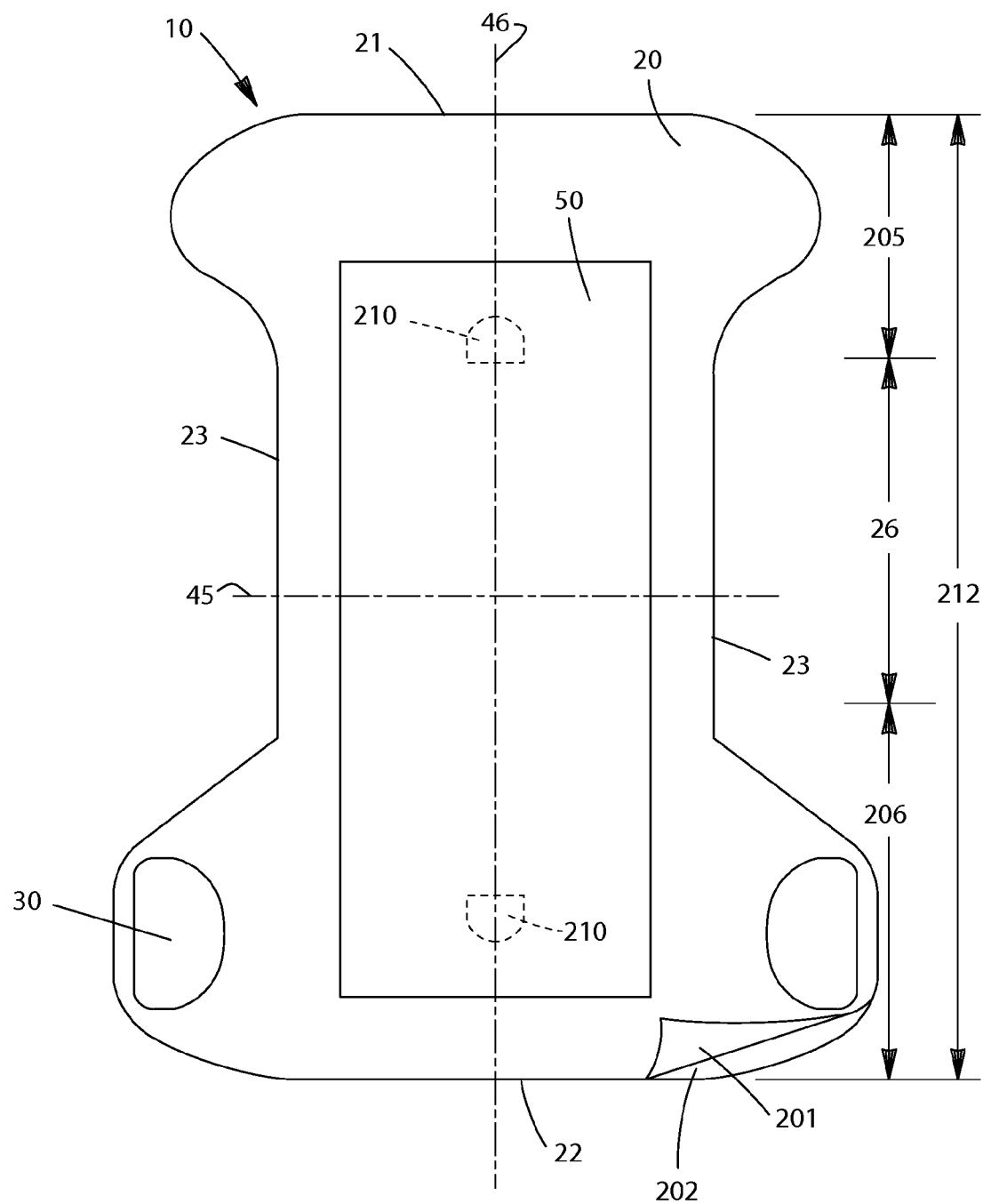
FIG. 14 is a plan view of an exemplary outer cover for an absorbent article.
Figure 15:
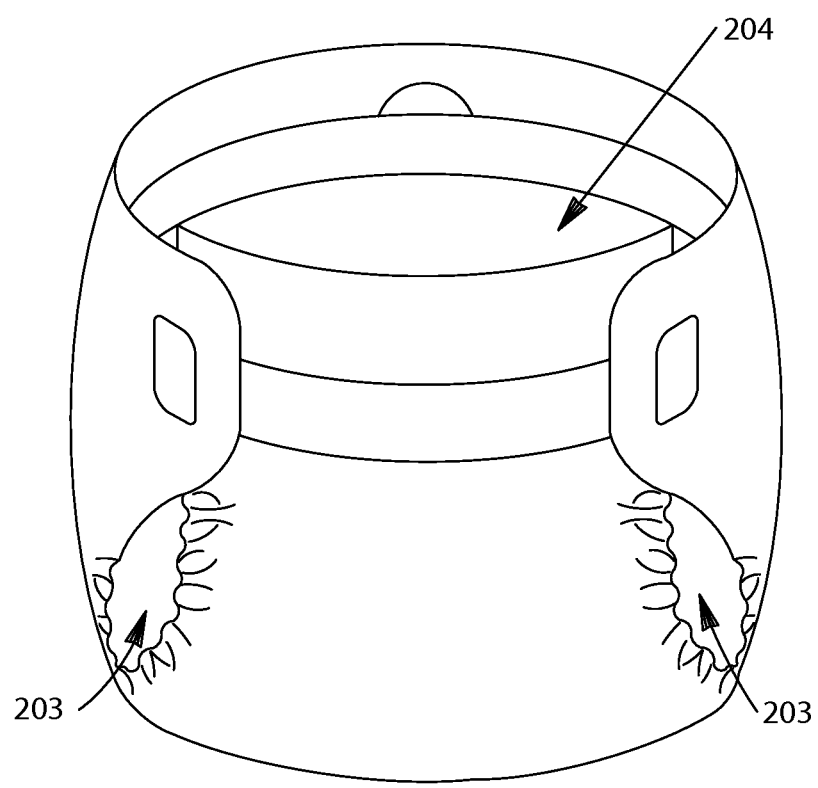
FIG. 15 is a perspective view of an exemplary outer cover for an absorbent article, configured for wearing.

Referring now to FIGS. 14-18C, absorbent article 10 will have a inner, wearer-facing surface. When fitted to a wearer as intended, the wearer-facing surface will be the surface of absorbent article 10 nearest the wearer. In FIG. 14, the wearer-facing surface of outer cover 20 and absorbent insert 50 are visible. At the bottom, right-hand corner of FIG. 14, outer cover 20 is shown as having two distinct layers, inner layer 201 and outer layer 202. Inner layer 201 is shown separated from outer layer 202 and folded over, so that the wearer-facing surface of outer layer 202 and the garment-facing layer of inner layer 201 are visible. FIG. 15 shows absorbent article 10 configured for wearing, with the garment-facing surface most visible, and a portion of the wearer-facing surface visible through leg openings 203 and waist opening 204.

Front waist region 205, or back waist region 206, or both, may comprise outer cover fastener components 30. FIG. 14 shows outer cover fastener components 30 on the wearer-facing side of back waist region 206. Absorbent article 10 may be applied to a wearer by placing back waist region 206 under the wearer's buttocks, pulling front waist region 205 up between the legs to the ventral hips or torso (depending upon where the waist of the diaper is intended to sit on the wearer), and fastening a fastener on the wearer-facing surface of back waist region 206 to the garment-facing surface of front waist region 205. It is also possible, for example, to fasten a fastener on the garment-facing surface of back waist region 206 to the wearer-facing surface of front waist region 205. Thus, it should be understood that the discussion of the fastening system, and in particular, the landing zone, also contemplates embodiments wherein the components are reversed in this manner.

Figure 16:
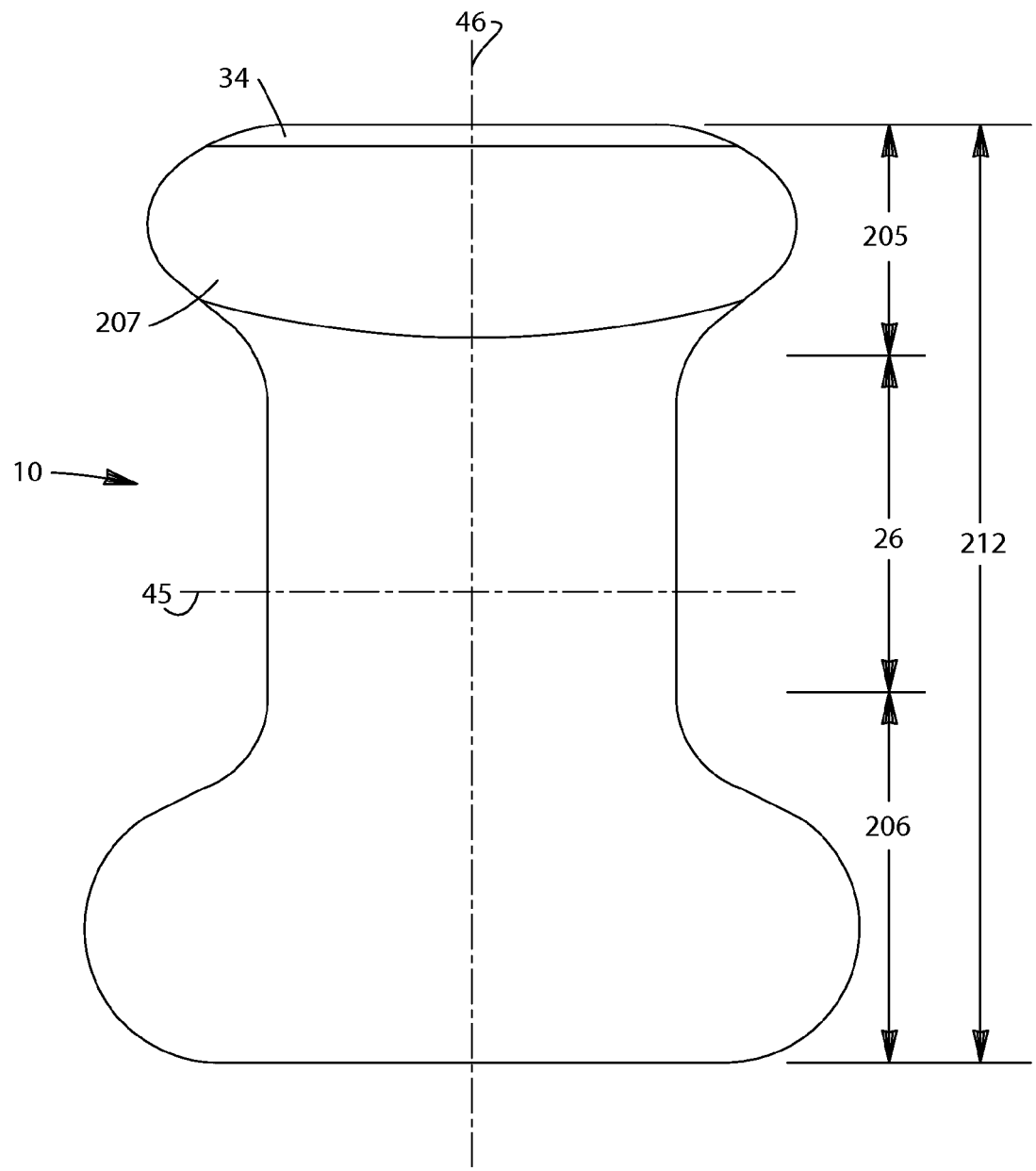
FIG. 16 is a plan view of an exemplary absorbent article.

FIG. 16 shows the garment-facing surface of outer cover 20. The garment-facing surface of outer cover 20 may have a landing zone 207 in front waist region 205. Landing zone 207 may be configured to join back waist region 206 to front waist region 205 via outer cover fastener components 30. Outer cover fastener components 30 may comprise mechanical fasteners, such as snaps, buttons or buttonholes, ties, zippers, hook-and-eye, hook-and-loop, and the like. Outer cover fastener components 30 may comprise chemical fasteners such as pressure sensitive adhesives, adhesives, selective adhesives, or cohesives. Landing zone 207 may comprise a surface or implement engageably cooperative with outer cover fastener components 30 to effect fastening therebetween. For example, if outer cover fastener components 30 are mechanical, landing zone 207 may comprise snaps, buttons or buttonholes, ties, zippers, hooks, eyes, or loops. If article 10 is reusable, it may be desirable to provide outer cover fastener components 30 and landing zone 207 as a system which is resistant to soiling. For example, some adhesive systems may be rendered ineffective if exposed to powders or oils, as may be used by some caregivers when changing a diaper. A reusable article 10 may, instead, comprise a fastening system which is either mechanical or which uses chemical fasteners which are resistant to soiling or can be regenerated after soiling, such as some selective adhesives or cohesive systems. Exemplary chemical fasteners which might be useful in a reusable article 10 are described in U.S. Pat. No. 7,722,592 to Dalal, et al.; U.S. Pat. No. 5,908,695 to Kobe, et al.; and U.S. Patent Application Publication No. 2008/0058753 to Dalal, each of which is hereby incorporated by reference in its entirety. For a reusable article 10, it may be desirable to use a fastening system which can undergo at least 5, or at least 10, or at least 15 laundry cycles in a washing machine with no noticeable degradation in fastening performance. More preferably, it may be desired that the fastening performance of a reusable outer cover does not substantially degrade after 30, 40, or even 50 washings, as may be demanded for an outer cover that will remain useful for a year or more of regular use. In this context, "substantial degradation" of fastening performance means a loss of more than 50% of original resistance to separation, after two fastening components are brought into intended fastening engagement under circumstances and then urged to separate by a separating force applied along the same direction as that of application of the engaging force.

Figure 17:
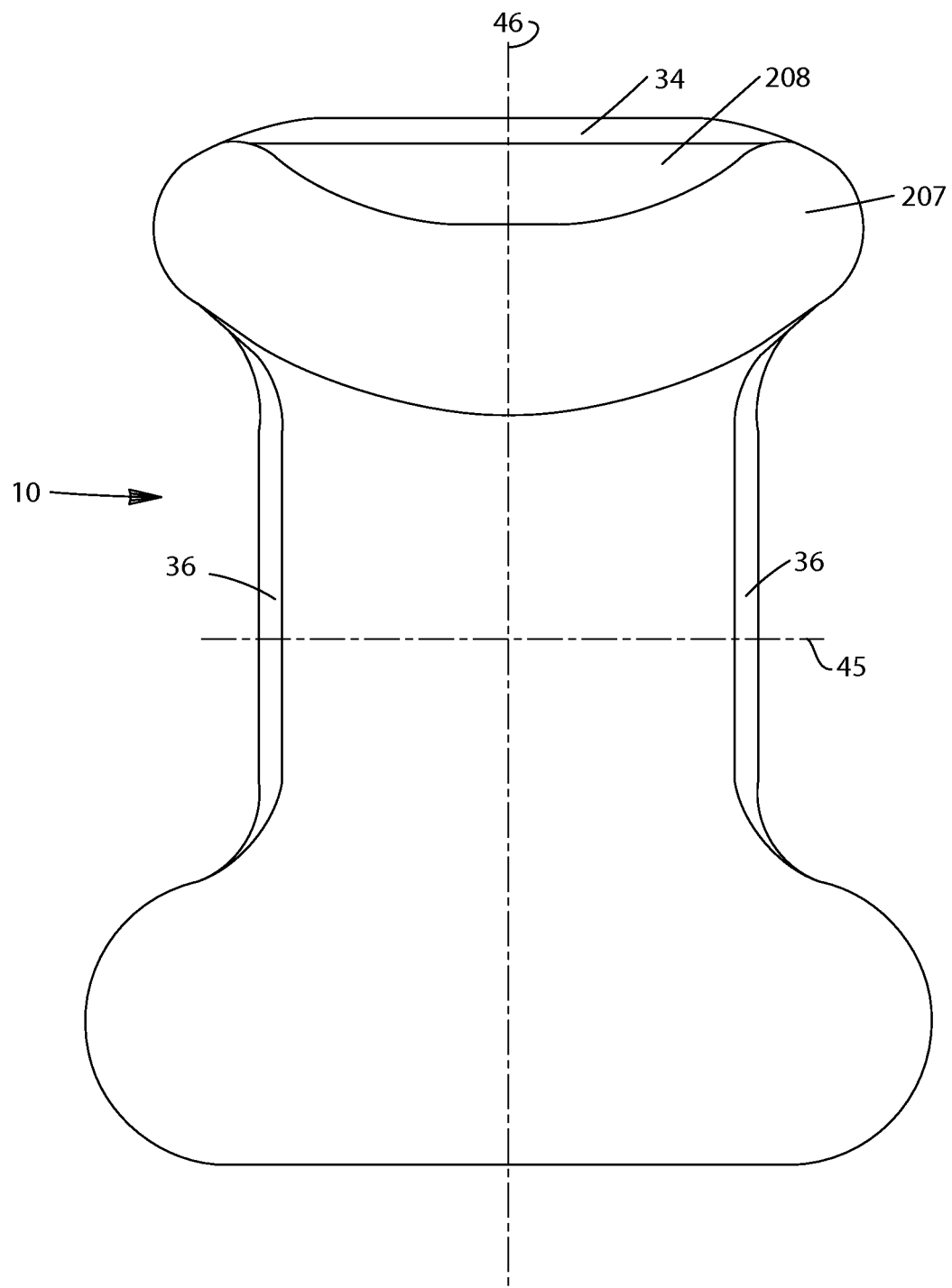
FIG. 17 is a plan view of an exemplary absorbent article.

In FIG. 16, landing zone 207 is shown as having laterally extending edges substantially parallel to the laterally waist edges of article 10. In some embodiments, as shown in FIG. 17, landing zone 207 may, instead, be chevron- or boomerang-shaped. In such embodiments, the outer perimeter of article 10 may follow the outline of landing zone 207, or, as shown in FIG. 17, an added material 208 may be used to raise the waist of article 10 above the longitudinal edge of landing zone 207. Added material 208 may, for example, be the same material as inner layer 201 or outer layer 202. In some embodiments, inner layer 201 and/or outer layer 202 may extend continuously under landing zone 207, such that inner layer 201 and/or outer layer 202 is continuous through front waist region 205 and at least a portion of crotch region 26.

It may be desirable to impart some bending stiffness to the article, particularly the front region, and more particularly the landing zone. If the front region of the article is unduly pliable or "floppy," this may provide opportunity for the material to become difficult to control and maintain in a suitable position during application of the article to a wearer, and it may also tend to bunch up while the article is being worn. Thus, adding some bending stiffness to the front region, and particularly the landing zone, helps facilitate handling and control during application of the article, and also helps prevent the material of the front region from bunching. Although some bending stiffness may be desirable, however, too much bending stiffness may create a source of discomfort for the wearer. It is possible to construct a landing zone having a desired bending stiffness.

For example, the outer cover of a two-piece article may comprise hook-and-loop fasteners, where the landing zone 207 comprises the loops portion of the fastening system. By selecting from among loops materials having differing backings, or having different thicknesses, loops heights, or other features contributing to bending stiffness of the material, it is possible to achieve a desired bending stiffness in front waist region 205 relying only on the stiffness of loops material to form landing zone 207. In one example, a suitable loops material may be a knitted or woven polyester fleece fabric having a basis weight of 8 ounces/square yard. The material may be napped on one or both sides so as to impart compressible loft and thickness, thereby contributing to bending stiffness, while still having a compressible and soft feel. Such fabric may serve as a suitable landing zone material for use as the loops component of a hook-and-loop fastening system. The side bearing the greater degree of napping may be disposed on the inside and be expected to add compressible thickness to the landing zone structure, while the side relatively less or no napping, may form the outside (garment-facing) surface of the landing zone and provide suitable fastenable engageability with the hooks component of a hook-and-loop fastening system.

It also may be desirable in some circumstances to provide a supplementary stiffening member 209, which may be disposed between the material forming landing zone 207 and the material forming inner layer 201. A separate stiffening member 209 allows for the modification of the properties of landing zone 207 without changing the properties of the fastening system itself. For example, longer or taller loops in a hook-and-loop fastening system may change the force required to unfasten the system, perhaps to an undesirable degree. A stiffening layer may be included to add bending stiffness to the landing zone and mitigate undesirable effects.

In some embodiments, the stiffening member 209 may comprise a layer of polymeric foam or other compressible material. A foam stiffening member 209 may provide sufficient stiffness to landing zone 207 to make article 10 easier to handle, apply, and/or change without making landing zone 207 so stiff that it is uncomfortable to a wearer. In particular, unlike many loops material backings, stiffening member 209 may be compressible, so that front waist region 205 feels "soft" without being unmanageably floppy, and so that the stiffening member 209 may compress into itself if pressed against the wearer, thereby making front waist region 205 more accommodating to different wearer sizes and shapes. In some embodiments, the stiffening member 209 and landing zone 207 may be selected so that front waist region 205, when assembled, is compressible in a Z-direction (i.e., a direction orthogonal to both the lateral axis 45 and longitudinal axis 46 of article 10) by 20-50%, or 25-40%, or 25-35%, under 0.4 psi of perpendicular, vertical pressure.

With regard to bending stiffness, the materials forming landing zone 207 (e.g., loops material), without a supplementary stiffening member 209, may be selected so that the landing zone has a bending stiffness, at one or more particular locations, between 60 and 120 N/m, more preferably between 70 and 110 N/m, and even more preferably between 80 and 100 N/m, when measured using the Landing Zone Bending Stiffness Test herein. Where more thickness and compressibility is desired, a stiffening member may be provided behind the loops material and help to impart a bending stiffness between 100 and 300 N/m. As noted, a foam layer may be used to form the stiffening layer.

It may be desirable that such bending stiffness exist at at least one, but more preferably, all three locations described in the Landing Zone Bending Stiffness Test. This strikes a balance between a landing zone that is conveniently stiff to enable the caregiver to apply the article and quickly and easily engage fasteners to the landing zone, and avoidance of bunching of material in the front region, while still providing a landing zone with desirable softness, pliability and comfort for the wearer.

It may also be desired that lateral stretchability of the front waist region be controlled. Some limited stretchability may be desired to provide yield, comfort and perceived softness of the front waist region, but at the same time, excessive stretch proximate the locations of fastening in the front waist region may contribute to unacceptably loose fit and sagging of the article when worn, particularly when loaded with the weight of the wearer's exudates. Accordingly, it may be desired to control stretchability by selection of materials having limited stretchability. In some embodiments, the material(s) forming the stiffening member 209 and landing zone 207 may be selected so that the portion of the front waist region 205 bearing the landing zone 207, when assembled, has limited stretch. For example, the landing zone portion of the front waist region 205 may be constructed so as to exhibit lateral strain of 60% or less under 100 N of lateral force, or even 50% or less, or even 45% or less, when measured according to the Landing Zone Lateral Strain Test herein. For purposes of perceived softness and comfort, however, it may be desirable that the landing zone portion of the front waist region 205 be constructed so as to exhibit lateral strain of 20% or more under 100 N of lateral force, when measured according to the Landing Zone Lateral Strain Test herein. Thus, it may be desired that the landing zone portion of the front waist region 205 exhibit lateral strain between 20% and 60% at a lateral force of 100 N, or between 20% and 50%, or even between 20% and 45%.

Absorbent foams are known in the art, however, stiffening member 209 need not be absorbent in all circumstances. In some embodiments, for example, if stiffening member 209 is layered against a hydrophobic inner layer 201, there may be little or no exposure of stiffening member 209 to exudates discharged into absorbent article 10. In some embodiments, for example, if no inner layer 201 is used, or if inner layer 201 is liquid pervious, stiffening member 209 may be absorbent and may contribute to the overall absorptive capacity of absorbent article 10 and/or may be useful in preventing leaks of exudates out of absorbent article 10 along the edges of front waist region 205. Exemplary absorbent foams are described, for example, in U.S. Pat. No. 5,331,015 to DesMarais, et al., U.S. Pat. No. 5,387,207 to Dyer, et al., and U.S. Pat. No. 6,083,211 to DesMarais, et al.

In some embodiments, a foam or other compressible stiffening member 209 may be quieter than a typical fastener backing. That is, a foam stiffening member 209 may not crinkle or make other noises when manipulated. Thus, a foam stiffening member 209 may make article 10 seem softer and more comforting because of its acoustic properties. Of course, a stiffening member 209 could be used with other conventional stiffening materials for providing body to articles for wearing, such as interfacings and fusible materials (for example, as available from Pellon Consumer Products LLC of St. Petersburg, Fla., USA), either as an additional layer used with a compressible stiffening member 209 as described herein or in other portions of article 10 which do not comprise a compressible stiffening member 209 as described herein.

In some embodiments, front waist region 205 may be defined by landing zone 207. Or, conversely, landing zone 207 may extend across substantially all of front waist region 205. This provides for maximum convenience for the caregiver in applying the article to a wearer (i.e., a large target area for attachment), maximum adjustability in sizing of the waistband circumference, and also provides a way to impart stiffness to the front waist region, which may desired as explained below. In this context, "substantially all of front waist region 205" means that landing zone 207 is coextensive with front waist region 205 with the possible exception of trim, seam allowances, and the like, but in no instance less than 85% coextensive with front waist region 205 as assembled. In some embodiments, landing zone 207 may be no less than 90% coextensive with front waist region 205, or no less than 95% coextensive with front waist region 205, as assembled. Trim includes elastics, waistbands, and any decoration such as lace, ribbon, or other decorative embellishments which may be attached to front waist region 205. In some embodiments, landing zone 207 may extend laterally across substantially all of front waist region 205 or longitudinally across substantially all of front waist region 205, but not be entirely coextensive with front waist region 205. The stiffening member 209, if present, may be coextensive or substantially coextensive with landing zone 207. In some embodiments, the stiffening member 209 could be present beyond front waist region 205, such as extending into or placed in discrete portions of crotch region 26 and/or back waist region 206. For example, a stiffening member 209 could extend through the longitudinal length of article 10, or in the ears of back waist region 206 near or coextensive with outer cover fastener components 30, or substantially coextensive with back waist region 206. In some embodiments, the stiffening member 209 is excluded from crotch region 26 to reduce bulk in crotch region 26. In some embodiments, stiffening member 209 is excluded from at least 50%, or at least 70%, or at least 75%, or at least 80%, or at least 85%, or at least 90%, of the longitudinal length 212 of absorbent article 10. Stiffening member 209 may be excluded from a portion of longitudinal length 212 of absorbent article 10 corresponding at least in part to crotch region 26. Stiffening member 209 may be disposed only in front waist region 205.

Front waist region 205 may include a waist band portion 34. The waist band portion 34 may comprise an unreinforced span or loop of woven or nonwoven material attached at the outboard longitudinal edge of front waist region 205. The waist band portion 34 may be elastic. That is, it may tend to produce a return force when extended by no more than 150% of its length in the assembled article 10. The material from which the waist band portion 34 is made may be inherently elastic. For example, the waist band portion 34 may comprise spandex or other elastic materials. In some embodiments, the waist band portion 34 may incorporate elastic elements. For example, waist band portion 34 may be a loop of material enclosing an elastic component, or may be sewn or glued to an elastic member, such as an elastic yarn, string, ribbon, or etc. Waist band portion 34 may help to fold or, particularly if it is elastic, pull, the outboard longitudinal edge of landing zone 207 against the body of a wearer during use. Pulling the edge of article 10 to the wearer may help prevent leaks by holding fluids or body exudates in until they can be absorbed by article 10, in circumstances where the total capacity of article 10 is not exceeded, but the rate of liquid acquisition has been exceeded, as when exudates are discharged from the body in a relatively large volume over a relatively short period of time.

Aside from any elastic elements, waist band portion 34 may be unreinforced. That is, waist band portion 34 may comprise no overlying or underlying layers, and no stiffening member 209 or stiffening material. An unreinforced waist band portion 34 may be useful in preventing leaks and/or creating a pleasing aesthetic fit for article 10. However, unreinforced waist band portion 34 may be prone to roll-over, which may inhibit the utility and/or aesthetics of waist band portion 34. It may be desirable for waist band portion 34 to extend along less than 90%, or less than 80%, or less than 75%, but more than 50% or more than 60% of the longitudinally outboard edge of front waist region 205, centered along the longitudinal axis 46 of article 10. Waist band portion 34 may be less prone to roll-over or fold over on itself if it does not extend to the longitudinally-extending lateral edges 26 of front waist region 205.

As described above, front waist region 205 may comprise an inner layer 201 and an outer layer 202. Inner layer 201 and outer layer 202 may have different properties. For example, in a disposable article 10, inner layer 201 may be a liquid-pervious topsheet, and outer layer 202 may be a liquid-impermeable backsheet. As another example, in an article that is reusable or has a reusable outer cover, inner layer 201 may be hydrophobic, to contain liquids or other exudates and hold them near an absorbent insert 50 until they are absorbed, and outer layer 202 may be absorptive, to help absorb and limit the spread of any exudates that have escaped article 10. Other variations of the properties of inner layer 201 and outer layer 202, as well as variations of the properties within inner layer 201 or outer layer 202, are described, for example, in U.S. Patent Application Publication No. 2010/0179503 to Roe, et al.

Inner layer 201 and outer layer 202 may also be structured differently than one another. For example, inner layer 201 may be a continuous inner liner extending from front waist edge 21 of front waist region 205 to rear waist edge 22 of back waist region 206. In some embodiments, inner layer 201 extends at least under front waist region 205, and more specifically under landing zone 207 and the stiffening member 209, if present. In some embodiments, outer layer 202 is joined to landing zone 207 along the inboard-most longitudinal edge of landing zone 207 and/or the stiffening member 209, if present. That is, outer layer 202 may end at the beginning of landing zone 207, such that outer layer 202 does not extend underneath or over landing zone 207 and/or the stiffening member 209, if present. Similarly, inner layer 201 could be joined to the inboard-most longitudinal edge of landing zone 207 and/or the stiffening member 209, if present. In one exemplary embodiment, from wearer-facing side to garment-facing side, front waist region 205 of article 10 comprises an inner layer 201, a foam stiffening member 209, and landing zone 207. Outer layer 202 may be joined to the foam stiffening member 209, to landing zone 207, or to both the foam stiffening member 209 and landing zone 207. In some embodiments, outer layer 202 is not joined to inner layer 201 along the inboard-most longitudinal edge of front waist region 205 (but may be joined to inner layer 201 along the remainder of the perimeter of front waist region 205, or portions thereof). In some embodiments, outer layer 202 is joined to inner layer 201 along the inboard-most longitudinal edge of front waist region 205.

In some embodiments, crotch region 26 may comprise leg band portions 36. Leg band portions 36 may extend along at least a portion of longitudinally extending, leg opening edges 23 in crotch region 26. Leg band portions 36 may extend longitudinally into back waist region 206. In some embodiments, leg band portions 36 do not extend into front waist region 205. Leg band portions 36 may be elastic or inelastic, and may have structure similar to the variants described above with regard to waist band portion 34. In some embodiments, leg band portions 36 and waist band portion 34 are the same in terms of materials and general construction, although they may differ in terms of length, width, and contour because of their different position within the structure of article 10. In some embodiments, leg band portions 36 and waist band portion 34 are made of different materials.

Two or more outer cover fastener components 30 may be joined to a wearer-facing surface of back waist region 206. Outer cover fastener components 30 may be attachably engageable with landing zone 207. For example, if landing zone 207 comprises loops material, outer cover fastener components 30 may comprise hooks, to form a hook-and-loop fastener. One or more fasteners may be joined to the wearer-facing surface of inner layer 201, at attachment point(s) 210. The fasteners of the wearer-facing surface of outer cover 20, which might be used, for example, to attach an absorbent insert 50, can be selected independently of outer cover fastener components 30. In some embodiments, the outer cover fastener components 30 on the wearer-facing surface of back waist region 206 are sized or shaped differently than the fasteners at attachment point(s) 210, to avoid confusion about where to attach the different fasteners.

Attachment point(s) 210 may be disposed on the wearer-facing surface of inner layer 201. In some embodiments, one or more attachment point(s) 210 underlie landing zone 207. In some embodiments, one or more attachment point(s) 210 are joined directly to landing zone 207 and/or stiffening member 209. In embodiments wherein an absorbent insert 50 is attached to attachment point(s) 210, joining attachment point(s) 210 to directly landing zone 207 and/or stiffening member 209 may help secure and support absorbent insert 50 within the structure. For example, if attachment point(s) 210 are disposed on inner layer 201, and inner layer 201 is joined to landing zone 207 only along the perimeter of front waist region 205 or only along a portion of the perimeter of front waist region 205, inner layer 201, and, therefore, attachment point(s) 210 may be able to move relative to the wearer and/or landing zone 207 during use. Accordingly, absorbent insert 50 may also be able to move relative to the wearer and/or landing zone 207. Such relative movement may create fit, comfort or exudates containment deficiencies. By directly securing attachment point(s) 210 directly to landing zone 207 and/or stiffening member 209, however, absorbent insert 50 may be indirectly attached to landing zone 207 and/or stiffening member 209. This may reduce movement of absorbent insert 50 during use, which may help reduce or prevent leakage of exudates through gaps between absorbent insert 50 and the wearer's body. In some embodiments, securing attachment point(s) 210 directly to landing zone 207 and/or stiffening member 209 may help prevent sagging or displacement or pulling or sagging inward (toward the wearer) of the waist of absorbent article 10 during use. Especially, but not exclusively, when absorbent insert 50 is loaded with exudates, joining attachment point(s) 210 to landing zone 207 and/or stiffening member 209 may be helpful in holding the heavier, loaded insert 22 in its intended position. In some embodiments, attachment point(s) 210 are attached to landing zone 207 and/or stiffening member 209 within the perimeter of front waist region 205. In some embodiments, attachment point(s) 210 are tacked (e.g., by stitching or other attachment mechanism) directly to landing zone 207 and/or stiffening member 209 at one or more discrete points. In some embodiments, attachment point(s) 210 are joined to landing zone 207 and/or stiffening member 209 along the perimeter of attachment point(s) 210 (as by sewing attachment point(s) 210 to landing zone 207 and/or stiffening member 209 around at least a portion of the perimeter of attachment point(s) 210). In some embodiments, attachment point(s) 210 are joined to landing zone 207 and/or stiffening member 209 indirectly (e.g., no single stitch or seam in absorbent article 10 may include material from both attachment point(s) 210 and landing zone 207 and/or stiffening member 209). For example, attachment point(s) 210 may be joined to inner layer 201, and inner layer 201 may be attached to landing zone 207 and/or stiffening member 209 at one or more discrete points within the perimeter of the landing zone. As another example, inner layer 201 may be attached directly to landing zone 207 and/or stiffening member 209 adjacent at least a portion of the perimeter of attachment point(s) 210 within the perimeter of front waist region 205 (e.g., a seam may join inner layer 201 and landing zone 207 and/or stiffening member 209, the seam encircling an attachment point 210).

Figure 18A:
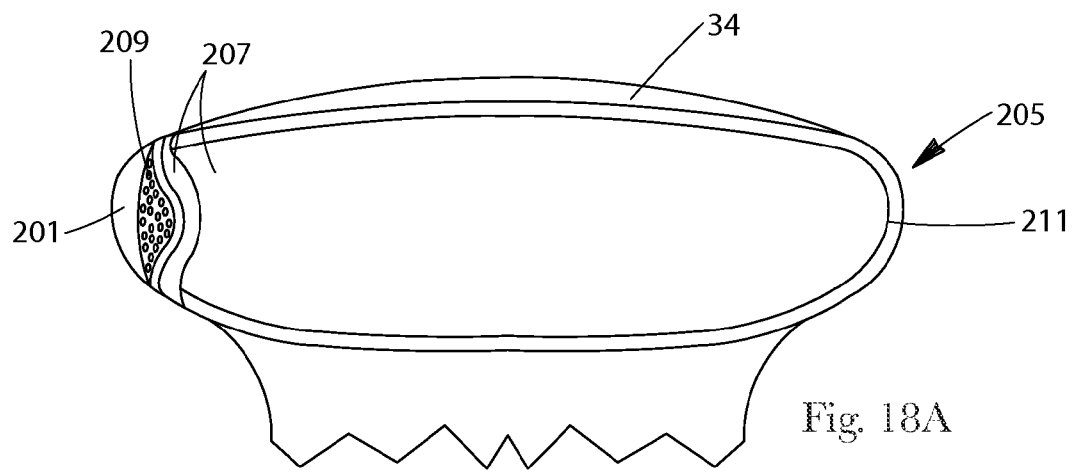
FIG. 18A is a plan view of a front portion of an exemplary absorbent article.
Figure 18B:
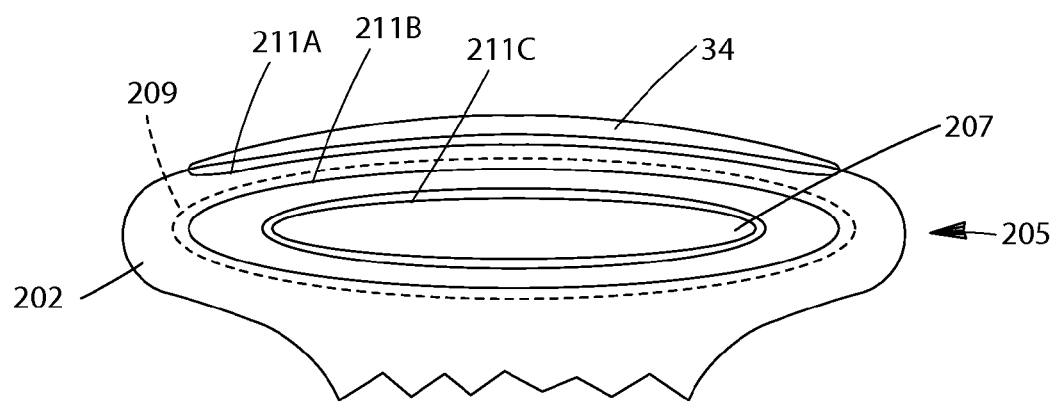
FIG. 18B is a plan view of a front portion of an alternative absorbent article.
Figure 18C:
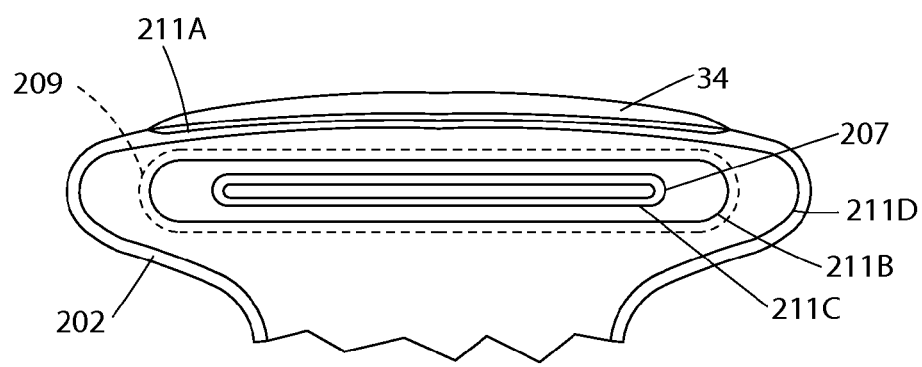
FIG. 18C is a plan view of a front portion of an alternative absorbent article.

With regard to construction, it may be advantageous to provide an inner layer 201 (if included), stiffening member 209, and landing zone 207 which are co-extensive, laterally and longitudinally, across substantially all of front waist region 205. As shown in FIG. 18A, if the two or three layers of front waist region 205 are substantially co-extensive, they can be joined with a single continuous seam 211. If waist band portion 34 is used, it can be joined to landing zone 207 prior to forming front waist region 205, or waist band portion 34 can be joined to landing zone 207 with the same single seam 211. In FIG. 18A, seam 211 is shown as visible from the garment-facing surface of article 10, as would be the case if seam 211 was stitched, but seam 211 could also be made using techniques, such as adhesive joining, such that seam 211 might not be visible from the garment-facing surface of article 10. In contrast, as shown in FIG. 18B, if the layers of front waist region 205 are not substantially coextensive, it may be necessary to form multiple seams, 211A, 211B, and 211C to join waist band portion 34, stiffening member 209, and landing zone 207 to front waist region 205 of article 10. FIG. 18B shows waist band portion 34, stiffening member 209, and landing zone 207 joined to outer layer 202, however, waist band portion 34, stiffening member 209, and landing zone 207 could be joined to inner layer 201, or to both inner layer 201 and outer layer 202. These alternate embodiments might require additional seams. For example, as shown in FIG. 18C, seam 211D may be used to join inner layer 201 (not shown in FIG. 18C) to outer layer 202, in addition to other seams to join the waist band portion 34, stiffening member 209, and landing zone 207 to article 10. Of course, it is also possible to provide landing zone 207 and/or stiffening member 209 as discrete parts, which could further increase the number of seams required to assemble article 10. Even when automated, each seam adds cost and complexity to the assembly process. This could slow the assembly process, and is also associated with more opportunities for defects, making it more likely that any individual article will need to be reworked, discounted, or discarded due to seaming problems (e.g., improper spacing or positioning of the seam or one or more layers to be attached, poor attachment to all desired layers, etc.).

In some embodiments, stiffening member 209 may be laminated to landing zone 207. For example, stiffening member 209 may be joined to landing zone 207 as by glue or hot melt adhesives, or by ultrasonic welding, or coextrusion, or other processes known in the art. If stiffening member 209 and landing zone 207 are formed separately and laminated to one another, they may be attached substantially across the entire surface area of stiffening member 209, or may be joined at discrete points or along discrete "lines". A "line", as of adhesive or as of a pattern formed by joining by compression, heat, ultrasonic welding, etc., may be straight or curvilinear, or may be patterned, and may be continuous or discontinuous. For example, a stiffening member 209 and landing zone 207 may be joined along "lines" that are spirals, dotted lines, stripes, or dots, or in lines that are laid down in overlapping spirals, cross-hatch, random, or other patterns. In some embodiments, laminating stiffening member 209 to landing zone 207 may facilitate the use of a stronger fastening system for joining back waist region 206 of absorbent article 10 to front waist region 205. A "stronger" fastening system, which requires more force to unfasten, may help anchor absorbent article 10 on the wearer, or prevent "pop-offs," where one or more of outer cover fastener components 30 unintentionally detach from landing zone 207. In some embodiments, particularly when using some combinations of hooks and loops as the fastening system, it may be easier to detach outer cover fastener components 30 from landing zone 207 if landing zone 207 is laminated to stiffening member 209 than if landing zone 207 is unreinforced, or is joined to stiffening member 209 only along the perimeter or a portion of the perimeter of front waist region 205. One exemplary material useful as a laminated stiffening member 209 and landing zone 207 is sold under the trademark VELTEX, and comprises nylon fabric with a polyester foam core and nylon tricot backing.

In some embodiments, stiffening member 209 and landing zone 207 are substantially coextensive, and waist band portion 34 is joined to both stiffening member 209 and landing zone 207. As described above, stiffening member 209 and landing zone 207 may be selected such that front waist region 205 has a particular bending stiffness. Front waist region 205 may also have a particular caliper. For example, front waist region 205 may have a caliper between 2-6 mm, or 3-5 mm, or 4-6 mm at 0.1 p.s.i. It has been observed that an unreinforced waist band portion 34 may be less inclined to roll- or fold-over on itself when attached along less than 90%, or less than 80%, or less than 75%, but more than 50% or more than 60% of the longitudinally outboard edge of front waist region 205, centered along the longitudinal axis 46 of article 10, in particular when front waist region 205 has the described bending stiffness and/or caliper. The compressibility of front waist region 205 does not appear to be critical to this decrease in waistband roll- or fold-over. Decreasing waistband roll- or fold-over may be aesthetically pleasing, in that article 10 may seem to fit better, or even appear to be more comfortable, if waist band portion 34 does not roll- or fold-over the front of landing zone 207 during use. Decreasing waistband roll- or fold-over may also improve the leakage protection of article 10, as exudates are less like to escape article 10 along the front waist edge 21 during use if waist band portion 34 lies against the wearer's body, forming an additional barrier to the movement of exudates out of article 10 along the front waist edge 21. In some embodiments, waist band portion 34 does not need to be elasticized or taut against the wearer to provide some improvement in this regard.

This description makes reference to outer cover 20, the structure of which, as shown in FIG. 14, is more likely to be seen in a reusable article 10 than in a disposable article 10. However, it should be understood that the structure and properties of outer cover 20 apply to a disposable diaper. By way of comparison, outer layer 202 of outer cover 20 may correspond to the garment-facing surface of a backsheet in a disposable diaper, and inner layer 201 of outer cover 20 may correspond to the wearer-facing surface of a backsheet in a disposable diaper, or, in some embodiments, outer layer 202 and inner layer 201 may correspond to a backsheet and a separate layer within article 10, respectively.

Examples of Possible Absorbent Insert Details

Examples of features of an absorbent insert 50 will be described with reference to FIGS. 3, 4 and 5A-F.

As noted above, FIG. 3 depicts a disposable absorbent insert 50 that may form an inner component of a wearable absorbent article as described herein, shown in perspective view as it might appear in a free-standing, relaxed state, apart from an outer cover. FIG. 4 depicts an example of an insert 50 shown stretched out and laid flat (against elastic-induced contraction to a position similar to that shown in FIG. 3), body-facing surfaces facing the viewer. FIGS. 5A-5F depict cross sections of an insert 50 as indicated in FIG. 4, in various possible examples.

Insert 50 may have a topsheet 51 and backsheet 52 forming an envelope-like enclosure for absorbent core materials such as those described further below. Topsheet 51 and backsheet 52 may be affixed together along longitudinal seams 64, and along lateral seams 69. Insert 50 also may have longitudinal standing cuffs 53 affixed therealong.

Topsheet

Topsheet 51 may be formed of a liquid-permeable nonwoven web material. It may be desired that material forming topsheet 51 is compliant, soft-feeling, and non-irritating to the wearer's skin. It may be desired that at least a portion of topsheet 51 may be liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If topsheet 51 includes fibers, the fibers may be spunbond, carded, wet-laid, meltblown, hydroentangled, or otherwise processed as is known in the art.

One suitable material comprising a nonwoven web of staple-length polypropylene fibers is manufactured by Veratec, Inc., a Division of International Paper Company, of Walpole, Mass. under the designation P-8. Additional suitable materials comprising formed films are described in U.S. Pat. Nos. 3,929,135; 4,324,246; 4,342,314; 4,463,045; and 5,006,394. Other suitable topsheets 30 may be made in accordance with U.S. Pat. Nos. 4,609,518 and 4,629,643. Suitable examples of formed and/or apertured films may include products produced by The Procter & Gamble Company of Cincinnati, Ohio as DRI-WEAVE, and by Tredegar Corporation, based in Richmond, Va., as FRESHFEEL. Suitable topsheet materials also may include laminates of films and nonwoven webs produced by Tredegar as COMFORTFEEL, COMFORTQUILT, SOFTQUILT and COMFORTAIRE.

In some circumstances it may be desired that at least a portion of topsheet 51 is made of a hydrophobic material or is treated to be hydrophobic in order to isolate the wearer's skin from liquids contained in absorbent core 71. If topsheet 51 is generally made of a hydrophobic material, it may be desired that at least a portion of the upper surface of topsheet 51 is treated to be hydrophilic so that liquids will transfer through the topsheet more rapidly. Topsheet 51 can be rendered hydrophilic by treating it with a surfactant or by incorporating a surfactant into the topsheet. Suitable methods for treating topsheet 51 with a surfactant include spraying the topsheet material with the surfactant and/or immersing the material into the surfactant. A more detailed discussion of such a treatment and hydrophilicity is contained in U.S. Pat. Nos. 4,988,344 and 4,988,345. A more detailed discussion of some suitable methods for incorporating a surfactant in the topsheet can be found in U.S. Statutory Invention Registration No. H1670. In another example, however, topsheet 51 may include an apertured web or film which is hydrophobic. This may be accomplished by foregoing the hydrophilizing treatment step from the production process and/or applying a hydrophobic treatment to the topsheet material, such as a polytetraflouroethylene compound like SCOTCHGUARD or a hydrophobic lotion composition, as described below. In such examples, it may be desired that the apertures be large enough to allow the penetration of aqueous fluids like urine without significant resistance otherwise attributable to hydrophobicity. It may also be desired that the apertures have sufficient effective open area and/or aperture size to allow the penetration of low-viscosity fecal material. Examples of topsheets meeting these requirements are described in U.S. Pat. Nos. 5,342,338; 6,414,215; and 6,010,491.

Any portion of topsheet 51 may be coated with a lotion or skin care composition as is known in the art. Examples of suitable lotions include those described in U.S. Pat. Nos. 5,607,760; 5,609,587; 5,635,191; 5,643,588; 5,968,025 and 6,716,441. The lotion may function alone or in combination with another agent as the hydrophobizing treatment described above.

Topsheet 51 may also include or be treated with antibacterial agents, some examples of which are disclosed in U.S. application Ser. No. 08/212,441, published as U.S. Statutory Invention Registration H1732.

Topsheet 51, backsheet 52 or any portion of the topsheet or backsheet may be embossed and/or matte finished to provide a more cloth-like appearance.

Topsheet 51 may be fully or partially elasticized or may be foreshortened so as to provide a void space between topsheet 51 and core 71. Exemplary structures including elasticized or foreshortened topsheets are described in more detail in U.S. Pat. Nos. 4,892,536; 4,990,147; 5,037,416; and 5,269,775.

Backsheet

Backsheet 52 is generally that outer liner portion of insert 50 forming the garment-facing surface thereof, and prevents the exudates absorbed and contained within insert 50 from wicking through and soiling the outer cover. In some circumstances it may be desired that backsheet 52 is substantially impervious to liquids.

Backsheet 52 may be formed of a film, a nonwoven, or a laminate of a film and a nonwoven. Backsheet 52 may be formed of a substantially liquid-impermeable laminate or composite of film and non-woven web. Backsheet 52 may be formed of a substantially liquid impermeable nonwoven web, or laminate of nonwoven web and substantially liquid impermeable film, so as to contain and isolate liquid exudates from the outer cover, outer clothing and/or environment of the wearer. At the same time, backsheet 52 may be vapor permeable to provide for breathability of the insert and the wearable absorbent article, reducing humidity in the areas between the insert and the wearer's body, and helping reduce the likelihood of skin irritation and/or rashes that may result from over-hydration of the skin.

The material forming backsheet 52 may include a thin plastic film such as a thermoplastic film having a thickness of about 0.012 mm (0.5 mil) to about 0.051 mm (2.0 mils). Suitable backsheet materials also may be breathable materials which permit vapors to escape while still preventing liquid from passing therethrough. Suitable examples may include those manufactured by Tredegar Corporation, based in Richmond, Va., and sold under the trade names CPC2, X15306, X10962 and X10964 film. Other examples may include microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some additional examples may include breathable composite materials as described in PCT Application No. WO 95/16746; and U.S. Pat. Nos. 5,938,648; 5,865,823; and 5,571,096. In other examples, backsheet 52 may comprise elastomeric films, foams, strands, or combinations of these or other suitable materials with nonwovens or synthetic films.

In certain embodiments, the backsheet may have a water vapor transmission rate (WVTR) of greater than about 2000 $g/24\ h/m^2$, greater than about 3000 $g/24\ h/m^2$, greater than about 5000 $g/24\ h/m^2$, greater than about 6000 $g/24\ h/m^2$, greater than about 7000 $g/24\ h/m^2$, greater than about 8000 $g/24\ h/m^2$, greater than about 9000 $g/24\ h/m^2$, greater than about 10000 $g/24\ h/m^2$, greater than about 11000 $g/24\ h/m^2$, greater than about 12000 $g/24\ h/m^2$, greater than about 15000 $g/24\ h/m^2$, measured according to WSP 70.5 (08) at 37.8° C. and 60% Relative Humidity. A higher WVTR may be desired in this particular application, since the insert backsheet 52 will not form the outer surface of the wearable article, as a conventional disposable diaper backsheet would, but rather, will be covered by the one or more layers of the outer cover material(s)—which themselves may act in some circumstances to reduce WVTR of the composite structure.

Backsheet 52 may be joined to topsheet 51, absorbent core 71 or any other element of insert 50 by any suitable attachment mechanism known in the art. For example, the attachment mechanism may include a continuous line or layer of adhesive, a patterned layer of adhesive, or an array of separate lines, spirals, or spots of adhesive. One example of an attachment mechanism comprises an open pattern network of filaments of adhesive as disclosed in U.S. Pat. No. 4,573,986. Other suitable attachment mechanisms include several lines of adhesive filaments which are swirled into a spiral pattern, as is illustrated by the apparatus and methods shown in U.S. Pat. Nos. 3,911,173; 4,785,996; and 4,842,666. Adhesives which have been found to be satisfactory are manufactured by H. B. Fuller Company of St. Paul, Minn. and marketed as HL-1620 and HL-1358-XZP. Alternatively, the attachment mechanism may comprise heat bonds, pressure bonds, ultrasonic bonds, dynamic mechanical bonds, or any other suitable attachment mechanisms or combinations of these attachment mechanisms known in the art.

It will be appreciated that the outer cover described above can be constructed of materials and construction so as to bear and sustain a majority of the structural loading generally imposed upon a disposable diaper, by stretching and accommodation of the wearer's anatomical features and body movements, and by absorption, swelling and added weight resulting from the wearer's exudations of waste. Thus, lesser requirements for structural strength of an insert might be present with use of such an outer cover, as compared with strength required of inside components of a disposable diaper. Therefore, an article such as described herein may include a disposable absorbent insert manufactured from materials that are different from those ordinarily used in the manufacture of disposable diapers, such as petroleum-derived materials, e.g., polyethylene and polypropylene. For example, a disposable absorbent insert having one or more of a topsheet, backsheet, standing cuffs and/or other components formed of products of wood, cotton, flax (linen), hemp, bamboo, or other cellulose fibers (e.g., paper), in addition to the materials identified above, is contemplated. If resistance to aqueous liquid penetration or substantial liquid impermeability is desired, e.g., for a backsheet and/or standing cuffs, a material formed of ordinarily hydrophilic fibers such as paper may be coated or impregnated with a hydrophobic material, such as a skin-compatible oil or wax, to impart the desired resistance to aqueous liquid penetration. Each of the materials forming the insert may be selected so as to be dispersible in water or an aqueous solution, flushable, biodegradable and/or compostable (preferably to an agriculturally usable humus or soil amendment).

Absorbent Core

Referring to FIGS. 5A-F, insert 50 may have an absorbent core 71 within the envelope-like structure formed by topsheet 51 and backsheet 52. Absorbent core 71 may comprise any absorbent material which is generally compressible, conformable, non-irritating to the wearer's skin, and capable of absorbing and retaining liquids such as urine and other certain body exudates. Absorbent core 71 may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Absorbent core 71 may include liquid acquisition/distribution material 65, and storage material 66. Generally, acquisition/distribution material 65 may have comparatively rapid absorption and wicking properties, but also may have limited absorption capacity. Conversely, generally, storage material 66 may have comparatively slower absorption and wicking properties, but also may have greater absorption capacity. Thus, acquisition/distribution material 65 may serve to rapidly absorb and distribute gushes of liquid such as urine, while storage material 66, having greater absorption capacity, may serve to absorb such liquid from the acquisition/distribution material and store it for the time needed until the insert may be replaced.

Absorbent core 71 may be manufactured in a wide variety of sizes and shapes (e.g., rectangular, hourglass, "T"-shaped, etc.). The configuration and construction of absorbent core 71 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Examples of absorbent structures for use as absorbent core 71 may include those described in U.S. Pat. Nos. 4,610,678; 4,673,402; 4,834,735; 4,888,231; 5,137,537; 5,147,345; 5,342,338; 5,260,345; 5,387,207; and 5,625,222.

To reduce the overall size and/or thickness of the absorbent core, and thereby improve wearer comfort and reduce the volume of disposable waste created by a soiled insert, it may be desired to construct an absorbent core using the lowest volumes of core materials possible within performance constraints. Toward this end, examples of suitable materials and constructions for a suitable absorbent core are described in, but are not limited to, copending U.S. application Ser. Nos. 12/141,122; 12/141,124; 12/141,126; 12/141,128; 12/141,130; 12/141,132; 12/141,134; 12/141,141; 12/141,143; and 12/141,146. These applications generally describe absorbent core constructions that minimize or eliminate the need for and inclusion of airfelt or other forms of cellulose fiber in combination with particles of superabsorbent polymer (hereinafter, "substantially airfelt-free cores"). Airfelt and other cellulose fiber have been used as absorbent fillers in absorbent cores of disposable diapers. Such fiber possesses absorbent properties and imparts some absorption capacity to an absorbent core, but also is included to provide a structural matrix to hold dispersed particles of superabsorbent polymer and/or absorbent gelling material. While inclusion of such particles enhances absorption capacity, keeping such particles suitably dispersed may be important to prevent the particles from "gel-blocking" in use as they swell with absorbed liquid, causing loss of absorption capacity. The inclusion of airfelt or other cellulose fiber as a matrix for superabsorbent particles can serve to reduce or prevent gel-blocking. However, it also imparts bulk to an absorbent core, even before absorption of any liquids.

Figure 5A:
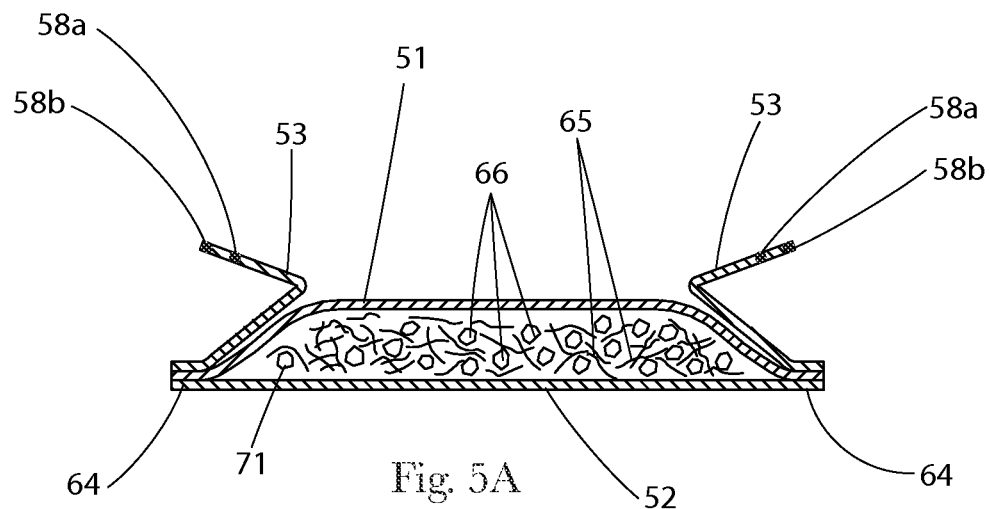
FIG. 5A is a cross sectional view of an example of an insert such as shown in FIG. 4, taken at line 5A-5A in FIG. 4.
Figure 5B:
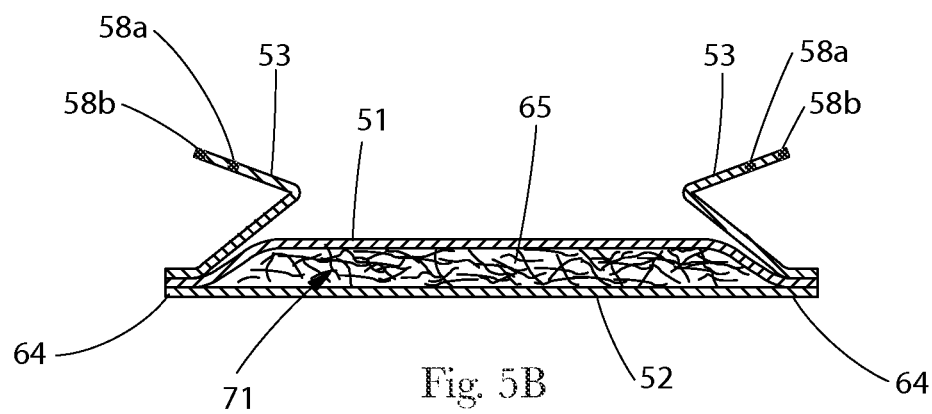
FIG. 5B is a cross sectional view of an example of an insert such as shown in FIG. 4, taken along line 5B-5B in FIG. 4.
Figure 5C:
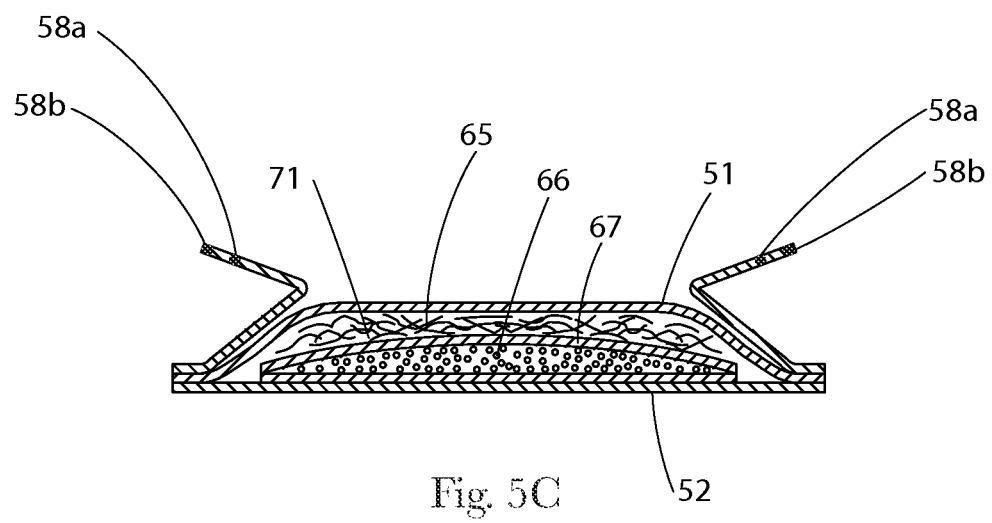
FIG. 5C is a cross sectional view of another example of an insert such as shown in FIG. 4, taken along line 5C-5C in FIG. 4.
Figure 5D:
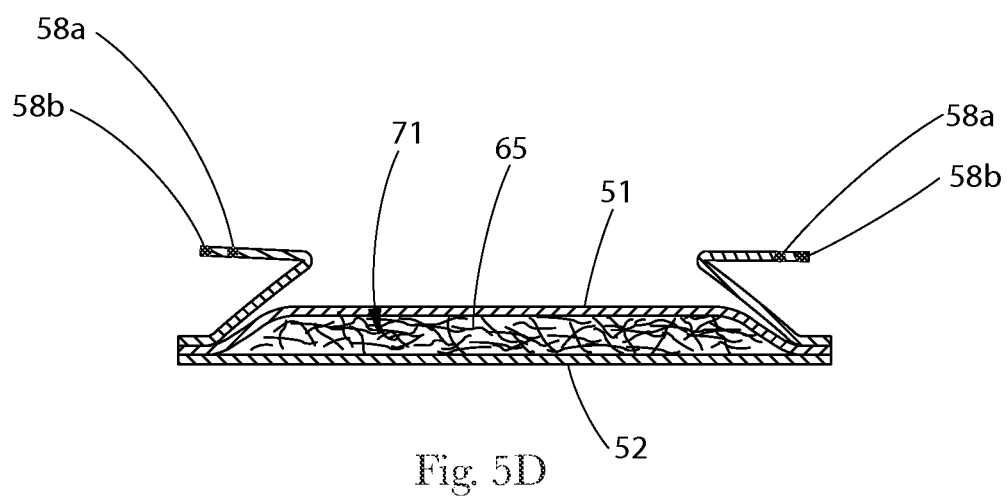
FIG. 5D is a cross sectional view of another example of an insert such as shown in FIG. 4, taken along line 5D-5D in FIG. 4.
Figure 5E:
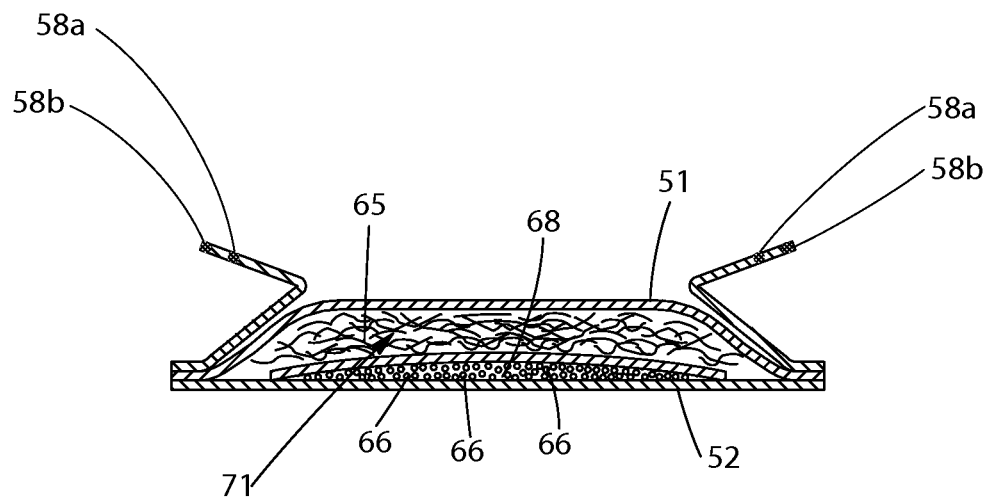
FIG. 5E is a cross sectional view of another example of an insert such as shown in FIG. 4, taken along line 5E-5E in FIG. 4.

In accordance with the disclosures in the co-pending applications identified immediately above, referring to the examples depicted in FIGS. 5C and 5E herein, an absorbent core 71 having a portion that is substantially airfelt-free may be disposed between the topsheet 51 and the backsheet 52. The core 71 may include a layer formed at least in part of a substrate, distributed absorbent particles 66 of a superabsorbent polymer or absorbent gelling material, and a thermoplastic adhesive composition capturing the distributed absorbent particles 66 and adhering to at least portions of the substrate, thereby immobilizing the absorbent particles 66 on or proximate to, and relative to, the substrate.

Features of an outer cover 20 as described herein provide for a wearable absorbent article that has a relatively improved, garment-like (or underwear-like) fit, comfort and appearance (as an outer garment or under other clothes), as compared with many types of wholly disposable diapers currently available. If an outer cover 20 having such attributes is used with an insert 50 having an absorbent core 71 incorporating substantial amounts of airfelt or other cellulose fiber, the improved, garment-like fit, comfort and appearance provided by the outer cover 20 may be compromised by the bulkiness of the insert. In order to better preserve some or most of the improved, garment-like fit, comfort and appearance of the outer cover 20, therefore, it may be desirable to construct absorbent core 71 of insert 50 with features as described in one or more of patent applications cited immediately above, which provide for a relatively thin absorbent core.

In addition to providing an absorbent core having reduced bulk, the substantially airfelt-free core may generally be more flexible than an absorbent core containing substantial amounts of airfelt or other cellulose fiber. This enhanced flexibility may enable the core and the associated insert to better conform about the wearer's body when in use, providing for improved comfort and less bulky appearance of the wearable article 10.

Additionally, by reducing or eliminating airfelt or other cellulosic fiber material, the substantially airfelt-free core reduces the amount of materials consumed in manufacturing, reduces the amount of space (and in some circumstances, weight) per unit which must be packaged and shipped, conserving resources in that regard, and reduces the amount of materials and bulk which must be disposed of in connection with disposing of a used/soiled insert.

Sublayer

Insert 50 may also include a sublayer disposed between topsheet 51 and backsheet 52. The sublayer may be any material or structure capable of accepting, storing or immobilizing bodily exudates. Thus, the sublayer may include a single material or a number of materials operatively associated with each other. Further, the sublayer may be integral with another element of insert 50 or may be one or more separate elements joined directly or indirectly with one or more elements of insert 50. Further, the sublayer may include a structure that is separate from the core 71 or may include or be part of at least a portion of the core 71.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One example of a sublayer includes a mechanical fastening loop landing element, having an uncompressed thickness of about 1.5 millimeters available as XPL-7124 from the 3M Corporation of Minneapolis, Minn. Another example includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Standing Cuffs

Insert 50 also may have a pair of longitudinal standing cuffs 53 attached partially or entirely along the length thereof. Suitable longitudinal standing cuffs (in various published examples identified as "leg cuffs", "barrier cuffs" "gasketing cuffs," etc., may be formed of materials and construction such as described in, but not limited to, U.S. Pat. Nos. 6,786,895; 6,420,627; 5,911,713; 5,906,603; 5,769,838; 5,624,425; 5,021,051 and 4,597,760; and copending U.S. Published Application No. 2007/0239130 and U.S. application Ser. No. 11/195,272. As shown in FIG. 3, standing cuffs 53 may have one or more strands or strips of cuff elastics 58a, 58b disposed longitudinally therealong. If such cuff elastics 58a, 58b are pre-strained prior to being affixed to the web material forming standing cuffs 53, resulting longitudinal tensile forces therealong will cause the web material forming standing cuffs 53 to gather as shown, and cause the cuffs to extend from the body of the insert (upwardly relative to FIG. 3), or causing them to "stand". This feature causes standing cuffs 53 to form a gasketing structure along the wearer's body when the article including insert 50 is worn, longitudinally on either side of the anatomical features where waste is exuded. Thus, standing cuffs 53 may serve to enhance the exudate containment capability of insert 50 and, and as a result, of the wearable absorbent article. As with backsheet 52, standing cuffs 53 may be formed of a substantially liquid impermeable web so as to contain and isolate liquid exudates from the outer cover, outer clothing and environment of the wearer. At the same time, standing cuffs 53 may be vapor permeable to provide for breathability of the insert and the wearable absorbent article, reducing humidity in the areas between the insert and the wearer's body, and helping reduce the likelihood of skin irritation and/or rashes that may result from over-hydration of the skin.

In another example, the material forming standing cuffs 53 may be integral with the material forming backsheet 52, such as described in, by way of non-limiting example, copending U.S. Published App. No. 2007/0239130. In this particular example, referring to and relative to the view in FIG. 3, a continuous piece of material may form one standing cuff 53, wrap beneath the insert to form backsheet 52, and wrap up the other side to form the other standing cuff 53. This example of a wraparound construction may provide improved liquid containment capability to insert 50, by eliminating seams along the outer liquid-containing surfaces that include standing cuffs 53 and backsheet 52. Another example of this construction is depicted and described in U.S. Pat. No. 4,808,178.

In some circumstances, however, manufacturing and/or economic constraints may discourage such construction, or else, it may be desirable for the materials forming standing cuffs 53 and backsheet 52 to have differing properties. For example, in some applications it may not be deemed necessary for standing cuffs 53 to be substantially liquid impervious, if they are otherwise formed of a nonwoven web material comprising closely situated hydrophobic fibers, which may still tend to repel and contain fluid, but may be generally more breathable than substantially liquid impervious laminates including films. In this event, improved strength and liquid containment attributes can still be imparted by having the material forming standing cuffs 53 wrap only partially beneath the lower longitudinal corners of the insert, and affixed at seams beneath the insert, rather than at its outermost lower corners as suggested by FIG. 3. One example of this construction is depicted and described in U.S. application Ser. No. 11/158,563, and in particular, FIG. 13 therein and associated descriptive text.

Insert Asymmetry

Referring to FIG. 4, insert 50 will have an insert lateral axis 70 that equally divides its longitudinal length. Insert 50 may have a structure that is asymmetric across insert lateral axis 70. For purposes of this description, with used with respect to an insert, "asymmetric" and "asymmetry" mean that features, geometry (e.g., shape), materials and/or construction on one side of insert lateral axis 70 differ substantially in some respect from those on the other side of insert lateral axis 70. Such asymmetric construction results from having various features of insert 50 designed to accommodate the body features and functions of the intended wearer (i.e., body contours, excretory and eliminatory functions) as they differ front-to-rear, to enhance containment/absorbency performance, comfort, fit and/or appearance of the wearable absorbent article, to economize on use of materials and/or to reduce volume of disposable waste. "Asymmetric" and "asymmetry" do not refer to differences across the insert lateral axis that are attributable to features that may be included on an insert only for purposes of: purely cosmetic coloration or surface decoration; fastening to an outer cover (such as fastener components described herein); user grasping of the insert (such as a grasping structure described herein); as indicia for orienting an insert within an outer cover (such as orientation indicia described herein); or for other purposes substantially unrelated to the body features and functions of the intended wearer as they differ front-to-rear, to affect performance, comfort, fit and/or physical appearance of the wearable absorbent article, to economize on use of materials and/or to reduce volume of disposable waste.

As one example, topsheet 51 may one or more have apertures 63 therethrough, predominately in the crotch and/or rearward region 55 as suggested in FIG. 4. Apertures 63 can permit liquid or low viscosity fecal material to penetrate topsheet 51 and reach absorbent materials in absorbent core 71 more rapidly than would occur without such apertures, enhancing liquid feces absorption and containment capability of insert 50.

In another example, a feces management feature may be disposed in the rear of the article, including one or more pockets, spacers, low viscosity feces management elements, openings in suspended elasticized topsheets, and similar features, for example, as described in copending U.S. application Ser. Nos. 11/224,779, 11/786,890 and 11/894,087. Thus, topsheet 51 may comprise one or more larger apertures in the rear region to provide for unrestricted or comparatively less restricted movement of solid or higher viscosity waste therethrough. The size of an aperture may be important in achieving the desired fecal waste encapsulation performance. If the aperture is too small, the waste may not pass through the aperture, either due to poor alignment of the exudation point and the aperture location, or due to fecal masses having a size greater than the aperture. If the aperture is too large, however, the area of skin that may be exposed to "rewet" from the contained waste matter is increased. An aperture may have an area of between about 10 cm$^2$ and about 50 cm$^2$. In some circumstances it may be desired that an aperture has an area of between about 15 cm$^2$ and 35 cm$^2$.

An insert may have asymmetry in its absorbent core (absorbent core asymmetry). Absorbent core asymmetry may result from arrangement of materials and features within the absorbent core to locate particular materials and features of the absorbent core where they are most needed and/or most effective, in accordance with features and functions of wearer anatomy as they differ front-to-rear.

For example, all or a portion of the rearward region 55 of insert 50 may include acquisition/distribution material 71 but less or no storage material 66 as compared with forward region 54, as may be seen by comparison of FIGS. 5A and 5B, 5C and 5D, and 5E and 5F, respectively. By this particular absorbent core asymmetry, storage material 66 may be located predominately in the front of the wearable absorbent article when worn. This may provide a predominate proportion of the insert's urine storage capacity closer to the urine exudation point of the wearer to reduce the likelihood of leakage, and remove potentially uncomfortable and/or unsightly size and bulk from between the wearer's legs or the wearer's backside area, particularly relevant when storage material 66 becomes swollen with absorbed liquid. Additionally, this particular asymmetry provides for economization of the amount of storage material 66 used, by locating it in only a portion of the insert rather than substantially along the entire insert. The liquid storage capacity of the forward region of the absorbent core may be greater than that of the rearward region of the absorbent core as measured by the Teabag Centrifuge Capacity test disclosed in U.S. Pat. No. 6,278,037. The liquid storage capacity of the forward region of the absorbent core may be at least about 10%, 20%, 50%, or even 100% or more greater than that of the rearward region. With such an arrangement, acquisition/distribution material 65 located in both forward and rearward regions 54, 55 can serve to acquire and move liquid (usually, urine) to the storage material 66 located predominately in the forward region 54. Alternatively, or additionally, the area and/or basis weight of the acquisition system or component materials in the forward region of the insert may be at least about 10%, 20%, 50%, or even 100% or more greater than that of the rearward region. Alternatively, or additionally, the surface area, cross-sectional area and/or lateral width of absorbent core 71 may be greater in the forward region 54 as compared with the rearward region 55. For example, the surface area, cross-sectional area and/or lateral width of absorbent core 71 may be greater in the forward region 54 as compared with the rearward region 55, to accommodate a greater proportion of the acquisition/distribution and/or storage material present in the forward region of the absorbent core.

Figure 5F:
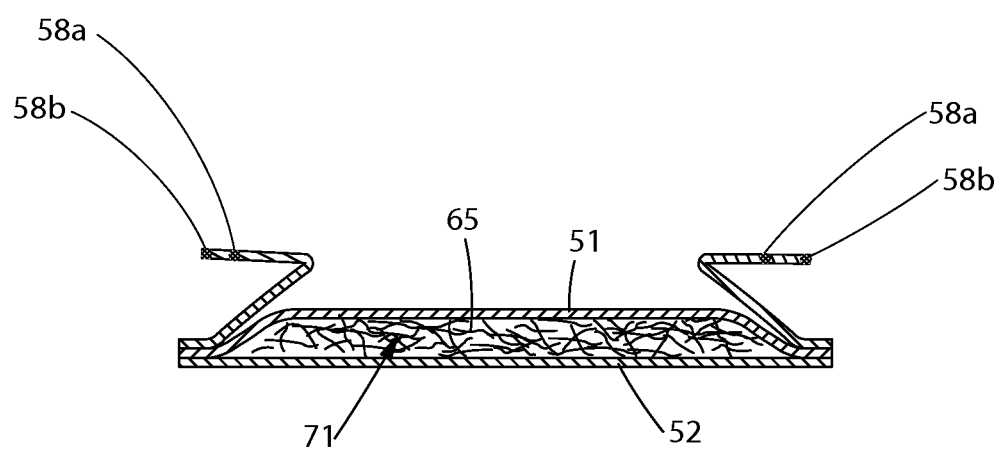
FIG. 5F is a cross sectional view of another example of an insert such as shown in FIG. 4, taken along line 5F-5F in FIG. 4.

Referring to FIGS. 5A, 5C and 5E, in other examples, absorbent material 66 in forward region 54 may be, respectively, dispersed within acquisition/distribution material 65 (FIG. 5A), contained within a separate liquid permeable structure or envelope 67 in fluid communication with acquisition/distribution material 65 (FIG. 5C); or dispersed on, or within an adherent matrix of, retaining material 68, and in fluid communication with acquisition/distribution material 65 (FIG. 5E). Conversely, the rearward region 55 may predominately contain acquisition/distribution material 65, but less storage material 66 as compared with forward region 54, or none (FIGS. 5B, 5D, 5F). Materials in forward region 54 also may be disposed according to construction described in one or more of co-pending U.S. application Ser. Nos. 12/141, 122, 12/141,124; 12/141,126; 12/141,128; 12/141,130; 12/141,132; 12/141,134; 12/141,141; 12/141,143; and 12/141,146, with a differing construction in rearward region 55.

In another example, storage material 66 and acquisition/distribution material 65 may occupying differing, distinct layers of absorbent core 71, as suggested by FIG. 5C. It may be desirable in some circumstances to make the layer containing acquisition/distribution material 65 larger in surface area (i.e., plan view surface area relative to the insert laid flat, as shown in FIG. 4) than the layer containing storage material 66, or vice versa. For example, if the layer containing acquisition/distribution material 65 is formed so as to have a larger surface area laterally across the insert in the forward region 54, this may serve to provide space for a greater quantity of acquisition/distribution material in the forward region. This may impart greater capacity in the forward region to rapidly absorb and distribute relatively large gushes of urine discharged toward the forward region, as may be desired for wearable absorbent articles for, e.g., older male babies and toddlers—enhancing containment capability of the insert.

In another example, however, such as for newborns and young babies, large gushes of urine might not be expected, but comparatively substantial quantities of liquid or low-viscosity fecal material may be. Thus, a wearable absorbent article for this group of intended wearers may include an acquisition/distribution layer of larger size, occupying a greater surface area, in the rearward region 55 of the insert. This may impart greater capacity in the rearward region to rapidly absorb gushes of liquid or low viscosity fecal material discharged toward the rearward region, and thereby enhance containment capability of the insert.

Differences between forward and rearward regions also may be included for purposes of sleep-use inserts. While an insert designed for awake-use may have the predominate proportion of its liquid-storage capacity in the forward region 54 as described above, an insert designed for sleep-use with, e.g., young babies, may have the predominate proportion of its liquid-storage capacity in the rearward region 55, to accommodate babies who sleep lying on their backs, by locating the predominate proportion of storage capacity where fluid exudates will flow under influence of gravity.

It also may be desired to dispose a thickening agent in the absorbent core in the rearward region 55 of the insert. A thickening agent may be useful for providing additional assurance that liquid or low viscosity fecal material will be thickened and thereby more immobilized, and more likely to be contained within the insert.

Insert 50 also may have overall shape/backsheet asymmetry. For example, viewed in a laid-flat position as shown in FIG. 4, insert 50 may occupy a larger surface area on one side of insert lateral axis 70 than on the other. This may be useful for purposes of comfort, body coverage, appearance, performance and/or economization in use of backsheet material(s). For example, in conjunction with including a predominate proportion of storage material 66, the forward region 54 of insert 50 may occupy a larger surface area, associated with a larger space within the insert to contain the storage material, e.g., so as to improve overnight absorption and containment capacity for wearers who sleep on their stomachs, and allow for the insert to remain flatter, particularly relevant when the absorbent material becomes swollen with absorbed liquid. Such larger surface area may be greater on one side of insert lateral axis 70 than the surface area occupied by the rearward region 55 on the other side of insert lateral axis 70.

Insert 50 also may have a narrowed region in the area which rests in the crotch region of the outer cover. This narrowing in the crotch region may serve to enhance wearer comfort by eliminating size and bulk between the legs. Referring to FIG. 2B, it may also serve to better enable the crotch region 26 of outer cover 20 to contain and maintain a laterally centered position of insert 50, by ensuring that insert 50, by having limited quantities of absorbent materials therein and limited width, does not swell beyond the space capacity of crotch region 26 of outer cover 20. Such narrowing may continue, for example, into the rear portion of the insert, thereby creating overall shape/backsheet asymmetry.

Insert 50 may also be asymmetrical across insert lateral axis 70 in other ways, to serve the same, related or other purposes as those described above.

It will be appreciated, therefore, that insert asymmetry across insert lateral axis 70 is a result of design and construction of the insert so as to have only one front region and only one rear region, i.e., the front and rear regions are not interchangeable, if the designed fit, comfort, performance and appearance of insert 50 are to be fully realized.

Grasp Structures, Removal and Disposal Aids

Referring to FIGS. 2G-2H, 2Q, 3 and 4, insert 50 also may include respective user grasp structures 59, 61. User grasp structures 59, 61 may be provided to enable the user to quickly and easily grasp insert 50 proximate its respective ends.

Grasp structures as shown and/or suggested may enable the user to more quickly grasp and stretch insert 50 from a contracted position similar to that depicted in FIG. 3, to an extended position similar to that depicted in FIG. 4, which may be desirable for installing insert 50 into an outer cover. If user grasp structures 59, 61 are centered proximate to the respective ends of insert 50 as shown, this may also provide visual assistance to the user for co-locating respective centered fastener component pairs, described in more detail below.

Additionally, user grasp structures 59, 61 may serve to enable the user to quickly and easily grasp insert 50 proximate to its respective ends, which as a result of their distance from exudation points on a wearer's body, are less likely to be soiled at the time replacement of insert 50 becomes necessary or desirable. Thus, the user may be better enabled to avoid contacting the wearer's exudates with the user's hands when removing a soiled insert 50 from an outer cover 20. A configuration having laterally extending grasp structures 59 near the insert corners as suggested in FIG. 2Q may better enable a user to avoid soiling his/her hands when removing a soiled insert from an outer cover, and better enable the user to fold or roll up the soiled insert for disposal.

Figure 2D:
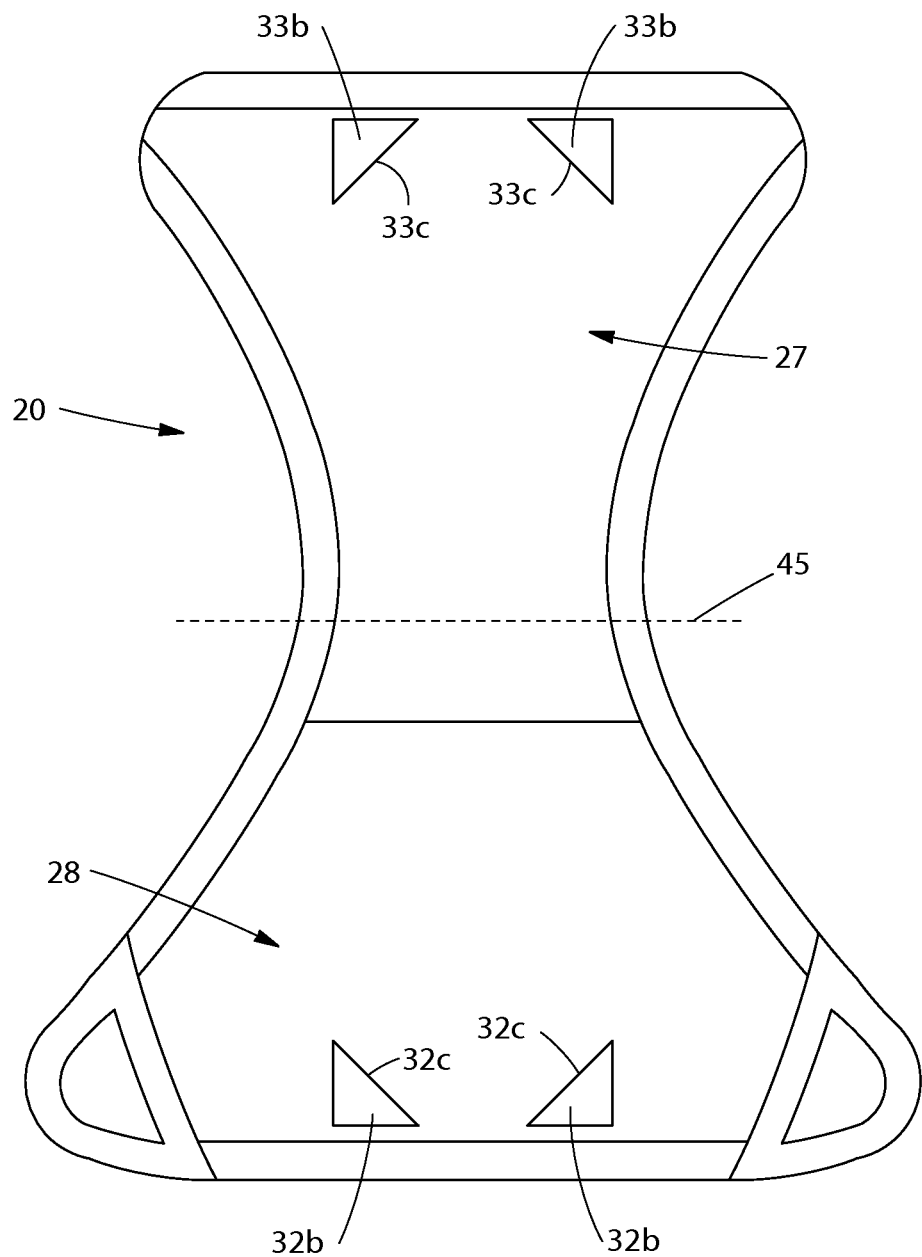
FIG. 2D is a plan view of an outer cover opened and laid flat, inner surface facing the viewer.
Figure 2E:
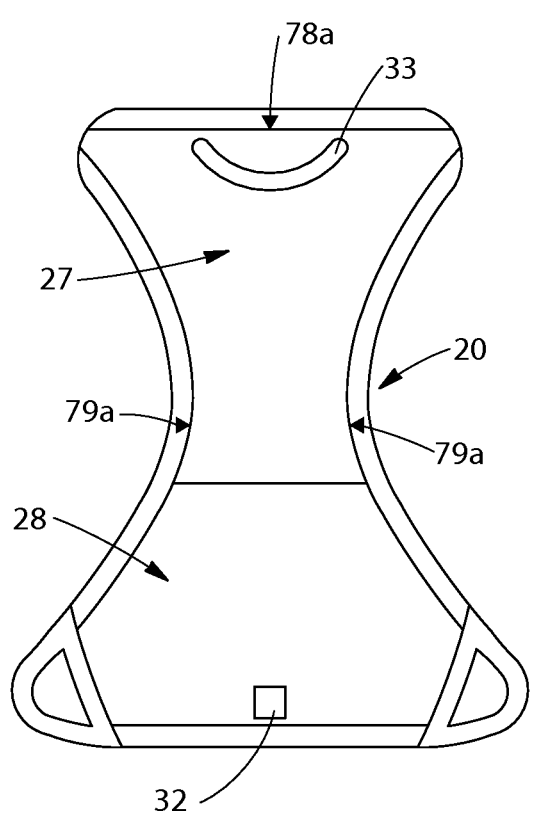
FIG. 2E is a plan view of an outer cover opened and laid flat, inner surface facing the viewer.
Figure 2F:
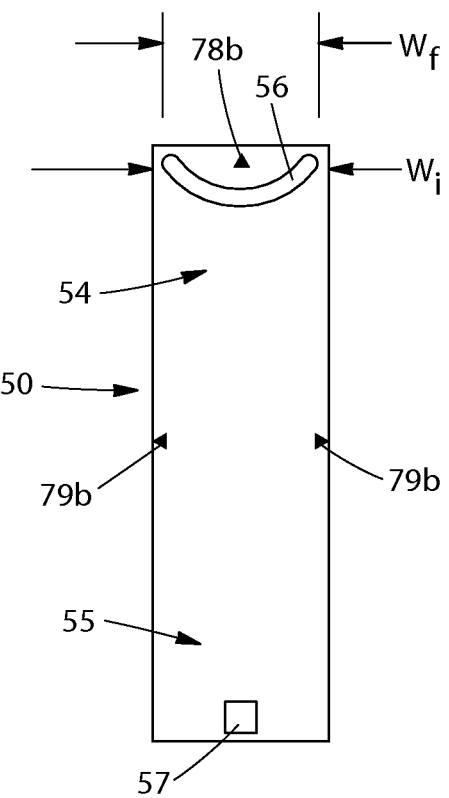
FIG. 2F is a plan view of an insert opened and laid flat, outer (garment-facing) surface facing the viewer.
Figure 2G:
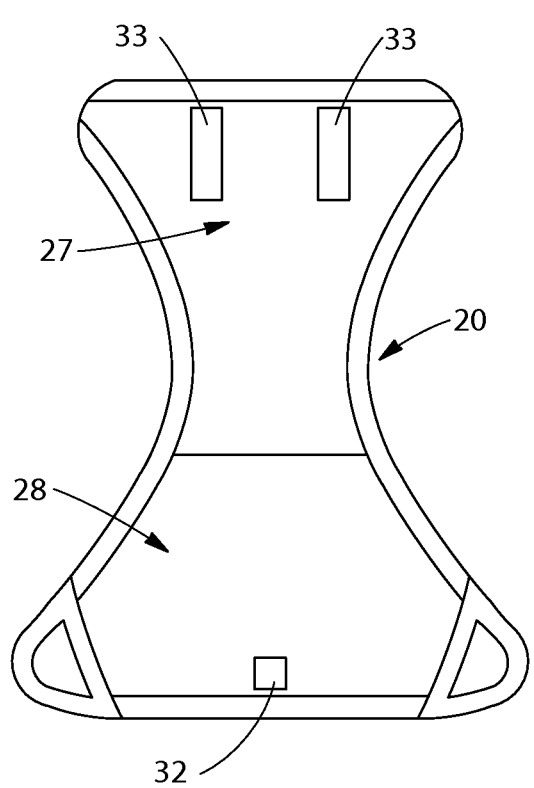
FIG. 2G is a plan view of an outer cover opened and laid flat, inner surface facing the viewer.
Figure 2H:
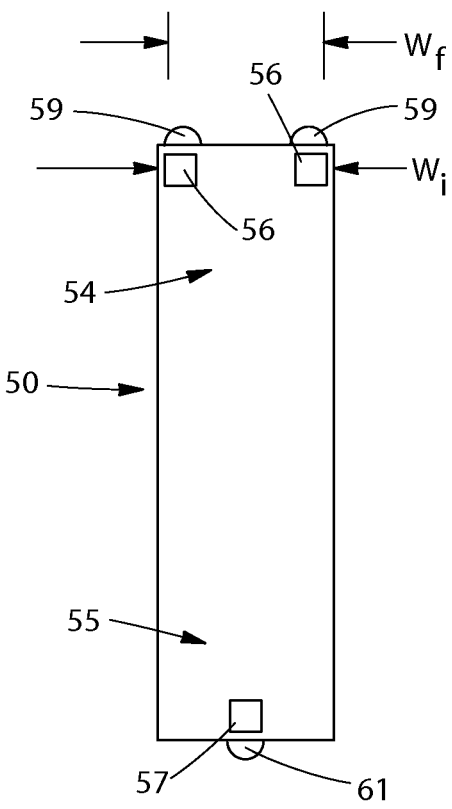
FIG. 2H is a plan view of an insert opened and laid flat, outer (garment-facing) surface facing the viewer.
Figure 2I:
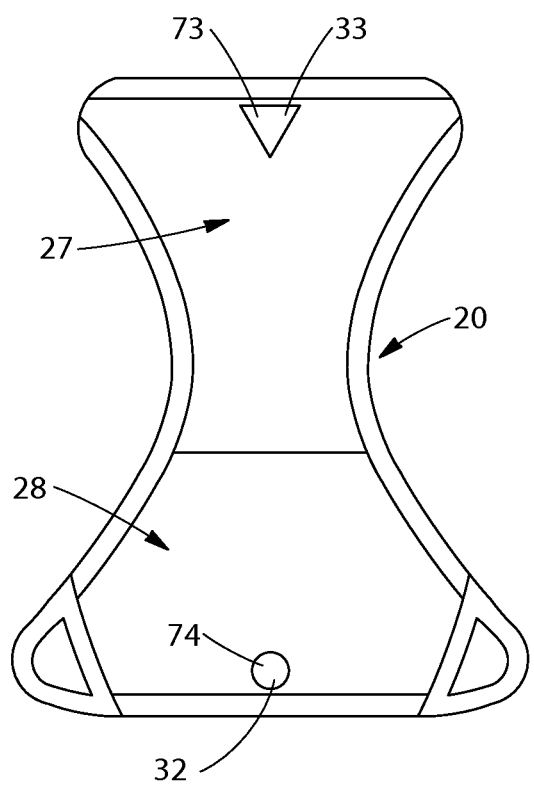
FIG. 2I is a plan view of an outer cover opened and laid flat, inner surface facing the viewer.
Figure 2J:
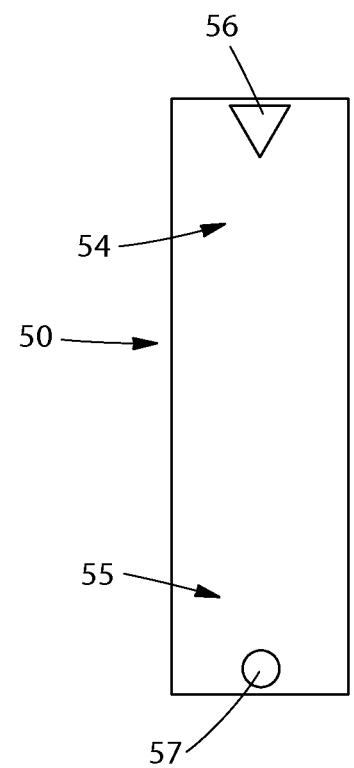
FIG. 2J is a plan view of an insert opened and laid flat, outer (garment-facing) surface facing the viewer.
Figure 2K:
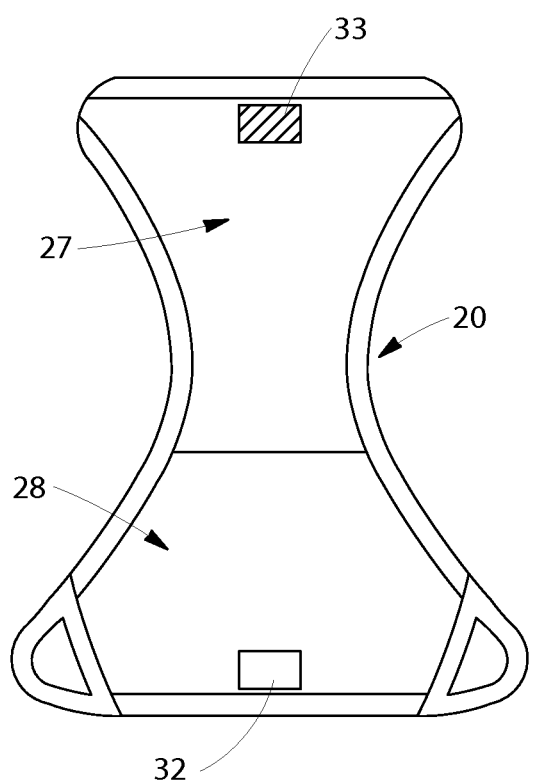
FIG. 2K is a plan view of an outer cover opened and laid flat, inner surface facing the viewer.
Figure 2L:
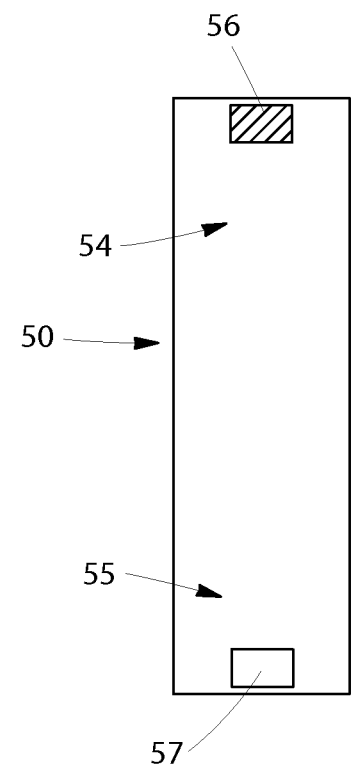
FIG. 2L is a plan view of an insert opened and laid flat, outer (garment-facing) surface facing the viewer.
Figure 2O:
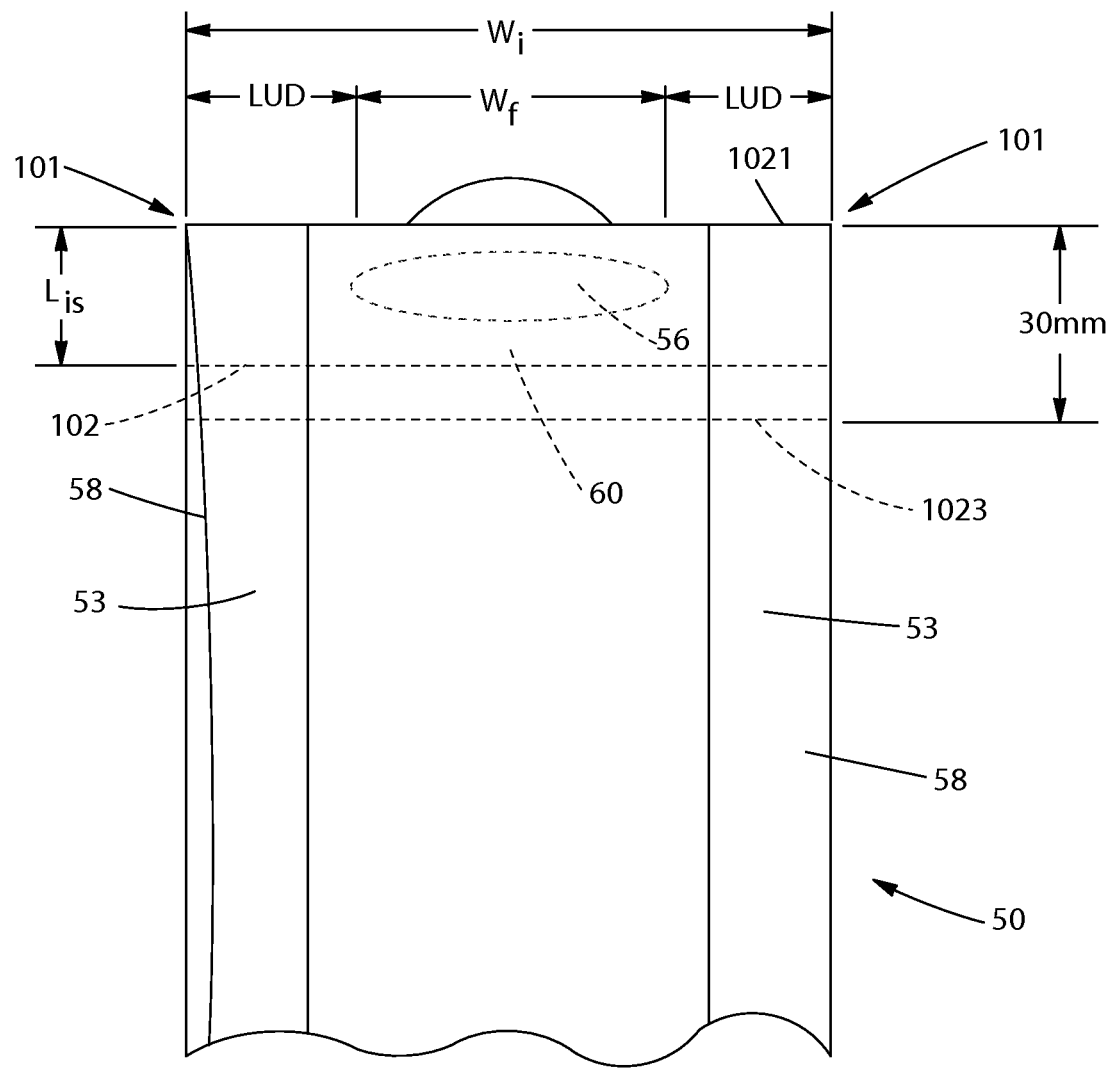
FIG. 2O is a plan view of one end of an insert opened and laid flat, inner (wearer-facing) surface facing the viewer.
Figure 2P:
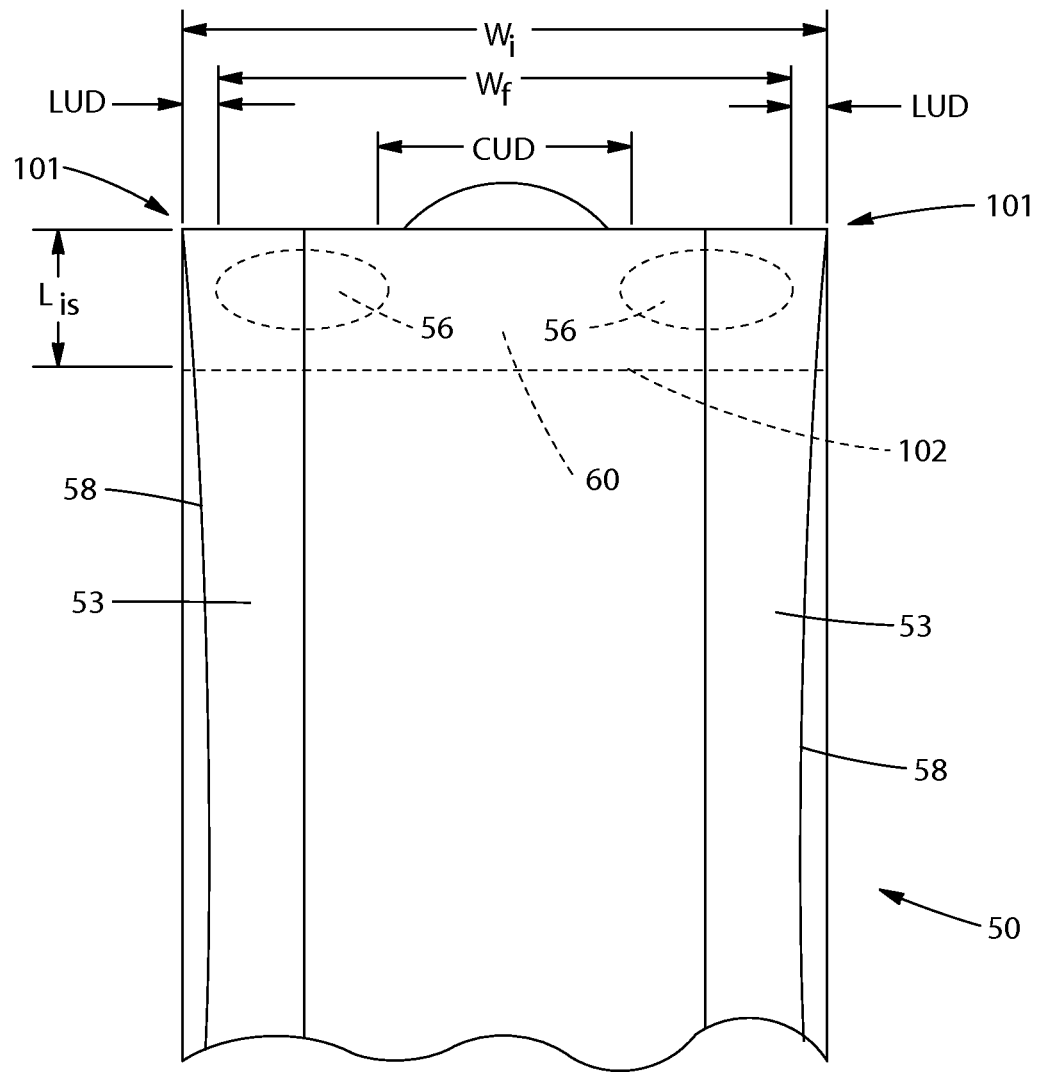
FIG. 2P is a plan view of one end of an insert opened and laid flat, inner (wearer-facing) surface facing the viewer.
Figure 2Q:
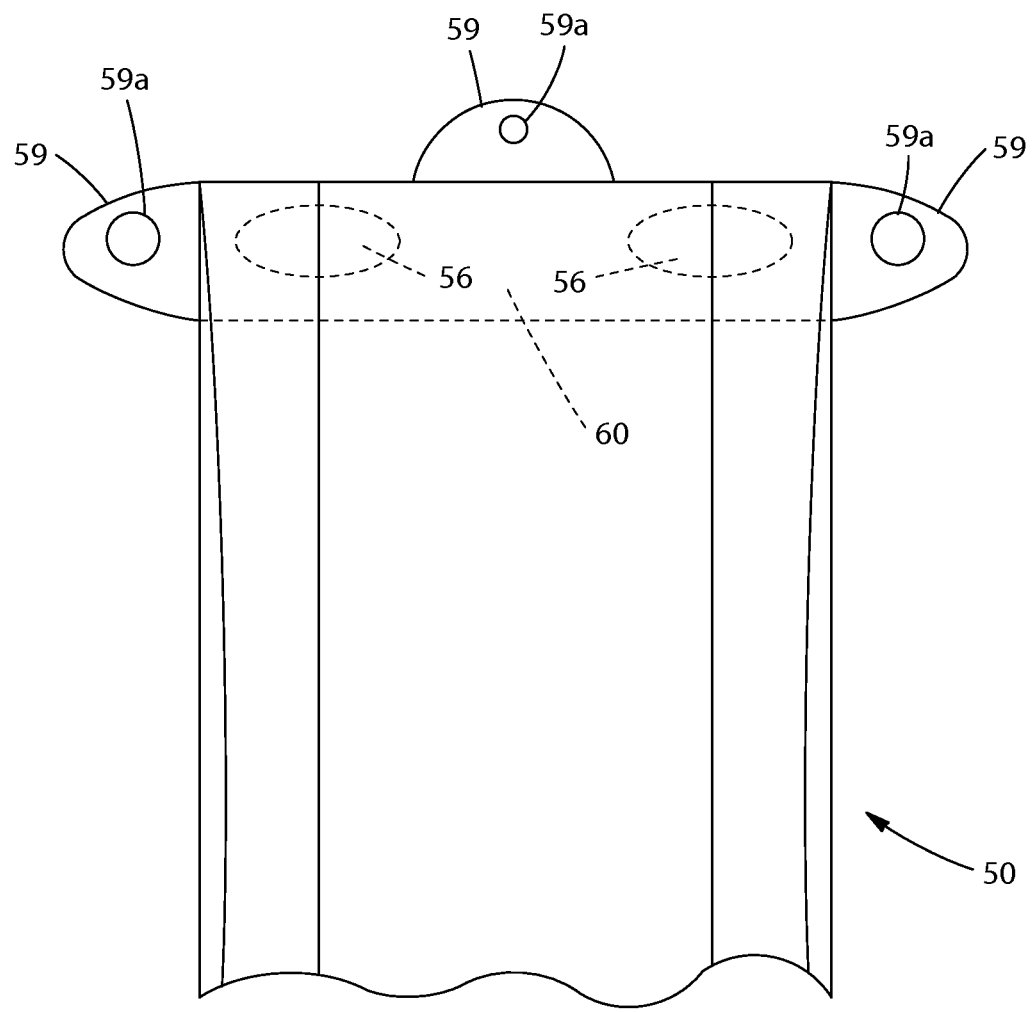
FIG. 2Q is a plan view of one end of an insert opened and laid flat, inner (wearer-facing) surface facing the viewer.

Referring to the example depicted in FIGS. 2G-2H and 2Q, it may be desirable in some circumstances to include more than one grasp structure 59 on the insert. This may be deemed useful in examples such as depicted in FIGS. 2G-2H and 2Q, where more than one fastener component 56 is disposed on an end of an insert. In such circumstances, including a separate grasp structure 59 associated with and proximate to each fastener component 56 may enable a user to manipulate portions of an insert to more easily accurately locate and install it within an outer cover with fastener components 59, 33 suitably co-located and/or aligned. It may also enable a user to more easily tug the fastener components 56 away from paired fastener components 33 to separate them, when it is necessary to remove the insert from the outer cover, by localizing or focusing the user's tugging forces where they are needed to effect such separation.

User grasp structures 59, 61 may include tab-like extensions as shown in FIGS. 2E-2F, 2Q, 2S, 2T, 3 and 4, with free ends unattached to the outer cover 20 when insert 50 is installed therein, which are easily graspable. User grasp structures may have various forms. By way of non-limiting example, user grasp structures may take the form of loop-like extensions extending from the ends of insert 50, finger holes through insert 50 proximate the ends thereof, pockets with openings facing the lateral centerline 70 of the insert, and other structures that facilitate grasping and pulling of insert 50 at locations proximate to its ends.

Additionally, grasp structures 59, 61 may be formed of materials having a high coefficient of friction (e.g., at least about 0.5), resiliently compressible materials and/or surfaces having three-dimensional relief, to facilitate secure gripping and pulling the insert by the user.

Grasp structures 59, 61 also may be configured or adapted so as can be folded over or under the respective ends of insert, toward the lateral centerline of the insert. This can serve to conceal the grasp structures behind other materials and protect them from contamination by bodily exudates. Alternatively or in addition, it can serve to add convenience for the user.

As suggested by FIGS. 2Q, 2S, 2T and 3, grasp structures 59, 61 may be formed of, or be longitudinal, lateral or other extensions of, material(s) forming end support stiffeners 60, 62 (described further below).

Referring again to FIG. 3, an insert may also include a disposal aid 81, configured to hold the insert in a folded or rolled configuration for convenience of neat handling and disposal following removal of the soiled insert from an outer cover. As suggested in FIG. 3, disposal aid 81 may be in the form of a strip of removable/refastenable tape. Upon removing a soiled insert 50 from an outer cover, the user can fold or roll it up longitudinally, backsheet 52 facing out, and then lift and refasten a tape-form disposal aid 81 to the backsheet to secure the insert in the folded or rolled condition. Other forms of disposal aids, which serve to hold an insert 50 in a folded or rolled up condition with topsheet 51 in and backsheet 52 out, may be used.

Insert/Outer Cover Fastener Components; Orientation Indicia; Other Possible Features Referring back to FIGS. 2B, 3 and 4, as previously noted, outer cover 20 may have one or more insert fastener components such as front and/or rear insert fastener components 33, 32 disposed thereon. Insert 50 may have front and/or rear fastener components 56, 57 disposed thereon. Respective front and/or rear fastener components 56, 57 on insert 50 may be selected and/or adapted to be cooperative to enable fastening with respective front and/or rear insert fastener components 33, 32 disposed on outer cover 20.

Types, Locations and Localization of Fastening Locations

In one example, to enable fastening of respective front and rear fastener components 56, 57 of insert 50 with respective front and rear insert fastener components 33, 32 on outer cover 20, respective fastening pairs 56, 33 and 57, 32 may include cooperating fastener components. An example of a suitable hook-and-loop fastening system is a VELCRO system, a product of Velcro Industries B.V., components of which are available from Velcro USA, Inc., Manchester, N.H. A hook-and-loop fastening system provides certain advantages. Because the respective hook and loop components are supplied in sheet or strip form, they may be cut into suitably shaped patches that can be affixed to a cloth substrate by various mechanisms, including adhesive bonding, mechanical bonding, ultrasonic bonding, sewing, stitching, serging, edging, and the like. If respective hook-and-loop patches are used as fastener components, relative ease of fastening, simplicity and convenience for the user (as compared with, for example, fastener components such as a button and button hole) are one among several advantages provided, because fastening is effected simply by placing the fastener components in face-to-face contact and applying gentle pressure.

Some types of hook components may, in some circumstances, tend to snag or catch undesirably on a variety of materials in addition to intended corresponding loop components, while most types of loop components currently available do not have this tendency. Thus, in some circumstances it may be desired that patches of loop components form one or both of insert fastener components 33, 32, while patches of hook components form one or both of fastener components 56, 57. This arrangement places a non-snagging insert fastener component on the outer cover. This may be desirable in some circumstances, such as when the outer cover 20 is designed to be reusable—reducing the likelihood that components on an outer cover 20 will undesirably snag on other parts of outer cover 20 or on other articles, such as clothing articles, being stored or laundered along with outer cover 20.

However, fastening pairs 56, 33 and 57, 32 need not necessarily include respective components of a hook-and-loop fastening system, and need not necessarily include respective components of a two-component fastening system. Rather, a fastening system may require only one fastener component, or use other types of fastener components. Fastener components used may be adapted to engage, retain, and otherwise hold the insert or a portion thereof. A fastener component on outer cover 20 may include a patch of adhesive; a structure having a region of relatively high coefficient of friction; a pocket; flap; strap; or other capturing, holding and/or retaining surface, device or structure. Thus, referring to FIG. 2C in one example, the inside of outer cover 20 may include one or more pocket structures 32a, 33a situated on or along the inner surface 25 of outer cover 20, in, e.g., the front region 27 or rear region 28. Such a pocket structure may have an opening facing downward or upward (relative to the wearer in a standing position, and relative to FIG. 2B). A pocket structure may be adapted to receive, fit and capture, for example, the forward edge and a portion of forward region 54 of insert 50. A pocket structure 33a, 33b may have an opening facing lateral axis 45, such that an end of insert 50 may be inserted therein and retained thereby. A pocket structure may alternatively have an opening facing away from lateral axis 45, such that an end of insert 50 may be inserted therein and retained thereby, and then insert 50 may be folded back over such opening and toward lateral axis 45. Referring to FIG. 2D, in another example, one or more pockets 32b, 33b may be provided in the front and/or back region on the inner surface of the outer cover 20 positioned such that a corner of an insert 50 may be inserted into and retained by the pocket. Such pockets may have respective openings defined by edges of material 32c, 33c forming an angle with respect to both the lateral and longitudinal axes of between about 0 and 90 degrees, but more preferably, between about 30 degrees and 60 degrees. One or more of such fastener components may be provided in lieu of, in addition to, or in combination with, other fastener components disposed at the front region of the outer cover 20 and forward region of insert 50. As one example, an outer cover 20 may have a pocket structure 33a in front region 27 (see FIG. 2C) in combination with a patch of loops component forming rear fastener component 32 (see FIG. 2B). With such a structure and a suitably adapted insert 50 having a patch of hooks as fastener component 57, to install the insert the user may insert the forward edge of insert 50 into the pocket structure 33a, and then fasten the rearward portion of insert 50 into the rear region of the outer cover 20 by engaging respective fastener components 32, 57.

In another example, fastener components 32, 33 may be respective patches of hook components, while fastener components 56, 57 may simply be surfaces formed of woven or nonwoven material adapted to be attachably engageable by such hook components. In yet another example, fastener components 56, 57 may include respective patches of hook components, while fastener components 32, 33 may simply be surfaces formed of woven or nonwoven material suitable for, or adapted to be, attachably engageable by such hook components.

Also, a fastener component in any form, including a respective component of a fastening pair 56, 33 and 57, 32 may be disposed on either of insert 50 or outer cover 20. For example, a hook patch may be disposed on either of insert 50 or outer cover 20, with a cooperating loop patch disposed on the other of insert 50 or outer cover 20.

An insert fastener component such as component 32 on outer cover 20 may be attached or connected to at least a portion of an anchoring system, such as an anchoring band 38, or diagonal anchoring band 38a. This may provide, as one advantage, the distribution of structural loading resulting from the weight of absorbed or contained exudates, as described in one or more of the patent applications cited above, in the description of anchoring bands.

Fastening locations may be multiply disposed, for example, at each of the four corners of insert 50 and corresponding locations on outer cover 20, and even at other locations along insert 50 and outer cover 20, created by fastener components suitably selected and disposed. For example, fastener components may be disposed along the longitudinal sides proximate the ends of the insert in the forward and/or rearward region of the insert. Fastener components may be disposed adjacent an edge of the insert, or may be disposed laterally and longitudinally inboard of the edge. For example, a fastener component may be disposed at least 1, 2, or 3 cm from any or all edges of the insert. In certain embodiments, at least one fastener component is disposed at least a distance from the lateral or longitudinal edge, or both, of the insert equivalent to one-fourth the width of the insert. In one embodiment, a fastener component is disposed along at least about one-fifth of the length of the longitudinal axis.

A fastener component may have the form of a patch or strip, of material bearing adhesive, pressure-sensitive adhesive, or a cohesive material on a garment-facing surface, or otherwise be formed of adhesive, pressure-sensitive adhesive or cohesive material. The patch or strip may cover at least about 20%, 50%, 75%, or even substantially all of the garment-facing surface of the insert. Such a patch or strip may be affixed to and cover at least a portion of the garment-facing surface of the insert and may, optionally, be covered by release paper to preserve the adhesive/cohesive and prevent contamination and unintended adhesion during storage and carrying, until the user is ready to install the insert. When the user is ready to install the insert within an outer cover, the user may peel away the release paper, thereby exposing the adhesive/cohesive and making it available to function to adhere the insert within the outer cover. A fastener component including an adhesive or cohesive may be combined in a fastening configuration with other types of fastener components described herein on an insert, at either or both ends; or one end of an insert may have one or more adhesive or cohesive-type fastener components and the other end of the insert may have one or more other type(s) of fastener components described herein.

A fastening system such as either of fastener component pairs 56, 33 and 57, 32 may form a singularized, laterally centered and localized fastening location proximate each of, or either, the forward/front and/or rearward/rear ends/regions as suggested in the Figures. Having a singularized, localized fastening location substantially laterally centered respectively on the insert and the outer cover at one or both of the insert ends, as suggested in FIGS. 2B and 3, may provide certain advantages.

One advantage may be simplicity and ease of installation for the user, resulting from singularization and localization of a location at which the user must co-locate and fasten insert 50 to outer cover 20 at an end of the insert.

A second advantage may result from the partially force-decoupled attachment of insert 50 within outer cover 20 resulting from a singularized, localized fastening location. With this force-decoupled arrangement, the portions of outer cover 20 surrounding fastener component(s) 33, 32, such as waistband portions 34, 35, and front and, especially, rear regions 27, 28, may laterally stretch and contract substantially independently of and unimpeded by the structure of insert 50 and portions thereof. This may avoid lateral buckling or bunching along the ends of insert 50 with lateral contraction of the outer cover 20, which may cause discomfort and/or may create gaps between the wearer-facing surfaces at the end of the insert and the wearer's skin, and a resulting vulnerability to leakage. It may also avoid having the structure of insert 50 restrict outer cover 20 from stretching or contracting laterally, which may otherwise occur as a result of a more force-coupled arrangement therebetween. Such lateral bunching, buckling or restricting of stretch and contraction of the outer cover otherwise may be incidental to fastening insert 50 within outer cover 20 in a manner that force-couples a greater portion of the width of insert 50 to outer cover 20, e.g. by use of more than one fastening location across the width of insert 50 proximate a given longitudinal location, or by use of a laterally delocalized/extended continuous fastening location along a larger portion of the width of insert 50. Force-decoupling, therefore, may provide for enhancement of fit, containment capability, appearance and wearer comfort, and improved capability for maintenance of intended insert shape and performance while worn.

Thus, in one example, referring to FIG. 2O, a patch of hook components forming a fastener component 56 and/or 57 attached to insert 50 may be substantially laterally centered on the insert as suggested in the figure, and may have an effective width $W_f$ attached along insert 50 that extends no more than about 50% of the greatest lateral width $W_i$ of the insert 50 not including an end support stiffener (as described below). This provides that no more than about 50% of the width of the insert 50 will be force-coupled to the outer cover by operation of the patch of hook components, and that, correspondingly, at least about 50% of such width (i.e., that portion of width $W_i$ that is not attached to, or force-coupled to, the insert along width $W_f$) is force-decoupled from the outer cover 20 when insert 50 is installed therein. In some circumstances, it may be desired that the portion of the lateral width of forward region 54 and/or, especially, of rearward region 55 of insert 50 that is force-decoupled from the outer cover is even greater than about 50%. Thus, it may be desired that the width $W_f$ of a fastener component 56 or 57, comprising, e.g., a continuously attached patch of hooks, is no more than about 40%, no more than about 30%, or even no more than about 20%, of width $W_i$. In another example, it may be desired in some circumstances that at least about 50% of width $W_i$ in the front and/or rear region 54, 55, is force-decoupled from the outer cover. In some circumstances it may be desired that more than about 50%, more than about 60%, more than about 70%, or even more than about 80%, of width $W_i$, is force-decoupled from the outer cover when installed therein.

In some circumstances, however, it might not be deemed important that more than 50% of the width $W_i$ is force-decoupled from the outer cover. In some circumstances a useful benefit may be derived from force-decoupling a lesser portion of the insert width, while satisfying another objective. For example, an insert 50 might include a fastener component 56 and/or 57 formed of a patch of hooks that is comparatively less aggressive than other hooks-type components available, and therefore requires relatively greater contact surface area to provide satisfactory fastening performance. In circumstances such as these, and others, it may be sufficient for achieving some force-decoupling benefits while still providing required fastening/holding performance, for less than about 90%, more preferably less than about 75%, still more preferably less than about 60%, of the lateral width of the insert to be force-coupled to the outer cover.

Other fastener components that provide such singularized and relatively laterally localized fastening locations, providing limited force-coupling across the lateral width of at least one end of insert 50, are possible. Other suitable fastener components may include tab and slot fasteners, macro hook and loop fasteners, button fasteners, interlocking fasteners, hook and slot fasteners, snap fasteners, adhesive fasteners, and other fastener types available.

While the singularized, localized fastening locations discussed above may provide the advantages described, in some circumstances they may also introduce disadvantages. In some insert embodiments, the outer corners of the insert 50, if not secured to the outer cover, may be prone to buckling, sagging or rotating toward the insert lateral axis 70, or out of the contour of the predominate portion of the insert as worn, in response to forces resulting from wearer motion or position, or exudate loading, e.g., in the crotch region. Also, referring to FIG. 3, and from the description of standing cuffs 53 with cuff elastics 58*a*, 58*b* along edges 58 as set forth above, it can be appreciated that, if longitudinal tensile forces are imparted by pre-strained cuff elastics 58*a*, 58*b*, standing cuffs 53 may tend to pull the respective outer corners of insert 50 longitudinally toward each other. If there is not structure present to resist these forces, the outer corners of insert 50 may sag or buckle, and standing cuffs 53 may be loosened, sag or even collapse. This may lead to gaps between the edges 58 of the cuffs and the wearer's body. In turn, this may compromise the cuffs' gasketing function, and increase the risk of leakage.

The disadvantages identified above may in some circumstances be of greater concern in the front region of the insert. While it may be important at both ends of the insert, control of the insert corners may be particularly important in the forward region 54, due to its closer proximity to the urethra. Insert designs in which exuded urine is predominately stored in the forward region may concentrate the weight and expansion stress of exudate loading in the forward region 54, and thus, on the forward corners of the insert 50. Stresses in the front of the insert acting at or near the forward corners also may be applied, or multiplied, by the wearer's forward articulation of the legs (together or alternately as when crawling or walking) or bending of the torso forward at the waist.

At the same time, in some circumstances force-decoupling may be more desirable in the rear region of the insert and chassis 28, 55 because greater demands for waistband stretch in the rear may result from anatomical features and body movement modes. For example, because a wearer may ordinarily bend forward at the hips but not backward, such motion, combined with the contours of the buttocks and hips, may impose a greater demand for lateral stretch and contraction in the rear waistband area than in the front waistband area, for purposes of fit, comfort and appearance.

Thus, as depicted in FIGS. 2E-2F and 2G-2H, examples are contemplated wherein singularized/localized, laterally centered, force-decoupled fastener component pairs 32, 57 may be employed in only one of the front or rear of the article, such as in the rear region 28 of the outer cover 20 and rearward region 55 of the insert 50, while fastener component pairs 33, 56 effectively controlling the forward corners of the insert 50 may be employed in the other region, such as front region 27 of the outer cover 20 and forward region 54 of the insert 50. This arrangement may serve to allow force decoupling in one region where force decoupling may be most desirable, and provide insert corner control in another region where corner control may be most desirable.

Control of the corners to reduce the likelihood of sagging and/or rotation of components or portions of an insert may be improved, in one group of examples, by placement and/or shaping of fastener component pairs. Referring again to FIGS. 2E-2F and 2G-2H, it can be seen that fastener component pairs 33, 56 in, e.g., the respective front/forward regions of the outer cover 20 and insert 50 may be arranged, shaped, sized and/or placed such that the forward corners of insert 50 are effectively captured and held to the outer cover 20 when insert 50 is installed therein. The fastener component(s) 56 disposed on the insert may, accordingly, have an effective width $W_f$ at least equal to about one-fourth, or one-half, of the width of the insert. In some examples, the width $W_f$ of the fastener component(s) may be between about 50% and 100%, or between about 75% and 95%, or even between about 85% and 95% of width $W_i$. (See FIGS. 2O and 2P for reference with respect to $W_i$ and $W_f$.) If multiple fastener components 56 are included, e.g., in a line, array, or other pattern, the fastener component width $W_f$ is considered to be the lateral distance between the laterally outermost edges of the fastenably effective portions of the laterally outermost fastener components 56. (For purposes herein, "fastenably effective portion" means any portion of a fastener component that effectively force-couples a portion of the width of an insert to an outer cover.)

Referring to FIG. 2G-2H, in examples having more than one fastener component 56 at a given longitudinal end of the insert, an unattached portion of the insert lateral width along the end will be present between the laterally inside edges of the fastener components 56. This may create the possibility for sagging and/or buckling of the end of the insert across the unattached portion, and in turn, the possibility for wearer discomfort or exudate leakage along the end.

Insert End Support Stiffeners

In order to further address issues which may be presented by force-decoupling or force-coupling and fastener component arrangements discussed above, it may be desirable to include a stiffening component proximate one or both ends of the insert. For example, in some circumstances it may be desirable for an insert end to be resistive to excessive bending, bunching or buckling across the insert longitudinal axis. In other circumstances it may be desirable for insert corners to be resistive to sagging or buckling, as described above.

Referring to FIGS. 3 and 4, an end support stiffener 60 and/or 62 may be included at one or both ends of the insert. Such an end support stiffener may serve to aid the user in engaging the insert with the outer cover, and to help insert 50 maintain its intended shape and configuration while being worn beneath an outer cover, i.e., help maintain its intended shape, position and gasketing functions (e.g., of the standing cuffs 53). An end support stiffener 60, 62 also may help control the corners of the insert regardless of the size, type or location of fastener components included on the insert. In addition to providing resistance to longitudinal pull of cuff edges 58, end support stiffeners 60, 62 may provide resistance to bending in any direction or plane.

An end support stiffener 60, 62 may be affixed to, or incorporated within, insert 50 proximate one or both ends thereof as suggested by FIGS. 3 and 4. In addition to increasing the tendency of insert 50 to maintain optimal shape while in use, such an end support stiffener may increase the tendency of the associated end of insert 50 to stay open and flat before insert 50 is installed in an outer cover. Because the ends of insert 50 may otherwise be folded over or bunched while being stored and/or carried by the user before installation, an end support stiffener may enhance user convenience, by causing the associated end of insert 50 to maintain or seek a shape/configuration that requires less manipulation by the user to install it in an outer cover.

Referring to FIG. 4, one or more end support stiffeners 60, 62 may be disposed in a lateral orientation with respect to the insert and formed of any flat, sheet-like or card-like material, or any flat, stiffened assembly that adds stiffness to the insert end that exceeds the stiffness of the adjacent portion lying nearer the insert lateral axis 70. In one example, an end support stiffener may be formed by folding over a portion of the insert end material(s) to create a stiffened region comprising folded layers of material. In another example, an end support stiffener 60, 62 may be formed by depositing onto the end of insert 50 lateral bands, strips or other shapes or patterns of deposits of liquid or semi-liquid adhesive or other material that cures or cools to a stiffened state, and thereby imparts added stiffness to the substrate to which it is applied. In another example, an end support stiffener may be formed of cardboard in sheet form, or similar material. One example of suitable stiffener material is 0.031 in. thick VOLARA 6A foam supplied in sheet form (a product of Sekisui Voltek, LLC, Lawrence, Mass.); other thicknesses of this and like materials are available and may be used. Stiffener materials may be laminated with or adhesively applied to portions of insert 50 to be stiffened, or applied, affixed or included by any other suitable method. Other examples of suitable stiffening materials may include added layers of nonwovens; tufted nonwovens; films; laminates of films, nonwovens and/or other materials; patches of fastener loops or hooks components; portions of a suitable grasp structure; portions of one or more of the other insert and/or core materials, etc. Persons of ordinary skill in the art will readily appreciate that stiffness as described and measured by tests herein may be increased by the selection and/or addition of materials to the construction of an insert end in a variety of ways.

End support stiffeners 60, 62 may increase planar, lateral and/or longitudinal stiffness of the areas of insert 50 in which they are located, as compared with portions of the insert adjacent such stiffeners and closer to the lateral axis 70 with respect to a plan view (such as FIG. 4). These differing orientational aspects of stiffness may affect various attributes of the insert. For example, referring to FIG. 3, it can be seen that the ability of a portion including an end support stiffener 60, 62 (stiffened portion) to resist longitudinal tension forces in standing cuffs 53, particularly along edges 58, may be affected by one or more of planar and longitudinal stiffness of the stiffener. The pliability and relative comfort or discomfort for the wearer, associated with presence of a stiffened portion, may be affected by planar stiffness of the stiffener.

One measure of stiffness relevant to the ability of a stiffened portion to resist longitudinal tension forces in standing cuffs is Edge Deflection Force, which is measured according to the Edge Deflection Force Measurement Method set forth below. In view of the potentially competing objectives of structural rigidity and comfort, it may be desired that a stiffened portion of an insert end, i.e., the portion of an end that includes an end support stiffener, have an average Edge Deflection Force (30) from at least about 0.2 N, more preferably at least about 0.5 N, or alternatively, and even more preferably, respectively, about 0.2 N to about 3.0 N, or about 0.4 N to about 2.0 N, or even about 0.50 N to about 1.70 N, as measured by the Edge Deflection Force Measurement Method set forth below. (Where the terms "Peak Edge Deflection Force (y)" or "Edge Deflection Force (y)" are used herein, "y" is the lateral dimension in millimeters of distance 1010 as described in the Edge Deflection Force Measurement Method and depicted in FIG. 6A herein.)

Other measures of stiffness relevant to the comfort of a stiffened portion are the Peak Bending Force and Bending Stiffness, which are measured according to the Bending Stiffness Measurement Method set forth below. In view of concerns for comfort, it may be desired that a stiffened portion of an insert end, i.e., the portion of an end that includes an end support stiffener, have an average Peak Bending Force of between about 0.1 N and 4.0 N, more preferably between about 0.1 N and 3.7 N, even more preferably, respectively, between about 0.2 N and 3.0 N, or between about 0.5 N and 2.5 N. Additionally, or in the alternative, it may be desired that a stiffened portion of an insert end have an average Bending Stiffness of between about 100 N/m and 1,000 N/m, more preferably between about 100 N/m and 600 N/m, even more preferably, respectively, between about 200 N/m and 500 N/m, or 300 N/m and 400 N/m.

An end support stiffener 60, 62 may be located adjacent or near one or both ends of insert 50 and may extend laterally from the lateral center thereof to stiffen the insert along a substantial portion of its width. Alternatively, a stiffener may be disposed such that its longitudinally outermost edge (relative the insert, i.e., the edge farthest from lateral axis 70) is disposed at least about 0.5, 1, or 2 cm from the associated end of insert 50, and may be substantially laterally centered about the longitudinal center line of the insert. The one or more end support stiffeners 60, 62 may have a width of at least about 30%, more preferably about 40%, even more preferably about 50% to about 100% of width $W_i$, or may extend beyond the longitudinal edges of the other materials forming the insert. An end support stiffener 60, 62 may have any longitudinal dimension, although a longitudinal dimension less than 25% of the insert length L may better assure comfort for the wearer, and therefore, may be desired. In some examples, the longitudinal dimension $L_{is}$ (see FIGS. 2O, 2P) of an end support stiffener 60 may range from about 5 mm to about 50 mm, measured from the longitudinally outermost edge of the stiffener, to the longitudinally innermost extent (i.e., nearest lateral axis 70) of the stiffener. A stiffener also may extend laterally beyond one or both of the longitudinal edges of other materials forming the insert, and may extend longitudinally beyond the lateral edge(s) of other materials forming the insert at its end. One or both ends of the insert may include an end support stiffener. A stiffener may include, be formed of, or be further stiffened by, a fastener component such as a strip or patch of hooks material. In examples wherein the insert comprises an end support stiffener at both ends, the respective end support stiffeners may have differing shapes, dimensions, stiffness, thickness, color, structure, placement, material(s) or composition. An end support stiffener also may include, or be integral with, a grasp structure or fastener component as described above, and as suggested in FIG. 3 (end support stiffener 60 is depicted as integral with grasp structure 59).

Fastening Component Arrangement and End Stiffness Characteristics

As discussed above, use of an effectively force-decoupled, singularized/localized fastening system at an end of an insert may present both advantages and disadvantages. Some of the disadvantages may be mitigated by the inclusion of an end support stiffener, or alternatively, by use of a more force-coupled fastening system that provides support at the insert corners.

Similarly, use of a fastening system having two separated fastener components at an end of an insert, at or near the corners, may present both advantages and disadvantages, including added cost and complexity for the manufacturer. Some of the disadvantages may be mitigated by the inclusion of an end support stiffener, and/or by use of a relatively force-decoupled, singularized/localized fastening system.

Inclusion of an end support stiffener on an insert may have beneficial effects; however, it also may create issues of comfort for the wearer, and added cost and complexity for the manufacturer.

In view of the respective advantages and disadvantages presented by these various types of insert-to-outer cover fastening and/or support systems, it may be desirable to utilize combinations of these systems that strive for a balance between user convenience, fit, structural support, integrity and containment function for the insert and standing cuffs, wearer comfort, and minimized cost and complexity for the manufacturer.

In some circumstances, inclusion of fastener component pairs which effectively attach the end corners of the insert to the outer cover may be undesirable for reasons of cost and/or complexity, or may sacrifice the advantages of having only one singularized/localized and laterally centered fastening location proximate each end of insert 50, as described above. For example, in the rear region of the outer cover 28, a singularized and relatively localized fastening location providing a force-decoupled arrangement may be desirable, for the reasons described above. If an effect of this, however, is an undesirable loss of corner support and support for standing cuffs, an end support stiffener may be desirable in conjunction with a singularized/localized fastening system.

It may be desired that the portions of insert 50 including one or more end support stiffeners 60, 62 are sufficiently stiff to effectively resist the tension forces in standing cuffs 53 and substantially maintain standing cuffs 53 and edges 58 thereof in their gasketing configurations while insert 50 is in use, and substantially maintain the corners of insert 50 in laterally extended positions, preventing buckling or bunching of the same. The amount of added stiffness desired may depend upon various factors including the inherent stiffness of the insert materials without a supplemental end support stiffener, and the amount and/or range of tension in the standing cuffs when the article is worn, and the distance between the laterally outermost outside edge of the laterally outermost fastener component and the nearest longitudinal edge of the insert. At the same time, for purposes of wearer comfort, it may be desirable that the portions of the insert including the one or more end support stiffeners 60, 62 are pliable enough to flex comfortably with the wearer's body movements, and to yield or collapse before a substantial potential for contusion, abrasion, or irritation is presented. It also may be desirable that stiffened portions are elastic in nature, in that they will tend to return to a particular shape (e.g., substantially flat or planar) configuration after being bent, folded or twisted. Thus, an end support stiffener may be formed of an elastomeric polymer material.

FIGS. 2O and 2P schematically depict two possible variations for an end of an insert 50 having standing cuffs 53 with free edges 58. FIG. 2O depicts an end having a laterally centralized, singularized fastener component 56. FIG. 2P depicts an end having two fastener components 56, laterally separated and disposed near the corners of the insert. In these figures, $W_i$ is the greatest width across the insert not including an end support stiffener; $W_f$ is the portion of the width $W_i$ between the laterally outermost extents of the fastenably effective portions of the fastener components; LUD (laterally-outboard unsecured dimension) is the portion of the width $W_i$ that lies laterally outside the laterally outermost extents of the fastenably effective portions of either fastener component; and CUD (central unsecured dimension) is the portion of the width $W_i$ that lies between the laterally innermost extents of fastenably effective portions of two laterally separated fastener components. (For purposes herein, "fastenably effective portion" means any portion of a fastener component that effectively force-couples a portion of the width of an insert to an outer cover.) $L_{is}$ is the longitudinal dimension of an end support stiffener measured from the longitudinally outermost edge of the stiffener, to the longitudinally innermost extent (i.e., nearest lateral axis 70) of the stiffener.

Without intending to be bound by theory, it is believed that the following combinations of dimensions $W_f$, LUD, CUD, and/or bending stiffness for an insert end may be effective to strike a satisfactory balance among attributes including user convenience, fit, structural support, integrity and containment function for the insert and standing cuffs, and wearer comfort. Where the terms "Peak Edge Deflection Force (y)" or "Edge Deflection Force (y)" are used below, "y" is the lateral dimension in millimeters of distance 1010 as described in the Edge Deflection Force Measurement Method and depicted in FIG. 6A herein.

Insert End Bending Stiffness Regardless of Fastener Component Configuration

- The insert end has a Bending Stiffness of at least about 100 N/m, or more preferably, respectively, at least about 200, 300 or 400 N/m; or alternatively, a Bending Stiffness of between about 200 and about 500 N/m.
- The insert end has an end support stiffener and has a Bending Stiffness of at least about 100 N/m, or more preferably, respectively, at least about 200, 300 or 400 N/m; or alternatively, a Bending Stiffness of between about 200 and about 500 N/m.
- The insert end has an end support stiffener and the end support stiffener has a Bending Stiffness of at least about 50 N/m, or more preferably, respectively, at least about 100, 200, or 300 N/m; or alternatively, a Bending Stiffness of between about 100 and 500 N/m.
- The insert end has an end support stiffener having an $L_{is}$ of no more than about 50 mm, and the insert end has a Bending Stiffness of at least about 100 N/m, or more preferably, respectively, at least about 200, 300 or 400 N/m; or alternatively, a Bending Stiffness of between about 200 and about 600 N/m.
- The insert end has an end support stiffener having an $L_{is}$ of at least about 10 mm, and the insert end has a Bending Stiffness of no more than about 1,000 N/m and more preferably no more than about 500 N/m.
- The insert end has an end support stiffener having an $L_{is}$ of no more than about 50 mm, and the stiffener has a Bending Stiffness of at least about 50 N/m, or more preferably, respectively, at least about 100, 200 or 300 N/m; or alternatively, a Bending Stiffness of between about 100 and about 500 N/m.

Insert End Bending Stiffness and Peak Edge Deflection with Non-Zero LUD

- The insert end has an LUD which is greater than zero (0) and has a Peak Edge Deflection Force (30) of at least about 0.50 N, more preferably, respectively, at least about 0.60 N, about 0.70 N, about 0.80 N, about 0.90 N, or about 1.0 N, or alternatively, between about 0.50 N and about 1.0 N.
- Neither LUD at an insert end exceeds about 40 mm, and the insert end has a Bending Stiffness of at least about 200 N/m, more preferably at least about 300 N/m.
- The insert end has an LUD of at least about 40 mm and the insert end has a Bending Stiffness of at least about 300 N/m, more preferably at least about 400 N/m.
- The insert end has an LUD of at least about 5 mm and a Bending Stiffness of at least about 200 N/m, more preferably 300 N/m, even more preferably 400 N/m.

The insert end has an end support stiffener, has an LUD of at least about 40 mm, and has a Bending Stiffness of at least about 300 N/m, and even more preferably 400 N/m The insert end has an end support stiffener, has an LUD of at least about 40 mm, and the end support stiffener has a Bending Stiffness of at least about 50 N/m, more preferably 100 N/m, more preferably 200 N/m, and even more preferably 300 N/m.

The insert end has an LUD of at least about 40 mm and has an end support stiffener located in at least a portion of the insert end region comprising the LUD, the end support stiffener having a Bending Stiffness of at least about 50 N/m, more preferably 100 N/m, more preferably 200 N/m, and even more preferably 300 N/m.

The insert end has an end support stiffener and has an LUD of at least about 5 mm, and the end support stiffener has a Peak Edge Deflection Force (30) of at least about 0.2 N, more preferably, respectively, at least about 0.3 N, about 0.5 N, 0.7 N, or about 1.0 N.

Insert End Bending Stiffness with Non-Zero CUD

The insert end has a CUD of no more than about 100 mm, more preferably no more than about 80 mm, more preferably no more than about 60 mm, or alternatively, a CUD of from about 30 mm to about 80 mm, and a Bending Stiffness of at least about 200 N/m, more preferably at least about 300 N/m.

The insert end has a CUD of at least about 5.0 mm, more preferably at least about 10 mm, 20 mm, even more preferably at least about 50 mm, and less than about 80 mm; and a Bending Stiffness of at least about 300 N/m, more preferably about at least about 400 N/m, and no more than about 500 N/m.

The insert end includes a stiffener and has a CUD of no more than about 100 mm, more preferably 80 mm, even more preferably 60 mm, or alternatively, a CUD of from about 30 mm to about 80 mm, and has a Bending Stiffness of at least about 50 N/m, more preferably 100 N/m, and even more preferably 200 N/m.

The insert end has a CUD of at least about 5.0 mm, more preferably at least about 20 mm, even more preferably at least about 50 mm, and has a Peak Edge Deflection Force (30) of at least about 0.2 N, more preferably 0.5 N, and even more preferably 0.7 N.

Outer Cover and Insert Fastener System Selection

As discussed above with reference to FIGS. 2A and 2B, to enable fastening of fastening ears 29 to front region 27, fastening ears 29 may have outer cover fastener components 30 disposed thereon. Alternatively, or in addition, front region 27 may have disposed thereon one or more receiving fastener components 31 disposed thereon. Fastener components 30, 31 may be selected so as to be cooperative to effect disengageable and re-engageable, or refastenable, fastening of ears 29 to front region 27. Such a fastening system may be included to enable a user to secure the outer cover 20 about the lower torso of a wearer, to adjust the fit of the article, to enable opening and reclosing/refastening so the user can inspect the interior of the article for soiling, etc., and to enable a non-destructive removal, change of inserts, and refastening of the article about the wearer's lower torso following a change. Generally, the laterally outboard portions of the rear region 28 on each side such as fastening ears 29 may be removably and refastenably attached to the front region 27 on the corresponding side, and may removably and refastenably attach to a fastener engaging area including a receiving element 31. While various types of fastening systems may be employed, a hook and loop type fastening system has advantages, as explained above. Where fastening elements 30 are each a patch of hooks and receiving element 31 is a patch of loops material, the article may be secured about the wearer's lower torso by pressing fastening ears 29 and fastening elements 30 against receiving element 31, in appropriate locations selected to provide a suitably comfortable and snug fit.

Hook and loop systems also may be deemed desirable for purposes of attaching and holding an insert 50 within an outer cover, as discussed above, to keep it in the desired orientation and location within and relative to the outer cover during wear.

Although a variety of available hook and loop fastening systems may be selected, it may be desirable to select a combination of hook and loop components for the outer cover that, when fastenably engaged, provide sufficient holding force to resist disengagement under forces imposed on the article by the wearer's body motions, by friction from interaction with and relative movement by outer clothing, by added weight of the wearer's bodily exudates, or attempts that may be made by some wearers to pull at, unfasten or remove the article at times undesired by the caregiver.

The holding force requirements for fastening systems holding the insert within the outer cover may be different, and may be less demanding, than those for fastening the outer cover. The two-piece wearable article described herein may be designed such that the outer cover 20, rather than the insert 50, generally provides the greater share of the structural support that holds the insert 50 against the wearer's body so that exudates are effectively contained. The outer cover 20 may be designed to sustain most of the forces resulting from the wearer's movements and weight of exudates. The fastening system(s) that hold the insert 50 within the outer cover 20 may be substantially or entirely covered by the outer cover 20 during wear, such that they are less likely to be exposed to forces from friction, catching on external objects, or tugging by the wearer. Thus, the fastening system(s) that hold insert 50 within outer cover 20 may be required only to maintain location/placement of the insert within and relative the outer cover, and not provide substantial structural support to hold insert 50 in place against the wearer's body. Fastening system(s) holding insert 50 in place may need only to have suitable resistance to disengagement by shear forces between the outer cover and the insert—a function for which hook and loop systems are generally well-suited and effective.

A fastening system holding the insert within the outer cover, having the same degree of holding force as the outer cover fastening system, may also be undesirable. If the outer cover fastening system has a relatively high holding force and the same fastening system is used to hold the insert within the outer cover, this may cause the insert to be unduly and undesirably difficult to remove when the user wants to change inserts. This may be particularly inconvenient and aggravating to the user when the insert is heavily soiled with contained exudates, since it may increase the risk that the user, tugging with substantial force to remove the insert from the outer cover, may undesirably lose control and containment of the exudates and soil his or her hands or surrounding objects. It will be appreciated, therefore, that it may be desirable that the insert-to-outer fastening system be as easy to remove as possible while still satisfying structural performance requirements.

A Vertical Pull Test (VPT) as described below may be used to assess the holding force performance of hook and loop fastening system combinations. At least two parameters measured by the VPT may be important in this context: Vertical Peak Load/Engagement Area, which is a measure of the force required to completely disengage an engaged fastening combination per unit engagement surface area, and the Vertical Load at 0.5 mm Vertical Displacement/Engagement Area, which is a measure of the force required to begin a disengagement process, per unit engagement surface area. The Vertical Peak Load and Vertical Load at 0.5 mm Vertical Displacement are measured for purposes herein at a Shear Displacement of 1.00 mm.

For an outer cover 20 fastening system comprising a hook and loop system, i.e., wherein fastening element(s) 30 and receiving element(s) 31 are hooks material and loops material, respectively, it may be desired that the Vertical Peak Load/Engagement Area sustained by a fastening component pair forming the system be at least 0.045 N/mm$^2$, in order to adequately resist accidental or unintentional disengagement of the fastening system while the article is being worn, such as by an infant tugging at an edge of, e.g., an ear fastened by the system. At the same time, it may be desired that the Vertical Peak Load/Engagement Area sustained by the system be no more than 0.076 N/mm$^2$, so that the article is not excessively difficult for the user to intentionally remove. Similarly, it may be desired that the Vertical Load at 0.5 mm Vertical Displacement/Engagement Area sustained by an outer cover fastening system is at least 0.0015 N/mm$^2$ but no more than 0.015 N/mm$^2$, to strike a balance between providing suitable resistance to unintentional disengagement, and providing ease of intentional disengagement. These values may be suitable for articles of the type described herein, intended for infants and young children in ordinary circumstances. It will be appreciated, however, that differing values may be selected for differing circumstances, e.g., extremely active children; larger, stronger, older and more active children suffering from childhood enuresis who may wear such articles; adults suffering from incontinence who may wear such articles, design of articles with very small or very large fastening system contact areas, etc.

For an insert-to-outer cover fastening system comprising a hook and loop system, i.e., where one or both of fastening pairs 56, 33 and 57, 32 (e.g., FIGS. 2E-2N) are hooks material and loops material, respectively, it may be desired that the Vertical Peak Load/Engagement Area for such pair be at least 0.0061 N/mm$^2$ or even at least 0.015 N/mm$^2$, but no more than 0.030 N/mm$^2$, and usually less than the Vertical Peak Load of the outer cover fastening system. Similarly, it may be desirable that the Vertical Load at 0.5 mm Vertical Displacement/Engagement Area of such an insert-to-outer cover fastening system pair be less than the same value measured for an outer cover fastening system.

The holding force values discussed above reflect the relative holding force per engagement surface area of a hook and loop fastening component pair, and also reflect a level of resistance the pair may have to incremental disengagement by peeling away. It may also be desired to optimize suitable absolute holding force values. For any fastening component pair comprising a given type of hooks and loops, absolute holding force values may be adjusted by adjusting the engagement surface area, i.e., the area of engagement of the hooks material with associated loops material. Thus, for an outer cover fastening system component pair, it may be desired that the surface area of engagement of hooks material to loops material be from 650 mm$^2$ to 1,300 mm$^2$.

In addition to holding force, hook-and-loop fastening systems have acoustic attributes. Persons familiar with such systems will appreciate that disengaging a hook and loop fastener (typically performed by peeling the hooks component away from the loops component, or vice versa) generates a sound similar to a ripping or tearing sound, caused by sudden rapid movements within the respective materials as individual hooks and loops let go of each other under a separating force. The volume and frequencies of the sound generated will depend upon the properties and features of the substrates underlying the hooks and loops, and the design and tenacity of the hooks and loops.

Diapers are often changed while wearers, such as young babies, are sleeping. A caregiver may desire to remove a soiled article and replace it with a clean one during sleep periods to ensure comfort, protect the wearer's skin health and protect against soiling of bedclothes or other objects in the wearer's sleeping environment. The noise generated by some types of hook-and-loop fasteners during disengagement required to make a change can be sharp and loud enough to disturb the wearer's sleep or even wake the wearer, undesirable where a restful, uninterrupted and/or extended sleep period is desired.

In addition to being selected for having the desired holding forces, the outer cover and insert-to-outer cover fastening systems may be selected and designed so as to minimize the amount of potentially disturbing noise they generate during disengagement.

The magnitude of the sound pressure level generated by disengagement of a sample of a hook-and-loop fastening system, may be characterized, measured and reported in decibels (dB) according to the Fastener Acoustic Test method described herein. Sounds at frequencies of 400 Hz or more may be more significant, as they fall more squarely within the range of frequencies audible and potentially disturbing to humans.

The sound pressure level at the frequency closest to 500 Hz as measured and recorded in the Fastener Acoustic Test described below, generated by disengagement of an outer cover fastening system is preferably no greater than 40 dB, more preferably no greater than 38 dB or even 35 dB. The sound pressure level at the frequency closest to 1,000 Hz as measured and recorded in the Fastener Acoustic Test, generated by disengagement of an outer cover fastening system is preferably no greater than 40 dB, more preferably no greater than 38 dB or even 35 dB. The sound pressure level at the frequency closest to 2,000 Hz as measured and recorded in the Fastener Acoustic Test, generated by disengagement of an outer cover fastening system is preferably no greater than 50 dB, more preferably no greater than 46 dB or even 40 dB.

The sound pressure level of the insert-to-outer cover fastening system may be greater than the sound pressure level of the outer cover fastening system, because, once the outer cover bearing the insert is removed from the wearer, the insert may be changed at a location that is remote from the wearer. Nevertheless, an insert may typically be changed in the same room as that in which the wearer is sleeping, or otherwise in reasonably convenient proximity to the wearer, and so it may still be desirable to select an insert-to-outer cover fastening system with noise generation limits in mind. Accordingly, the sound pressure level at the frequency closest to 500 Hz as measured and recorded in the Fastener Acoustic Test described below, generated by disengagement of an insert-to-outer cover fastening system, is preferably no greater than 45 dB, and more preferably no greater than 40 dB. The sound pressure level at the frequency closest to 1,000 Hz as measured and recorded in the Fastener Acoustic Test, generated by disengagement of an insert-to-outer cover fastening system, is preferably no greater than 45 dB, and more preferably no greater than 40 dB. The sound pressure level at the frequency closest to 2,000 Hz as measured and recorded in the Fastener Acoustic Test, generated by disengagement of an insert-to-outer cover fastening system is preferably no greater than 40 dB SPL, and more preferably no greater than 35 dB SPL.

All hook-and-loop fastening systems currently manufactured, as might be selected, sized and applied to an outer cover and outer cover/insert article, will not necessarily satisfy some or all of the holding force and sound generation criteria set forth above. However, suitable materials that can serve as components of hook-and-loop fastening systems that satisfy some or all of these criteria are readily available and may be selected and sized by persons of ordinary skill in the art, through routine experimentation. An example of hook and loop fastening combination that may satisfy one or more of the criteria set forth for the outer cover fastening system includes nylon sewable hooks material sold under the designation ETN-21, and loops material known as Soft Tricot Fabric Loop, by Perfectex Plus, LLC, Huntington Beach, Calif. An example of hook and loop fastening combination that may satisfy one or more of the criteria set forth for the insert-to-outer cover fastening system includes hooks material sold by Aplix, S.A. Paris, France (and U.S. affiliate Aplix, Inc. USA) under the designation 960E, and loops material known as Standard Sew On nylon fabric loops material, by TouchTape, Inc., St. Augustine, Fla.

Targeting, Orientation and Alignment Indicia

As discussed above, an insert 50 may be imparted with features that make it asymmetric about its lateral axis. Despite such asymmetrical configuration, as suggested by FIG. 4, insert 50 may have an overall profile that does not appear to be asymmetric about its lateral axis. For example, as depicted in FIG. 4, insert 50 may have an overall profile, when opened and laid flat, that is substantially rectangular, and thus, appears to be symmetric about its lateral axis 70. Other insert profiles are possible as well, which have overall profiles which appear symmetric about a lateral axis. Additionally, even where an insert 50 has an overall profile that is asymmetric about its lateral axis, it may not be clear just from the profile which portion is the forward portion and which portion is the rearward portion. Thus, absent a sufficiently perceptible signal indicating which portion of the insert is the forward portion and which portion is the rearward portion, a user may have difficulty determining the same, and as a result, may attempt to install an insert into an outer cover with incorrect relative front-rear orientation—in turn, resulting in sub-optimal fit, appearance, exudate containment and/or comfort.

The insert and/or outer cover may comprise one or more insert targeting indicia to indicate, facilitate and/or compel correct positioning and association of portions of the insert within the outer cover. The insert targeting indicia may comprise verbal or non-verbal instructive indicia, visual targeting indicia, cooperating geometrical features, cooperating types of fastener components, or cooperating designs of fastener components sized and formed to indicate or compel the engagement of the insert with the correct region of, and in correct orientation with, the outer cover so as to enable the optimum performance of the wearable absorbent article. Other examples of possible targeting indicia components include one or more cooperating colors, shapes, patterns, lines, outlines, silhouettes, other geometrical features, protrusions or depressions, textures, patterns, targeting lines or crosshairs, bulls-eye representations, and the like, disposed on the outer cover and/or the insert to indicate correct positioning of the insert within the outer cover. In one example, the inner surface of the outer cover may be imprinted or otherwise marked with an outline of an insert, or a silhouette of an insert, or a portion thereof, as illustrated in FIG. 2M (corner outline images 80). In other examples depicted in FIGS. 2Q, 2S and 2T, one or more portions of an insert 50 such as a grasp tab 59 may have a targeting indicium in the form of hole, window or other profile 59a thereon or therethrough, and the inside of the outer cover 29 may have a corresponding targeting indicium thereon such as a dot or other image 59b which is visible through and/or aligns with the profile 59a when the insert is properly positioned within the outer cover. Alternatively, one or both of the forward and rearward regions 54, 55 of the insert may have disposed thereon a pictogram showing the outer cover shape, or a generalized version thereof, with the front and back of the outer cover indicated via size, color, contrast, or some other indicator, showing the correct insert installation orientation. For example, an outer cover pictogram disposed in the rearward region 55 of the insert may have the rear outer cover region, or portions thereof, indicated with a brighter color, an arrow, a circle, etc., while an outer cover pictogram disposed in the forward region 54 of the insert may have the front outer cover region, or portions thereof, indicated similarly.

Targeting indicia also may comprise at least two cooperating components, one on the outer cover 20 and one on insert 50, such that when these two components are associated, the respective components of outer cover/insert system will be properly oriented with respect to one another and will perform most optimally. In one example, the inner surface of the outer cover may be imprinted with a first arrow pointing at an insert location, and the insert may be imprinted with a second arrow pointing at the first arrow when the insert and outer cover are correctly relatively positioned.

Indicia may be cognitively correlating, or non-correlating, a correlation indicating a correct optimal placement, and a non-correlation indicating an incorrect sub-optimal placement. Respective cognitively correlating targeting indicia may include an indicium on the outer cover that cognitively correlates with an indicium on the insert, indicating to the user the correct relative positioning and engagement of the insert and the outer cover. For example, respective cognitively correlating indicia on the insert and outer cover may have a common color, shape, or texture. (As used herein, "common color" includes any first color and recognizable shades or variants thereof, which in view of all features of the article is visibly and cognitively distinguishable from another color on the article.)

Referring to FIGS. 2B, 3 and 4, when an insert 50 is asymmetrical as described above, it may have only one optimal forward region 54 and only one optimal rearward region 55. Similarly, when an outer cover 20 is asymmetrical as described above, it may have only one optimal front region 27 and only one optimal rear region 28. Thus, in the event either or both of these asymmetries are substantial, installation of insert 50 into outer cover 20 with incorrect relative front-rear orientation may cause the wearable absorbent article not to fit and/or function optimally. Accordingly, it may be desirable in some circumstances to incorporate one or more indicia into the outer cover 20 and/or insert 50 that are adapted to inform the user as to the correct respective front-rear orientation of these components. Such indicia may provide such information to the user functionally, tactilely and/or visually.

Functional indicia may include fastener components that function properly, effectively and/or optimally with correct front-rear orientation, but do not function properly, effectively and/or optimally with incorrect front-rear orientation.

For example, referring to FIGS. 2B and 3, front insert fastener component 33 on outer cover 20 may be cooperative to effect optimal/maximum fastening security only with front fastener component 56 on insert 50, but not with rear fastener component 57 on insert 50. Similarly, rear insert fastener component 32 on outer cover 20 may be cooperative to effect optimal/maximum fastening security only with rear fastener component 57 on insert 50, but not with front fastener component 56 on insert 50.

In a more specific example conceptually appreciated from FIGS. 2K-2L, front insert fastener component 33 on outer cover 20 may include a patch of loops, while front fastener component 56 on insert 50 may include a mating patch of hooks (mating relationship indicated by hatching of components 33, 56 in FIGS. 2K-2L). Correspondingly, rear insert fastener component 32 on outer cover 20 may include a patch of hooks, while rear fastener component 57 on insert 50 may include a mating patch of loops (mating relationship indicated by absence of hatching of components 32, 57 in FIGS. 2K-2L). Thus, in this particular example, if a user mistakenly attempts to fasten rear fastener component 57 on insert 50 (loops) to front insert fastener component 33 on outer cover 20 (loops), proper or optimal fastening will not be effected, which will communicate to the user that he/she must rotate insert 50 by 180 degrees to install it with correct/optimal front-rear orientation on the outer cover.

In another specific example also conceptually appreciated from FIGS. 2K-2L, front insert fastener component 33 on outer cover 20 may include a female snap fastener component, while front fastener component 56 on insert 50 may include a mating male snap fastener component (mating relationship indicated by hatching of components 33, 56 in FIGS. 2K-2L). Correspondingly, rear insert fastener component 32 on outer cover 20 may include a male snap fastener component, while rear fastener component 57 on insert 50 may include a mating female snap fastener component (mating relationship indicated by absence of hatching of components 32, 57 in FIGS. 2K-2L). Thus, in this particular example, if a user mistakenly attempts to fasten rear fastener component 57 on insert 50 (female snap fastener component) to front insert fastener component 33 on outer cover 20 (female snap fastener component), the components will not fit properly together and proper/optimal fastening will not be effected, which will communicate to the user that he/she must rotate insert 50 by 180 degrees to install it with correct/optimal front-rear orientation.

Thus, functional indicia may include any fastener components that will function properly and/or optimally to effect fastening and maximum fastening security between insert 50 and outer cover 20 when the two are properly oriented, but will not function properly or optimally otherwise. Any different types of fastener components or systems may be combined to differentiate the forward and rearward regions of the insert and indicate correct orientation within the outer cover. Generally, with the use such functional indicia, the fastener components types in the forward region of the insert and front region of the outer cover are respectively incompatible, or significantly less effective, with the respective fastener components types in the rearward region of the insert and rear region of the outer cover. As another example of such functional indicia, the front insert fastener pair 33, 56 may be a hook and loop fastening system, while the rear insert fastener pair 32, 57 may be a snap fastening system. In another example, the front insert fastener component(s) may include a pocket or flap structure, while the rear fastener components embody a dissimilar fastening system. The front and rear insert fastening systems may comprise any two different fastening systems as disclosed herein, or as otherwise available.

In another example, functional indicia may be embodied by fastener pairs 33, 56 and 32, 57 having mutually exclusive geometries of similar or compatible fastening system types. For example, as depicted in FIGS. 2E-2F and 2G-2H, the front fastener pair 33, 56 may have a first placement and geometry, while the rear fastener pair 32, 57 may have a second placement and geometry, such that if installation of insert 50 within outer cover 20 with incorrect front-rear orientation is attempted, the fastener pairs will not align to provide visibly correct and functionally effective attachment, communicating to the user that that he/she must rotate insert 50 by 180 degrees to install it with correct/optimal front-rear orientation. In another similar example (not depicted), the front insert fastening system may have an open circle, or doughnut-like, geometry, while the rear insert fastening system may have a geometry of a circle with a diameter less than that of the central opening in the open circle of the front insert fastening system. In yet another example (not depicted), the front and rear insert fastening systems may be located primarily on one side of the longitudinal axis of the article (i.e., the longitudinal axes of both the insert and the outer cover). In this example, if the insert is applied to the outer cover in the incorrect front-to-back orientation, the insert fastener components and fastener components will not align correctly. In another example (not depicted), the front insert fastening system may comprise an interlocking fastener oriented along the direction of the longitudinal axis of the article, while the rear fastening system may comprise an interlocking fastener oriented along the direction of a waist edge or lateral axis of the article. In another example which may be conceptually appreciated from FIGS. 2E-2F, and 2G-2H the front fastening system may include one or more fastener components 33, 56 disposed along or near the longitudinal edges of the insert, while the rear fastening system may include a single fastening pair 32, 57 having a width less than the insert width and disposed on the longitudinal axis of the article.

Functional indicia need not necessarily be limited to fastener components. Functional indicia also may be embodied in other features of the outer cover and insert that affect how the two fit or function together in correct, optimal front-rear orientation versus incorrect (reverse), sub-optimal front-rear orientation. Thus, functional indicia may additionally be associated with or combined with another functional element of the outer cover or insert. Indicia may be associated with elements of the outer cover such as a waistband, side panel, stretch element, leg cuff, physical retention fastener component (e.g., a pocket or retaining strap), and the like. Indicia may be associated with elements of the insert, such as a waist cap, waist band, standing cuff, fecal management feature, insert positioning aid, insert stiffening aid, insert removal aid, or insert disposal aid.

From the foregoing it will be appreciated that other forms of functional orientation indicia are possible, within the principle of the foregoing description. Additionally, any of the differing types of indicia described may be included in a single article, in any combination.

In other possible examples, instead of respective functionally cooperative/uncooperative pairs of components as described above, insert 50 and outer cover 20 may include respective non-functional indicia, such as tactile or other sensory indicia.

For example, the front insert and outer cover fastener components may be selected or formed so as to have a first tactile attribute, while the rear insert and outer cover components may be selected or formed so as to have a second tactile attribute. In another example, features of the insert and outer cover may have features such as 3-dimensional shapes that are mating or geometrically cooperating with optimal front-rear orientation, but not mating or geometrically cooperating with reversed, suboptimal front-rear orientation.

In other possible examples, instead of or in addition to respective functionally cooperative/uncooperative pairs of fastener components or tactile indicia components as described above, insert 50 and outer cover 20 may include respective visual indicia. Outer cover 20 may include respective front and rear visual indicia 73, 74 disposed on the front region 27 and rear region 28, respectively. Respective visual indicia disposed on insert 50 and outer cover 20 may be adapted to provide a visual cue to the user of correct/optimal orientation and placement of insert 50 within outer cover 20.

For example, components of visual indicia and a visual cue may involve use of a common color. In one particular example, front and/or rear visual indicia 73, 74 disposed on outer cover 20 may comprise respective common colors visibly distinct from one another. (As used herein, "common color" includes any first color and recognizable shades or variants thereof, which in view of all features of the article is visibly and cognitively distinguishable from another color on the article.) Insert 50 may have respective cooperating indicia disposed or embodied thereon. Thus, for example, forward and rearward user grasp structures 59, 61 on insert 50 may bear or be colored with colors respectively common and corresponding with those comprised by front and/or rear visual indicia 73, 74. More particularly, for example, front visual indicium 73 and an insert feature such as forward user grasp structure 59 may both bear or be colored a first common color, and rear visual indicium 74 and a feature such as rearward user grasp structure 61 may either or both be colored a second common color, visibly distinguishable from the first common color.

In another particular example which may be conceptually appreciated from FIGS. 2I-2J, 2M-2N and 3, front and rear visual indicia 73, 74 disposed on outer cover 20 may embody, or bear images of, respective shapes or sizes to match, or cognitively correlate visually correlate with, corresponding shapes or sizes embodied, or pictured on, insert features such as forward and rearward user grasp structures 59, 61 and/or fastener components 56, 57. More particularly, for example, front visual indicium 73 or forward user grasp structure 59 may both embody or bear images of triangles, and rear visual indicium 74 or rearward user grasp structure 61 may both embody or bear images of circles. Other examples of cognitively correlating indicia respectively disposed on an insert and corresponding location on an outer cover include: a baseball and glove, soccer ball and goal, bird and nest, and any other images of components of well-recognized pairings which would indicate to a user that two portions bearing or embodying such images are to be brought together during installation of insert 50 within outer cover 20.

In another particular example, front and rear visual indicia 73, 74 disposed on outer cover 20 may bear images of words or symbolic indications for "front" and "rear", to match corresponding words or symbolic indications on insert features such as forward and rearward user grasp structures 59, 61. In a more particular example, front visual indicium 73 and forward user grasp structure 59 may both bear an image of the letter "F" (i.e., for "front"), and rear visual indicium 74 and rearward user grasp structure 61 may both bear an image of the letter "R" (i.e., for "rear").

Figure 2R:
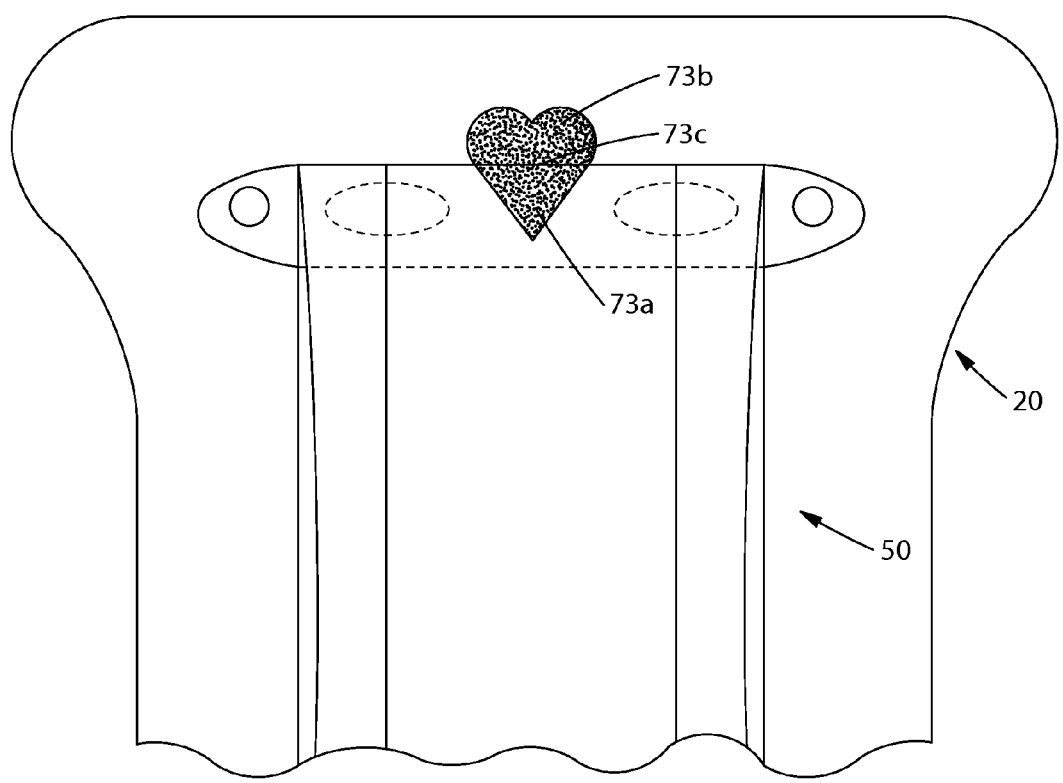
FIG. 2R is a plan view of one end of an insert opened and laid flat, inner (wearer-facing) surface facing the view, shown overlaid on an outer cover.
Figure 2S:
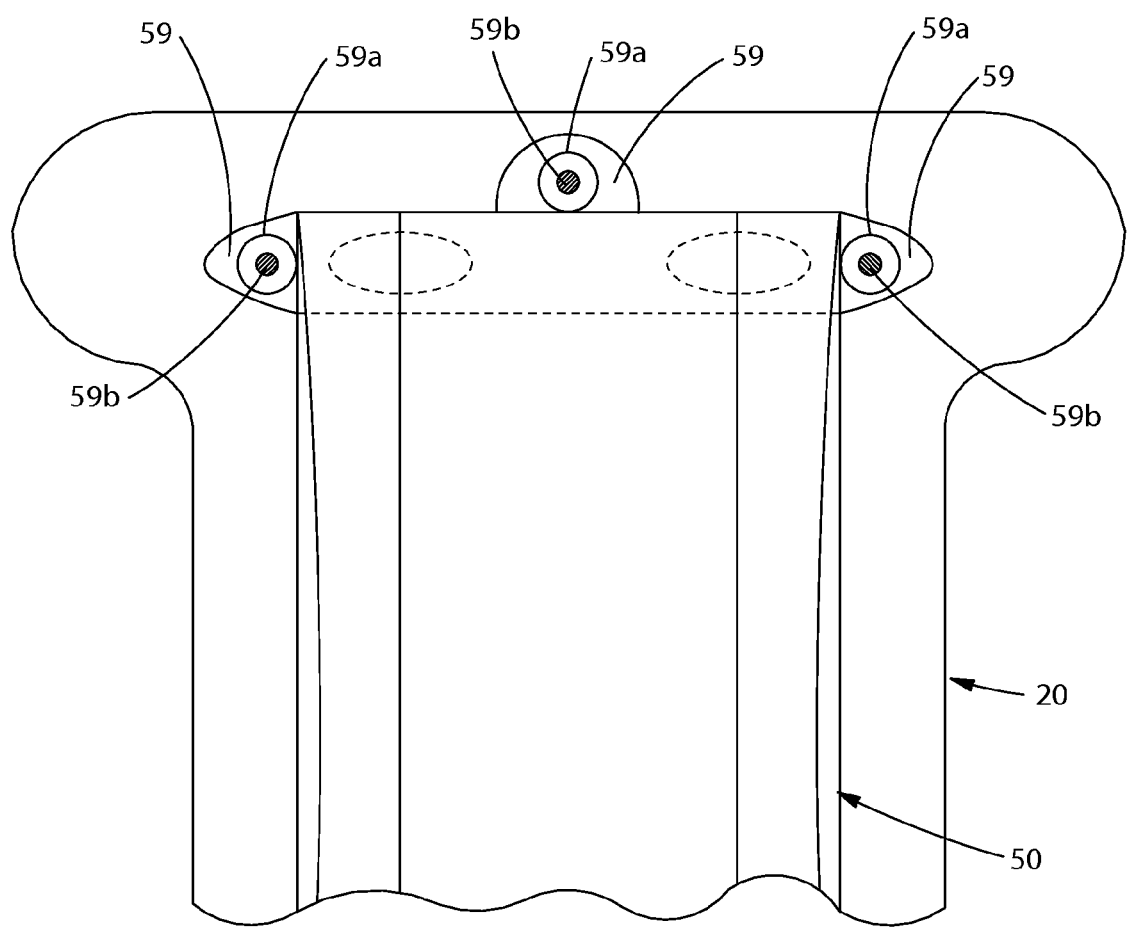
FIG. 2S is a plan view of one end of an insert opened and laid flat, inner (wearer-facing) surface facing the view, shown overlaid on an outer cover.
Figure 2T:
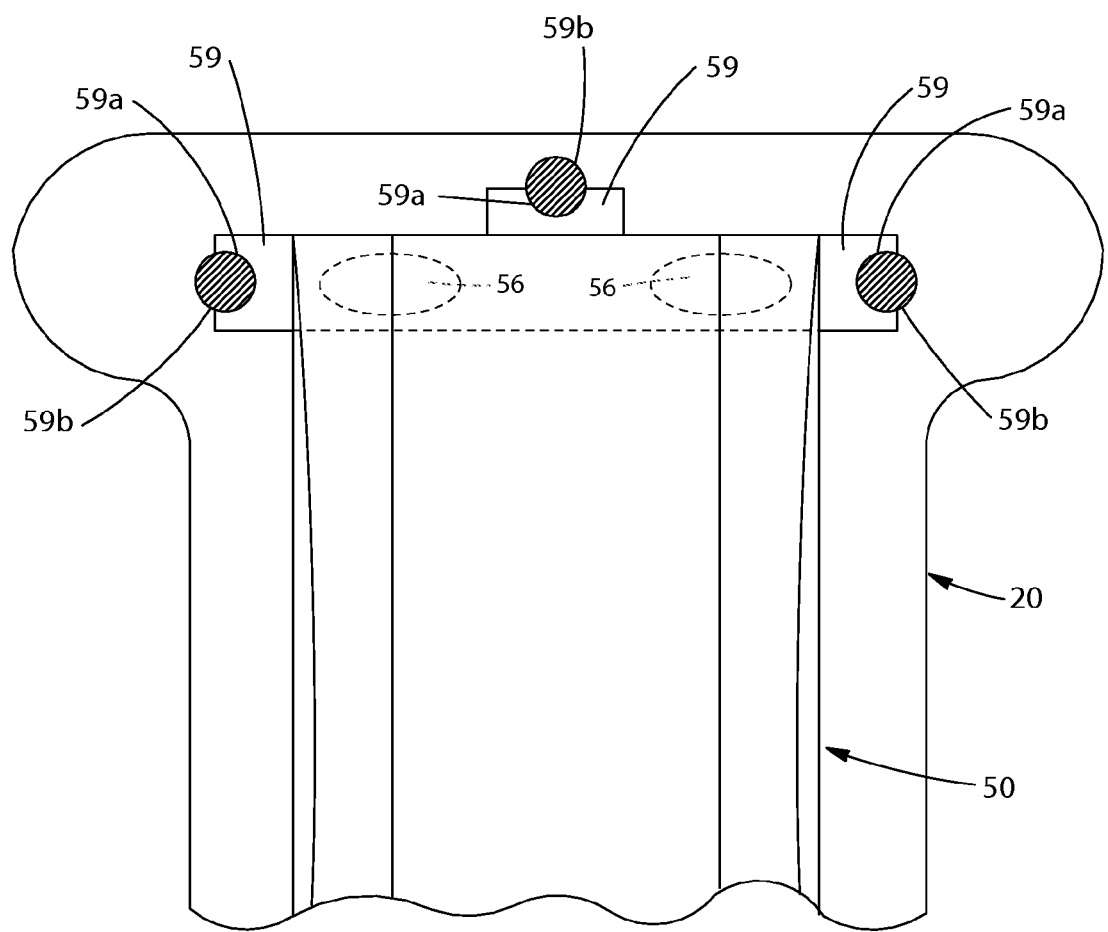
FIG. 2T is a plan view of one end of an insert opened and laid flat, inner (wearer-facing) surface facing the view, shown overlaid on an outer cover.

In another particular example, front and/or rear visual indicia 73, 74 disposed on outer cover 20 may embody, or bear images of, respective portions of expectedly user-recognizable shapes, characters, objects, etc., to match corresponding portions of expectedly user-recognizable shapes, characters, objects, etc., embodied, or pictured on, insert features such as forward and/or rearward user grasp structures 59, 61. In a more particular example, front visual indicium 73 and forward user grasp structure 59 may both embody or bear respective portions of a first image that, when brought together properly, form a cognitively complete image of an expectedly user-recognizable first shape, character, object, etc.; and/or rear visual indicium 74 and rearward user grasp structure 61 may both embody or bear respective portions of a second image that, when brought together properly, form a cognitively complete image of an expectedly user-recognizable second shape, character, object, etc., distinctive from the first. To illustrate an example, referring to FIG. 2R, a visual indicium 73a disposed on one end of an insert 50 may be a first portion of an expectedly user-recognizable image (such as a heart shape) cut off along an edge 73c of insert 50, while a visual indicium 73b disposed on an outer cover 20 may be the second portion of the same image, such the expectedly user-recognizable image is completed upon proper orientation and positioning of the insert within the outer cover such that respective indicia 73a and 73b meet and match to complete the image. It will be understood that the heart shape image depicted is but one example among any number of expectedly user-recognizable images and respective portions thereof that may serve in such manner as targeting and/or alignment indicia. The image and portions thereof may also take the form of a trademark or particular distinctive or distinguishing artwork used by the manufacturer in connection with the product.

In yet another particular example, visual orientation indicia may be simplified into a single pair of visual indicia appearing, respectively, on outer cover 20 and insert 50. In one such example, an inner surface 25 of outer cover 20 may bear an image of an arrow pointing longitudinally toward front edge 21, and insert 50 may bear an image of an arrow pointing longitudinally toward its forward end.

Examples of other suitable visual orientation indicia adapted to provide orientation information may include alphanumeric text including words, arrows, symbols, diagrams, pictographs, icons, cartoons, schematics, and any other visual indicia.

It may be desired that indicia associated with the front portions of the outer cover and insert will not cognitively correlate, or will cognitively not correlate, with indicia associated with rear portions of the outer cover and insert, and vice versa, when the user views both sets of indicia.

From the foregoing it will be appreciated that other forms of visual orientation indicia are possible, within the principle of the foregoing description.

In addition to providing indicia that indicate and/or compel the correct front-rear orientation of the insert with respect to the outer cover, it also may be desirable to provide indicia that indicate and/or compel correct longitudinal and lateral alignment of the insert within the outer cover, in order to provide for the designed optimal containment, fit, comfort and appearance of the article. In the examples shown in FIGS. 2E-2N, respective fastener component pairs 32, 57 and 33, 56 are configured and disposed to serve as alignment indicia. It can be appreciated from these examples that fastener components may be configured and disposed to not only indicate and/or compel correct front/rear orientation, but also indicate and/or compel correct longitudinal and lateral alignment of the insert 50 with respect to the outer cover 20, because co-location of one or both of these fastener component pairs to effect proper fastening will also effect proper longitudinal and lateral alignment. In other examples, separate visual indicia may be included for this purpose, such as, for example, longitudinal alignment indicia 79a, 79b and lateral alignment indicia 78a, 78b disposed respectively on outer cover 20 and insert 50 (FIGS. 2E-2F). Referring to FIGS. 2E-2F, it can be seen that insert 50 may be longitudinally and laterally aligned within outer cover 20 by ensuring that alignment indicia pairs 78a, 78b and 79a, 79b meet, or are closely proximate each other, when insert 50 is installed into outer cover 20. Visual alignment indicia may take other forms, including, but not limited to, matching line segments, shapes, insert end or corner outline images 80 disposed on the inner surfaces of outer cover 20 (see, e.g., FIGS. 2M-2N), etc.

Article of Commerce

It is contemplated that an article of commerce including one or a plurality of outer covers and one or a plurality of inserts, as described herein, may be prepared and sold as such. For example, a package containing from one to 12, or more, outer covers, together with one or a plurality of associated inserts, may be assembled and sold together as packaged. The respective outer cover(s) and inserts in a package may have matching/complementary fastening systems, orientation indicia and/or alignment indicia as described herein.

For such an article of commerce it may be desirable to determine a ratio of inserts to outer covers suitable to constitute a set of convenient numbers of outer covers and inserts, respectively. For example, it may be deemed suitable to include approximately a half day or day's supply of inserts for each outer cover included in the set. Thus, for example, the article of commerce may include inserts and outer covers in a ratio of inserts to outer covers of 1:1, 2:1, 3:1, 4:1, 5:1 or even 6:1. Accordingly, for example, a package associating a set may include one outer cover and 1, 2, 3, 4, 5 or 6 inserts; two outer covers and 2, 4, 6, 8, 10 or 12 inserts; three outer covers and 3, 6, 9, 12, or 18 inserts, and so on. For a "starter" set for certain consumers such as first-time purchasers, or in other circumstances, it may be desirable for a package to contain from 2 to 14 outer covers—which may correspond roughly to from one day's to one week's supply of clean outer covers available before laundering becomes necessary.

It may also be desirable to include, in a set including a plurality of inserts, inserts of differing designs, adapted for use under differing circumstances. In one example, one or more of the inserts in the plurality may be adapted for extended or nighttime use (sleep-use), and one or more for daytime use, with respect to features such as, e.g., location of absorbent material and absorbent capacity. Half of the number of inserts in the plurality, or fewer than half, may be adapted for sleep-use. In one example of this embodiment, the set also may include one or more outer covers decorated with nighttime/sleep themes, such as, for example, images of the moon, stars, nighttime sky colors and other nighttime scenes, images of sleeping animals, sleeping people, sleeping anthropomorphic characters, etc.; and one or more outer covers decorated with daytime/play themes, such as, for example, sun, birds, bright colors, daytime sky colors and other daytime scenes, images of awake/playing animals, people, anthropomorphic characters, etc.

In a further embodiment, a set in a package may be specially adapted for either boys or girls. For example, a package may include one or more outer covers having surface decoration and ornamentation associated with little girls, e.g., inclusion of pink, lavender and/or other soft pastel color schemes, images of flowers, butterflies, bunnies, kittens, little girls, princesses, feminine cartoon characters or feminine anthropomorphic characters, etc., or other decorative features generally associated with little girls. Conversely, a package may include one or more outer covers having decoration and ornamentation associated with little boys, e.g., inclusion of blue, black, dark or bold color schemes, images of cars, trains, planes, boats, rockets, spaceships, objects associated with sports, little boys, masculine cartoon characters or masculine anthropomorphic characters, etc., or other decorative features generally associated with little boys. A package designed for either boys or girls also may include associated corresponding inserts specially adapted for either boys or girls, whether by functional elements or by non-functional, ornamental/decorative elements. Alternatively, a package may contain one or more outer covers and inserts adapted for use with either boys or girls, having gender-neutral decoration/ornamentation and functional elements.

In a further embodiment, a set in a package may include several types of inserts, having functional designs that differ in other respects. For example, a package may include one or more inserts having one or more of a feces acceptance aperture in a topsheet, space beneath the topsheet for isolation of feces, and/or related features such as described in, for example, co-pending U.S. application Ser. Nos. 11/224,779, 11/786,890 and 11/894,087.

In a further embodiment, a set in a package may be specially adapted for use in specific circumstances. For example, a set may include one or more outer covers and associated inserts adapted for wearing while swimming or public bathing. In this example, the outer cover(s) and inserts may be adapted for satisfactory use and to substantially retain structural integrity while soaked and/or immersed in water. For example, the included outer cover(s) may be constructed of materials which do not substantially lose tensile strength, stretch or sag when soaked. In this example, it may be desirable to form the outer cover(s) predominately of polymeric, hydrophobic materials and/or elasticized textile materials. Similarly, it may be desirable to form included inserts of materials that will withstand immersion and soaking without substantial loss of structural integrity during the period of intended use. It also may be desirable to form such inserts without inclusion of superabsorbent polymer or absorbent gelling material. While these absorbent materials are often included in the absorbent cores of regular diapers, they may be deemed unsuitable for use in articles to be worn while swimming or bathing, because such materials would quickly absorb water, and swell and bulge with the absorbed water, upon being immersed—giving up their absorptive capacity, adding bulk and weight, and retaining no benefit. Within the same set, however, one or more inserts may be included for non-swimming, non-bathing use, such that the same outer cover(s) may be used for swimming/bathing and non-swimming, non-bathing activities. The one or more inserts for non-swimming, non-bathing use may have absorbent cores including superabsorbent polymer or absorbent gelling material.

In a further embodiment, a set in a package may contain a plurality of durable outer covers 20, having leg openings defined by leg opening edges 23 that differ in dimension from one durable outer cover to another durable outer cover. Sequential use of such durable outer covers may be useful to effect a change in the location(s) at which leg band portions 36 and leg opening edges 23 encircle and contact the wearer's skin, each time a durable outer cover in the plurality is replaced by another durable outer cover in the plurality having such differing dimensions. This may provide the advantage of reducing the likelihood or severity of chafing of the wearer's skin in the location(s) of such contact that may result from the wearer's movements. Such chafing may otherwise be caused or exacerbated by repeated use of successive durable outer covers having leg openings of substantially unchanging dimensions, which may result in repeated encircling contact with the skin in a more concentrated or localized fashion. Thus, for example, a user may apply a first durable outer cover in the plurality and the wearer may wear it for a first period of time (such as a day), and the user may apply a second durable outer cover in the plurality and the wearer may wear it for a second period of time (such as the ensuing night or following day), and so on—effectively varying the location(s) on the wearer's skin at which leg opening edges and leg bands encircle and contact it—and reducing the likelihood or severity of chafing. Referring to FIG. 2C, it will be appreciated that varying any of, or any combination of, outer cover crotch width $WC_c$, outer cover front width $WC_f$, outer cover rear width $WC_r$, outer cover length LC and leg band length LLB, can have the effect of varying the size of the leg openings of a durable outer cover 20 when applied to the same wearer. Accordingly, a set of at least first and second outer cover in a package may have a difference between them in any of outer cover crotch width $WC_c$, outer cover front width $WC_f$, outer cover rear width $WC_r$, outer cover length LC or leg band length LLB, as measured with each outer cover laid out horizontally on a flat surface, extended to its fullest unstretched (relaxed) dimensions. Any of dimensions $WC_c$, $WC_f$, $WC_r$, LC or LLB may differ between the first and second durable outer covers by at least about 10%, 15%, 20% or more. In another example, however, the tension forces in leg bands 36 may be varied from one durable outer cover to the next, by use of, for example, differing types of elastic strands or strips, or differing sizes of elastic strands or strips, or differing numbers of elastic strands or strips, respectively included by leg band portions 36, or even differing constructions of leg band portions 36—any of which may effect differences in dimensions of leg opening edges 23 from one durable outer cover to another durable outer cover within the package.

In a further embodiment, a variety of packages containing a variety of types of sets may be presented as a variety of articles of commerce. In one example, one or more outer covers forming part of a set in a package may be seasonal in nature, either by reasons of function or decorative/ornamental elements or both. Distinctive sets of outer covers may differ from set to set in attributes such as material basis weight, insulation properties, breathability, etc. For example, a "winter" or "cold weather" outer cover may be formed of materials individually or in combination having a relatively higher basis weight, while a "summer" or "warm weather" outer cover may be formed of relatively lighter materials and/or materials having greater breathability (as may be characterized and compared by WVTR).

In another example, one or more outer covers forming part of a set in a first package may all have decorative/ornamental elements designed by a first designer and/or be labeled or branded with the first designer's name or brand, while one or more outer covers forming part of a set in a second package may all have decorative/ornamental elements designed by a second designer and/or be labeled or branded with the second designer's name or brand. In another example, one or more outer covers forming part of a set in a first package may all have decorative/ornamental elements and/or a label and/or a brand associated with a first particular "collection" or design theme of a designer, while one or more outer covers forming part of a set in a second package may all have decorative/ornamental elements and/or a label and/or a brand associated with a second particular "collection" or design theme of the designer.

In any of the above examples, the outer cover(s) and associated insert(s) in each individual article of commerce will be sized to fit optimally with each other. Thus, in a further example, respective packages may be prepared and presented with sets of outer cover(s) and associated insert(s) distinguished by size. For example, a first package may contain outer cover(s) and associated insert(s) adapted for "size 1" children; a second package may contain outer cover(s) and associated insert(s) adapted for "size 2" children; and so on.

Edge Deflection Force Measurement Method

Figures 6A, 6B:
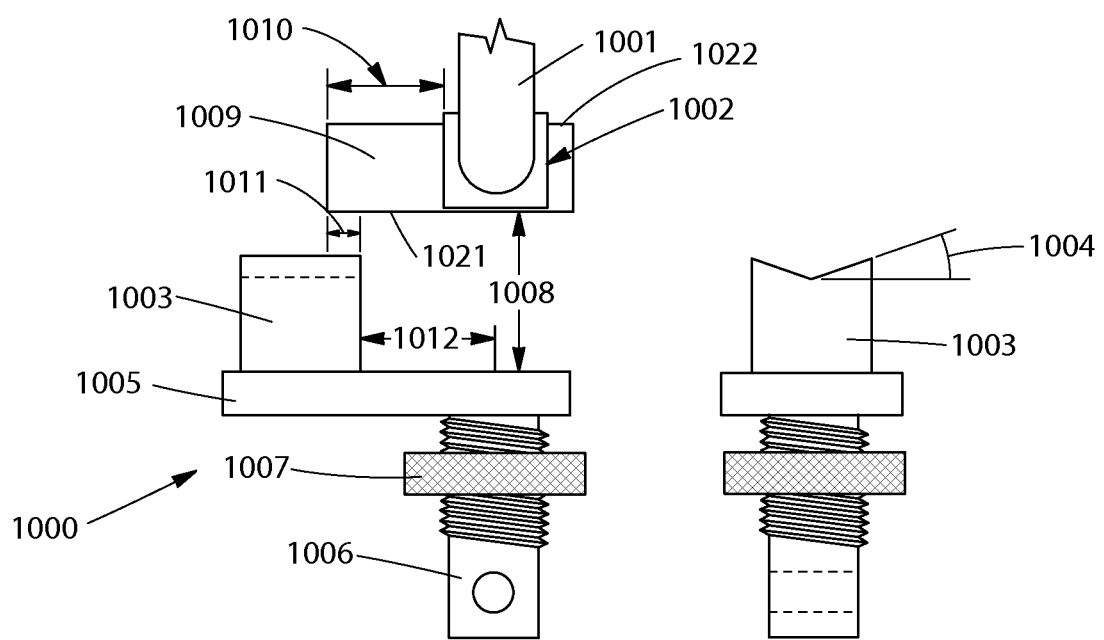
FIG. 6A is a front view of fixtures used on a constant rate of extension tensile tester for use in the Edge Deflection Force Measurement Method herein, with an included test sample.
FIG. 6B is a side view of a lower fixture used on a constant rate of extension tensile tester for use in the Edge Deflection Force Measurement Method herein.

Edge Deflection Force is measured on a constant rate of extension tensile tester with a computer interface (a suitable instrument is the MTS QTest/1L using Testworks 4.0 software, as available from MTS Systems Corp., Eden Prairie, Minn.) using a load cell for which the forces measured are within 10% to 90% of the limit of the cell. Referring to FIG. 6a, the movable (upper) pneumatic jaws 1001 are fitted with 1 inch×1 inch diamond-faced grips 1002.

The tensile tester is configured for a compression test. Program the tensile tester to lower the crosshead at a rate of 5.0 mm/min until a force of 0.01 N is detected. Zero the time and extension channels and begin data collection at an acquisition rate of 100 Hz. Lower the crosshead at a rate of 50 mm/min for 10 mm and then return the crosshead to its original gage length. From the force versus extension curve, program the software to report the peak force (N).

Referring to FIGS. 6a and 6b, the lower fixture 1000 consists of a base 1005 base 90 mm wide by 40 mm deep by 6 mm thick. The base 1005 is affixed to a suitable mounting device that includes lower mounting shaft 1006, adapted to connect to the stationary mount of the tester. Lower mounting shaft 1006 is threaded as shown and has a locking collar 1007. When the lower mounting shaft 1006 is connected to the stationary mount of the tester, the locking collar 1007 is turned against the stationary mount to immobilize the base 1005 relative the stationary mount of the tester, such that it will remain stationary with the stationary mount, without any interplay therebetween, during testing. Mounted on the base 1005 is a V notched block 1003 that is 30 mm wide by 30 mm deep by 30 mm in height which is made of a low friction material such as Teflon. Referring to the perspective FIG. 6b, the block 1003 is notched from side to center with a "V" at an angle 1004 of 10 degrees. As mounted on the base 1005, the block is centered front to back and offset a distance 1012 of 32.7 mm from the center axis of the mounting shaft 1006, with the line defined by the vertex of the "V" notch intersecting the center axis of the mounting shaft 1006.

Obtain 10 samples from 10 inserts for testing as follows: Determine which of front or rear portions of the inserts are to be tested, and take all 10 samples from such portions accordingly. Lay the insert on a horizontal surface, outer/garment-facing surface up.

(a) Samples of Insert End (Including all Layers and Components)

Figure 7:
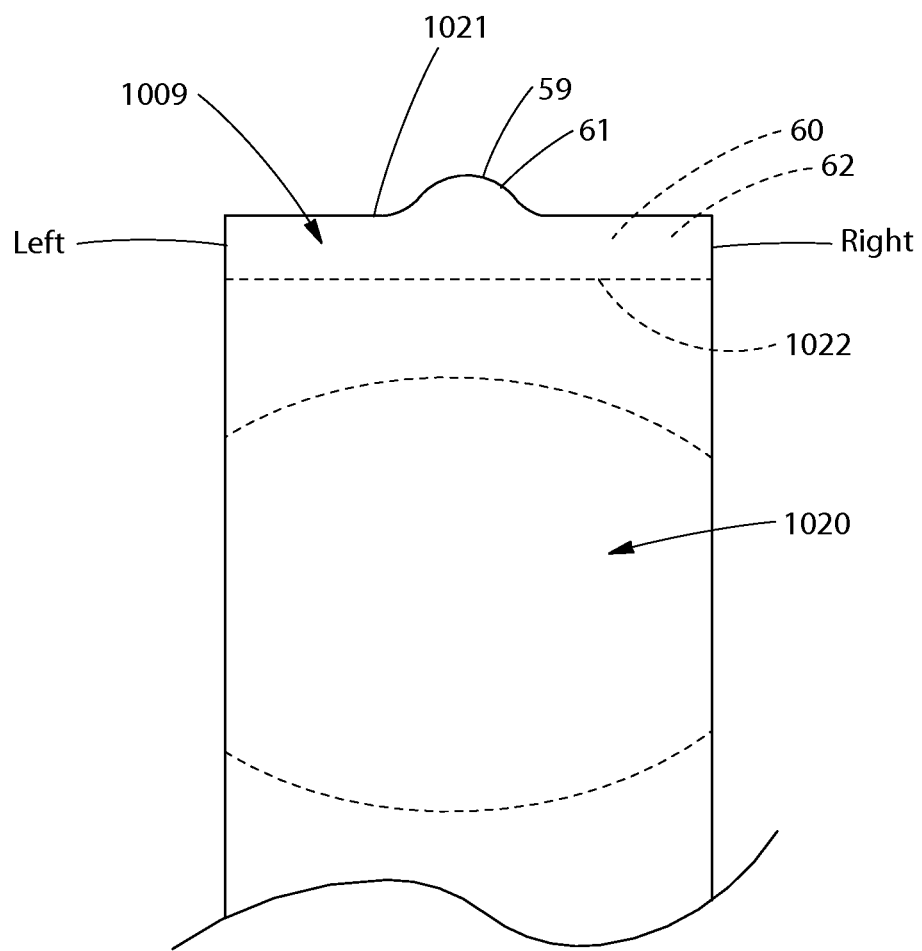
FIG. 7 illustrates preparation of a test sample of an insert including an end support stiffener, for testing in the Edge Deflection Force Measurement Method herein.

If measuring values for the insert end including all layers and components thereof, obtain samples as follows: Referring to FIG. 7, visually identify the inside edge 1022 of the stiffened portion 1009 of the end (i.e., the portion having end support stiffener 60 or 62). If visually identifying inside edge 1022 is difficult due to the particular construction of the insert, inside edge 1022 may be identified by flattening the insert along the region including the subject end, to its full longitudinal extent (stretching it out against any contraction caused by cuff elastics), laying one hand over the insert near the end to hold the insert in the stretched/flattened position, generally in the location indicated as 1020, and using the other hand to lift outer end edge 1021 vertically. The insert will tend to fold first along inside edge 1022, since a natural "hinge" location will exist at the juncture between the stiffened portion and the adjacent unstiffened portion. Cut the stiffened portion 1009 away from the insert, along edge 1022. Stiffened portion 1009 will now be the sample to be tested. (If the end portion has no stiffened portion clearly discernible by the method described above: Lay the insert on a horizontal surface, wearer-facing surface up. Considering FIG. 2O for reference, measure inward on the insert from the longitudinally end-most extent 101 of the material forming either edge 58 of cuff 53, a distance of 30 mm. Sever the end portion of the insert along a line 1023 located at such distance and parallel to the insert lateral axis. The severed portion will be the sample.) Do not remove any components such as fastener components, grasp structures, etc. If outer edge 1021 is not inherently readily distinguishable from the cut edge by a distinctive feature such as a grasp structure 59, 61, mark outer end edge 1021 for later identification.

(b) Samples of Insert End Stiffener (Removed from Insert)
If measuring values of an added insert end support stiffener by itself, obtain samples of insert ends according to the previous section (a). Apply a freeze spray as necessary to reduce the tenacity of any adhesives, and gently peel away all other components or layers of the end samples from the end support stiffener portion, taking care to avoid damaging the stiffener portion.

All testing is performed in a conditioned room maintained at about 23 C±2 C and about 50%±2% relative humidity. Precondition samples at about 23 C±2 C and about 50%±2% relative humidity for 2 hours prior to testing.

Referring to FIG. 6a for directional and positional orientation, locate a sample 1009 in the grips 1002 with inside edge 1022 horizontal and oriented upward, and outer end edge 1021 oriented downward, and in line with the bottom edges of the grips 1002. Additionally, locate sample 1009 in the grips 1002 such that distance 1010 is as designated for the Peak Edge Deflection Force (y) or Edge Deflection Force (y) value to be determined, and distance 1011 is 10 mm. Close the grips 1002 so that sample 1009 is gripped securely enough so as not to allow it to slip or rotate during testing, but not so tightly as to cause tearing of the sample at the grips during testing.

Zero the load cell and the crosshead position. Start the tensile tester's program, and record the data. Report the peak force (Edge Deflection Force) (in N) to ±0.001 N. For each sample, perform the test on both the left and right sides (see FIG. 7), and record the Edge Deflection Force for both sides. Test 10 samples. Calculate the average Edge Deflection Force found of the 10 samples, both sides.

Bending Stiffness Measurement Method

Figure 8:
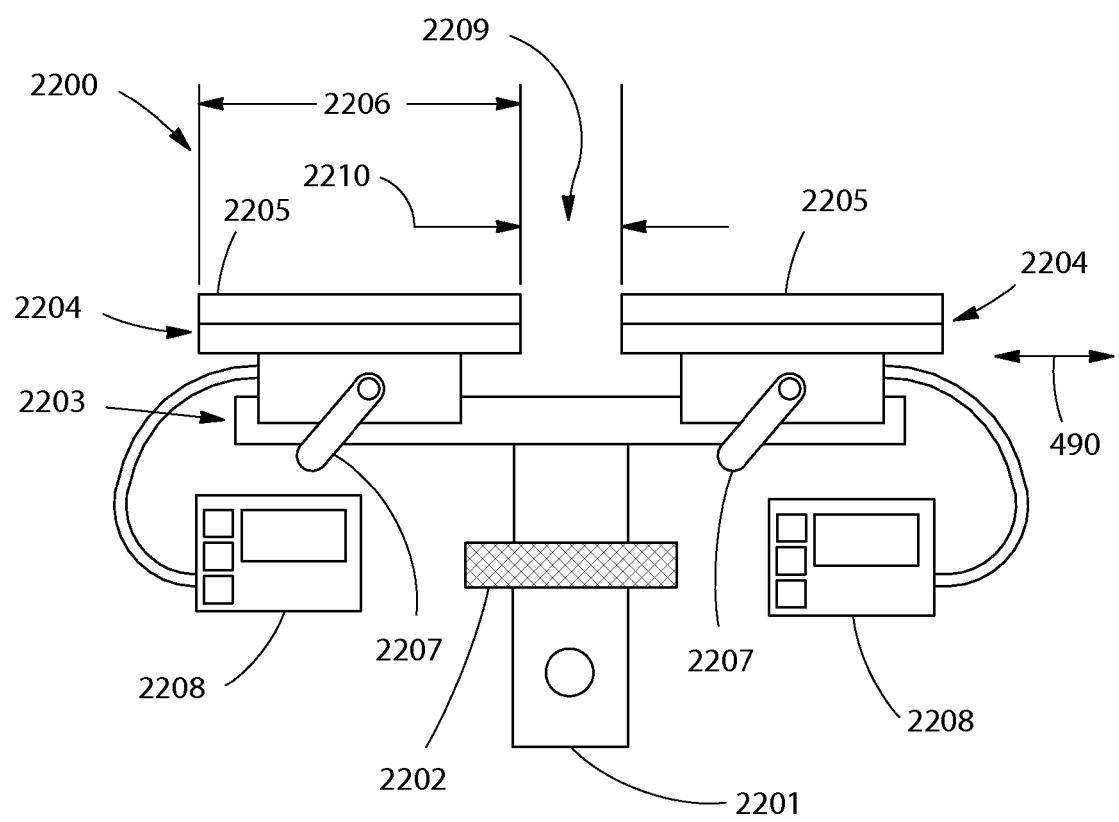
FIG. 8 is a front view of a lower fixture used on a constant rate of extension tensile tester for use in the Bending Stiffness Measurement Methods herein.
Figure 9:
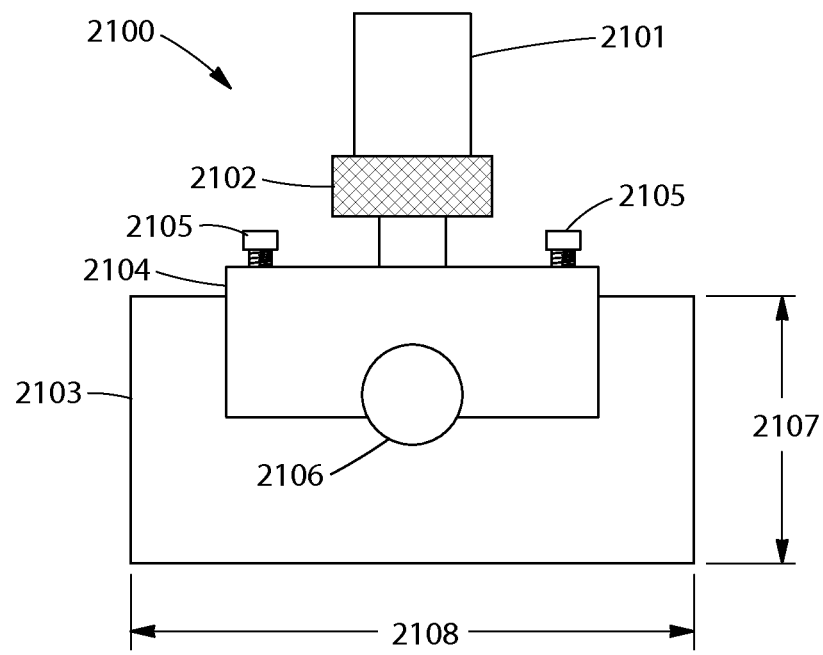
FIG. 9 is a side view of an upper fixture used on a constant rate of extension tensile tester for use in the Bending Stiffness Measurement Methods herein.
Figure 10:
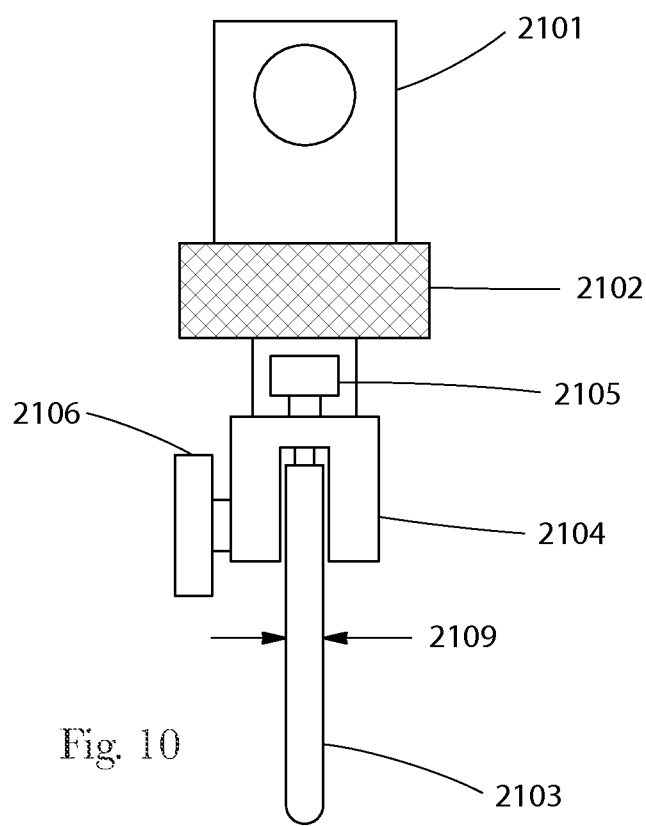
FIG. 10 is a front view of an upper fixture used on a constant rate of extension tensile tester for use in the Bending Stiffness Measurement Methods herein.

Peak Bending Force and Bending Stiffness are measured using a constant rate of extension tensile tester with computer interface (a suitable instrument is an MTS Alliance under TestWorks 4 software, as available from MTS Systems Corp., Eden Prairie, Minn.) fitted with a 10 N load cell. A plunger blade 2100, shown in FIG. 9 (front view) and FIG. 10 (side view), is used for the upper movable test fixture. Base support platforms 2200, shown in FIG. 8, are used as the lower stationary test fixture. All testing is performed in a conditioned room maintained at about 23 C±2 C and about 50%±2% relative humidity.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 3.25 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 25.00±0.02 mm between the two gap edges of the support platforms 2204, with the plunger blade 2103 accurately (±0.02 mm) centered in the gap. Program the tensile tester for a compression test. Set the gauge length from the bottom of the plunger blade 2103 to the top surface of the support platform 2204 to 15 mm.

Set the crosshead to lower at 500 mm/min for a distance of 25 mm. Set the data acquisition rate to 200 Hz.

Obtain 10 test samples 1009 as described in the description of the Edge Deflection Force Measurement Method, above. (Do not remove any components such as fastener components, grasp structures, etc., except that if any release paper is present on any adhesive fastener component, remove the release paper.) Precondition samples at about 23 C±2 C and about 50%±2% relative humidity for 2 hours prior to testing.

Examine the sample 1009 to be tested for any exposed adhesive and deactivate any exposed adhesive by applying baby powder to it as necessary. Place the sample flat onto the surface of the support platform 2204 over the gap 2209 with the wearer-facing surface facing upward. Center the sample 1009 across the gap, with edge 1022 perpendicular to the gap. Zero the load cell; start the tensile tester and the data acquisition.

Figure 11:
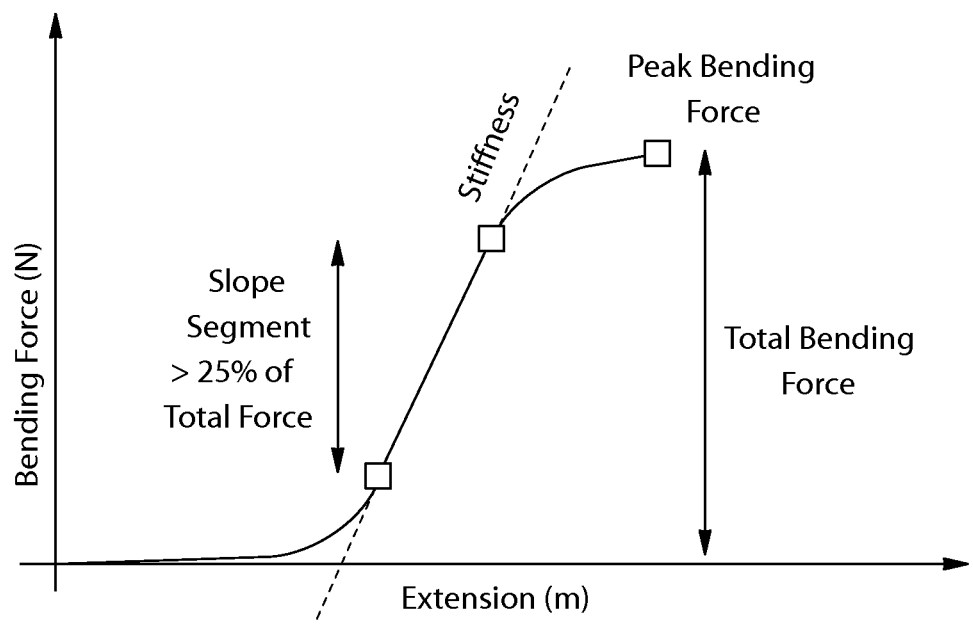
FIG. 11 is a graph showing Peak Bending Force and slope calculation areas on a bending curve.

Program the software to calculate the maximum peak bending force (N) and Stiffness (N/m) from the constructed force (N) verses extension (m) curve. Stiffness is calculated as the slope of the bending force/extension curve for the linear region of the curve (see FIG. 11), using a minimum line segment of at least 25% of the total peak bending force to calculate the slope.

Report Peak Bending Force to the nearest 0.1 N and the Bending Stiffness to the Nearest 0.1 N/m, and record the results. Repeat the test and record the results for all 10 samples. Calculate the average Peak Bending Force and average Bending Stiffness.

Vertical Pull Test

This test is designed to measure the force, displacement as a function of force (and vice versa), and/or work necessary to separate a sample of a hooks fastener component from engagement with a loops component, which components may be used to form a hook-and-loop fastening system, such as often found on wearable articles. In some instances, the loops component may be simply the materials forming the larger portions of article as well; in some wearable article designs the material alone provides a sufficiently looped, fibrous and durable surface that is effectively engageable with a hooks component, to provide the desired attachment.

Test Sample Preparation

Prepare hooks and loops material samples for testing as follows:

Loops Material
1. Identify the loops-type fastening component element of the article. (For illustrative example, referring to FIG. 2A, a loops-type components may be comprised by receiving element 31; or to FIGS. 2E-2N, in fastening elements 32, 33.)
   a) If the loops-type fastening component is formed of a layer of material applied over an underlying layer, carefully remove the layer of loops material without damaging it. Use a freeze spray as necessary to weaken bonding by any adhesives; use a sharp, fine cutting implement to sever any stitches, to facilitate separation of the loops material ("LOOPS material") from the underlying layer.
   b) If the layer forming the loops-type fastening component cannot be separated from the underlying material without damage, or if the loops-type fastening component is formed of the same material as surrounding material forming the article outside the fastening area, cut out a portion of the material of a size sufficient to provide the samples required by the steps below. To the extent possible without damage, remove any waist features or underlying materials or layers beneath the fastening area to reduce bulk created by layers. The remaining material will be the removed LOOPS material.
2. Lay the LOOPS material flat on a table, loops (fastening surface) side down. Determine the ordinary direction of pull by the associated hooks component on the Loops material when the article is in use. Using a permanent felt-tip marker (such as a SHARPIE) and a ruler, draw substantially straight arrows on the LOOPS material, indicating the ordinary direction of pull by the hooks on the LOOPS material, in several locations about the material.
   If the LOOPS material is taken from the fastening area of an outer cover 20 having a fastening area extending across both left and right sides, such as receiving element 31 exemplified by FIG. 2A, this direction will be perpendicular to and pointing away from the longitudinal axis of the outer cover: Using the marker and a ruler, draw a longitudinal (relative the outer cover) line through the center of the LOOPS material, and draw several arrows on the material substantially perpendicular to the line and pointing away from it, on either side of the line. (For illustrative example, see FIG. 15C, LOOPS material 22a, longitudinal line 22b, arrows 22c.)
   If the LOOPS material is taken from the inside portion of an outer cover where an insert is fastened, this direction will be parallel with the longitudinal axis of the outer cover and pointing toward the lateral axis of the outer cover.
3. Prepare double-side tape to join the LOOPS material to the fixture as follows: Join the adhesive side of 3M 1524 Transfer Adhesive to the adhesive side of a strip of 3M 9589 Double Coated Film Tape to form a double-sided tape laminate. (In the event either or both of these products are not available at the time of the test, equivalent product(s) sufficient to adhere the sample to the underlying surface and resist delamination in the test, as described below, may be substituted.)
4. Lay the prepared double-side tape flat on a table, with the 3M 1524 Transfer Adhesive side up. Remove the release backing to expose the adhesive of the 3M 1524 Transfer Adhesive. Gently lay the LOOPS material, loops side up, onto the exposed adhesive surface of the double-sided tape laminate. Apply substantially even pressure to the LOOPS material to press it against the adhesive surface, using a pressure of about 25 g/cm$^2$±10% (an appropriate weight having a flat bottom surface may be used). The LOOPS material should be applied to the tape evenly to avoid forming bubbles or wrinkles. If bubbles or wrinkles having a dimension of greater than about 3 mm in any direction are formed, do not use the portion(s) bearing bubbles or wrinkles in any samples for testing.
5. Cut substantially rectangular samples of the LOOPS material/tape laminate about 50 mm by at about 25 mm, with the shorter sides substantially parallel with the direction of the arrows. These will be the LOOPS Samples. (Note: The LOOPS Sample size may be adjusted in the event samples of the size specified above are unavailable. The size specified above is selected to provide some confidence that sufficient loops material is conveniently available to engage the entire area of a HOOKS Sample of the size specified below, but it will be appreciated that a margin of allowance has been provided for adjustment.)

Hook Material
1. Remove the hooks patch from the article without damaging the hooks patch. Use a freeze spray as necessary to weaken bonding by any adhesives; use a sharp, fine cutting instrument to sever any stitches, to facilitate separation of the hooks patch from the underlying layer. If it is not possible to remove the hooks patch from the underlying layer without damaging it, then simply cut around its outer edges to sever it from the remaining portions of the article. Lay the separated hooks patch ("HOOKS material") on a table, hooks facing down.
2. Prepare double-side tape to join the HOOKS material to the fixture as follows: Join the adhesive side of 3M 1524 Transfer Adhesive to the adhesive side of a strip of 3M 9589 Double Coated Film Tape to form a double-sided tape laminate. (In the event either or both of these products are not available at the time of the test, equivalent product(s) sufficient to adhere the sample to the underlying surface and resist delamination in the test, as described below, may be substituted.)
3. Lay the prepared double-side tape flat on a table, with the 3M 1524 Transfer Adhesive side up. Remove the release backing to expose the adhesive of the 3M 1524 Transfer Adhesive. Gently lay the HOOKS material, hooks side up, onto the exposed adhesive surface of the double-sided tape laminate. Apply substantially even pressure to the HOOKS material to press it against the adhesive surface, using a pressure of about 75 g/cm$^2$±10% (an appropriate weight having a flat bottom surface may be used). The HOOKS material should be applied to the tape evenly to avoid forming bubbles or wrinkles. If bubbles or wrinkles having a dimension of greater than about 3 mm in any direction are formed, do not use the portion(s) bearing bubbles or wrinkles in any samples for testing.
4. Cut one or more substantially rectangular samples (size of HOOKS material permitting) from the HOOKS material/tape laminate 13 mm by 25.4 mm, ±0.25 mm, with the shorter sides substantially parallel the direction of pull of the HOOKS material when in ordinary use. This will be HOOKS Samples.

(Note: A HOOKS Sample of the dimensions specified above will have an engagement area of 330 mm². If a HOOKS Sample of these dimensions and/or engagement area is not available on the article in question, obtain the largest sample available, and determine its area by measurement. Where values for Vertical Peak Load/Engagement Area and Vertical Load at 0.5 mm Vertical Displacement/Engagement Area are called for in the specification above, the values for Vertical Peak Load and Vertical Load at 0.5 mm Vertical Displacement are determined according to the test protocol below, and then divided by the HOOK Sample engagement area, to determine the Vertical Peak Load/Engagement Area and Vertical Load at 0.5 mm Vertical Displacement/Engagement Area.)

Samples of respective loops material and hooks material that have not been cut from finished manufactured wearable articles, but rather, taken from supplies of such materials prior to manufacture of articles, can be prepared in a manner similar to that set forth above. The materials should be oriented and cut according to the orientation and size in which they would appear in a finished product.

Test Equipment

A constant rate of extension tensile tester with computer interface (such as a MTS SYNERGIE 200 tensile tester, controlled with TestWorks 4 software, as available from MTS Systems Corp., Eden Prairie, Minn., or suitable equivalent), fitted with an appropriate load cell is used for this test. The load cell should be selected to be operated within 10% and 90% of its stated maximum load. The tensile tester is set up such that when the crosshead moves downward and compresses samples, a negative force reading is generated to indicate compression.

Figure 12A:
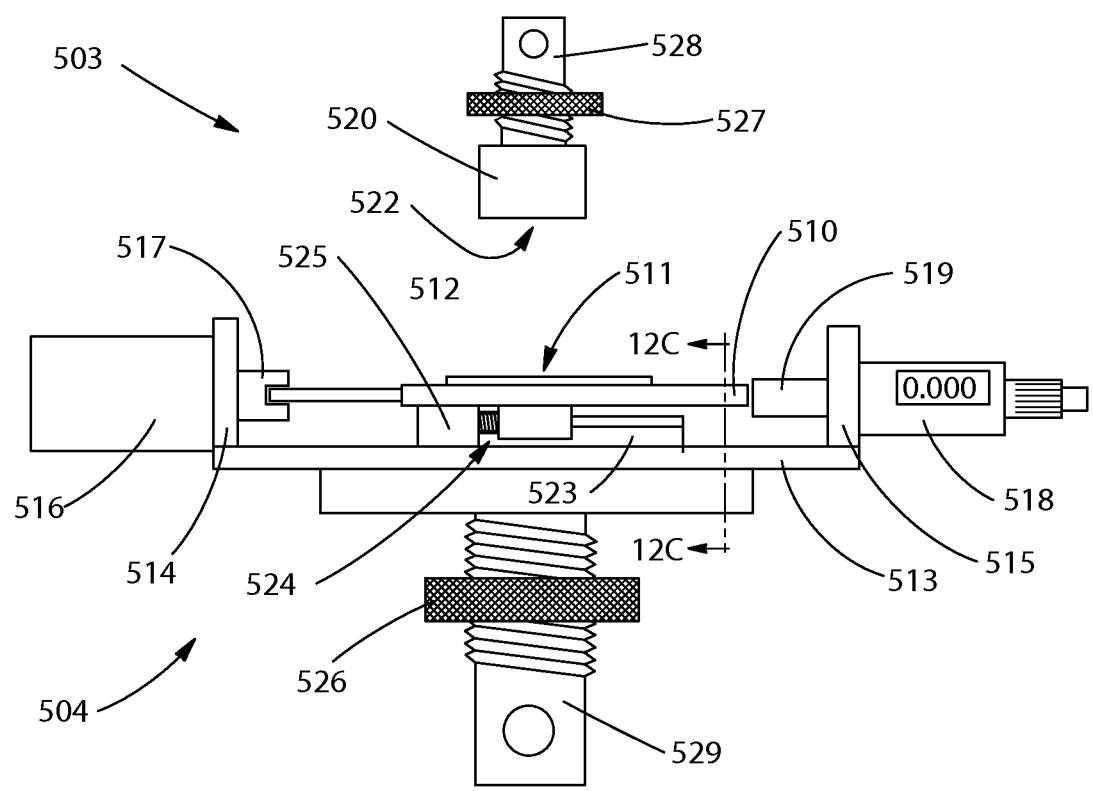
FIG. 12A is a schematic front-view depiction of upper and lower fixtures used in the Vertical Pull Test described herein.

For this test, two custom fixtures must be fabricated. Referring to FIG. 12A, the first fixture 503 includes a rectangular foot 520 that attaches to the load cell of the tester, and has a downward-facing planar surface 522 orthogonal to the path of travel of the crosshead, onto which a Hooks Sample is to be affixed. The second fixture 504 attaches to the bottom, stationary mount of the tensile tester, and consists of a base 513 and a solenoid-activated sliding plate 510 having an upward-facing planar surface 511 orthogonal to the path of travel of the crosshead, onto which the LOOPS Sample is to be affixed. Thus, when the test is performed, the loops side of the LOOPS Sample is oriented facing and parallel to, the hooks side of the Hooks Sample.

Still referring to FIG. 12A, the upper fixture 503 consists of a rectangular foot 520 affixed to a suitable mounting device such as an upper mounting shaft 528 adapted to mount to the load cell as affixed to the movable crosshead of the tensile tester. Upper mounting shaft 528 is threaded as shown, and has a locking collar 527. When upper mounting shaft 528 is connected to the mount of the load cell, locking collar 527 is turned against the mount, to immobilize fixture 503 such that the surface 522 remains orthogonal to the travel axis. The foot 520 is formed of aluminum with a downward-facing, planar, brushed-finish surface 522 orthogonal to the path of travel of the crosshead. Downward-facing surface 522 must be of sufficient length and width to accept the entirety of a Hooks Sample, shorter sides extending in a left-right direction, and must be substantially centered about the axis of upper mounting shaft 528.

Figure 12B:
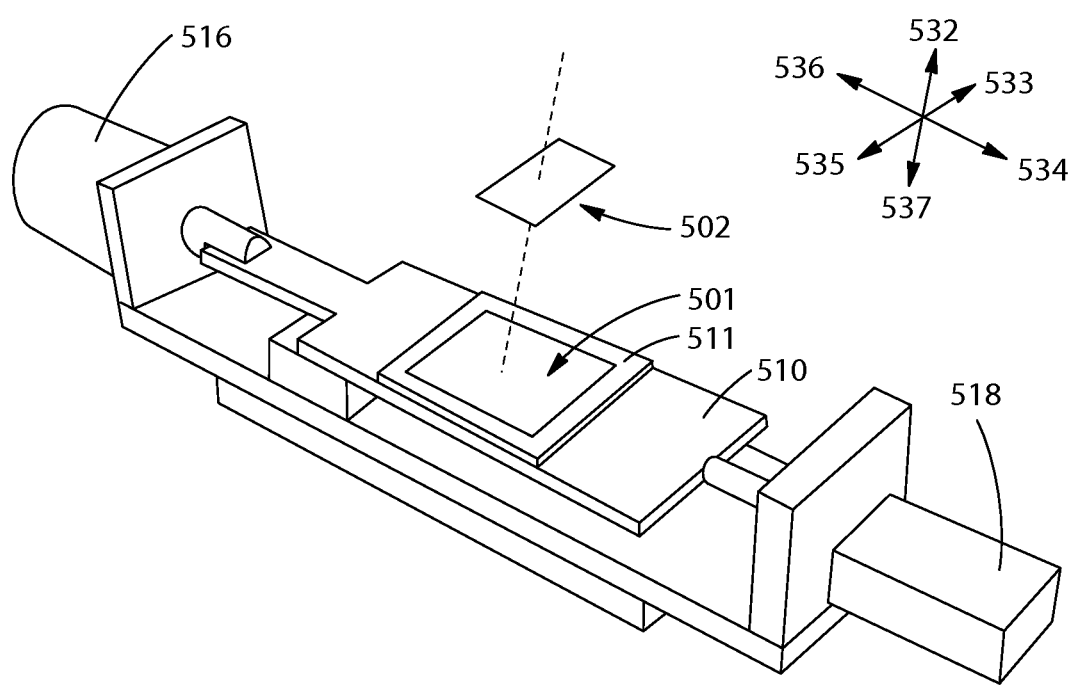
FIG. 12B is schematic perspective-view depiction of the lower fixture used in the Vertical Pull Test described herein, shown with test samples oriented with respect thereto.
Figure 12C:
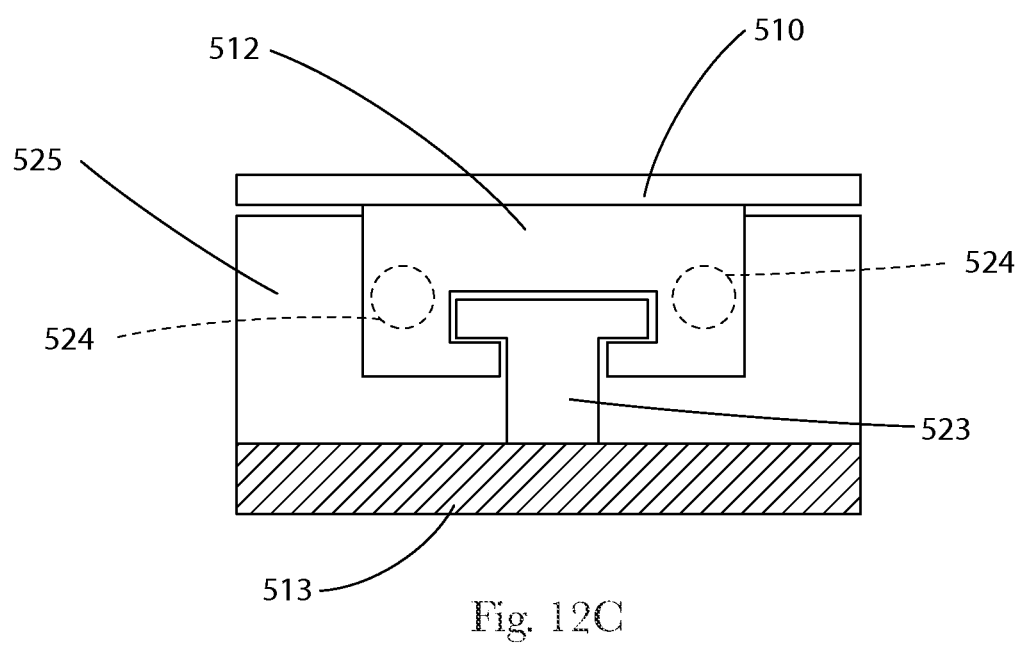
FIG. 12C is a view of cross-section 12C-12C taken through the schematic depiction of the lower fixture shown in FIG. 16A.

Referring to FIGS. 12A-12C, the lower fixture 504 consists of a base 513, having two vertical plates 514 and 515 affixed at each end. An electronic solenoid 516 (Sealed Linear Solenoid Actuator Extended Life—Sealed Pull type, Part No. 9719K112, McMaster Carr, Atlanta, Ga.—or suitable equivalent) is mounted on the left vertical plate 514, with its plunger 517 extending to the right and protruding through a hole in plate 514; the hole is large enough to permit free left-right movement of plunger 517. A micrometer 518 (Micrometer Head, Electronic type, 1" Max measuring range 0.00005" resolution, Part No. 74477589, MSC Industrial Supply, Melville N.Y.—or suitable equivalent) is mounted on the right vertical plate 515, with its spindle 519 extending to the left and protruding through a hole in plate 515; the hole is large enough to permit free left-right movement of the spindle 519. The solenoid plunger 517 and the micrometer spindle 519 are substantially coaxial. The base 513 is affixed to a suitable mounting device that includes lower mounting shaft 529, adapted to mount to the stationary mount of the tester. Lower mounting shaft 529 is threaded as shown, and has a locking collar 526. When lower mounting shaft 529 is mounted to the stationary mount of the tester, locking collar 526 is turned against the stationary mount to immobilize the base 513 relative the stationary mount of the tester, such that it will remain stationary with the stationary mount, so as to maintain surface 511 orthogonal to the path of travel of the crosshead during testing.

A horizontally sliding plate 510 has an integral tab as shown, connected to the solenoid plunger 517. Sliding plate 510 is affixed to plate guide 512, which has a horizontal, left-right track machined therein which mates with guide rail 523 to allow free left-right movement, with no significant vertical play. (Mating plate guide 512 and guide rail 523 are acquired from McMaster-Carr, Atlanta, Ga., Part No. 9880K3 (Frelon Plain-Bearing Guide Block); and Part No. 9880K13 (Frelon Plain-Bearing Rail).)

Guide rail 523 is affixed to base 513. As a consequence of this configuration, plate guide 512, and correspondingly, sliding plate 510, may move in a horizontal, left-right direction relative base 513, in response to activation of solenoid 516. Rightward movement of sliding plate 510 is limited by the distal end of micrometer spindle 519, which sliding plate 510 abuts in the rightwardmost position. Leftward movement of sliding plate 510 is limited by standoff 525, which plate guide 512 abuts in the leftwardmost position.

Guide rail 523 terminates at standoff 525, which also is affixed to base 513. Standoff 525 holds two recessed springs 524 that apply a sufficient force against the plate guide 512 to push the sample plate 510 to abutting relationship with the distal end of micrometer spindle 519 when solenoid 516 is not activated. Once activated, solenoid 516 pulls the sliding plate 510 toward the left, until plate guide 512 stops against standoff 525.

An aluminum sample plate having a planar, brushed-finish upward-facing surface 511 is affixed to the top surface of the sliding plate 510. Upward-facing surface 511 must be of sufficient length and width to accept the entirety of an LOOPS Sample, shorter side extending in a left-right direction, and must be substantially centered about the axis of lower mounting shaft 529.

The fixtures are configured such that when both upper fixture 503 and lower fixture 504 are installed on the tester, upper mounting shaft 528 and lower mounting shaft 529 are substantially coaxial, i.e., are aligned along the direction of pull of the crosshead. The fixtures are configured such that when HOOKS and LOOPS Samples are properly placed thereon and the fixtures are installed on the tester, the geometric centers of the shapes of the Samples are substantially aligned on a vertical axis when the Samples are engaged, prior to being offset by a Shear Displacement. The fixtures should be adapted such that, when installed on the tester, downward surface 522 on upper fixture 503 and upward surface 511 on lower fixture 504 are parallel to each other and orthogonal to the vertical line of travel of the crosshead.

Test Protocol

All testing is performed in a conditioned room maintained at about 23° C.±2 C.° and about 50%±2% relative humidity. Precondition the samples at about 23° C.±2 C.° and about 50%±2% relative humidity for 2 hours prior to testing.

The rectangular HOOKS Sample 502 and LOOPS Sample 501 are to be affixed onto the downward surface 522 and upward surface 511, respectively, with their respective directions of pull relative each other, when in use in an article, aligned along the left-right direction (in FIG. 12B, along direction 534-536), and in a relative rotational orientation within a horizontal plane corresponding with the directions of shearing force along which the materials would be pulled while in use on a finished article, relative the Shear Displacement effected by solenoid 516. Referring to FIGS. 12A and 12B, solenoid 516 will move the LOOPS Sample 501 to the left (direction 536 indicated in FIG. 12B) relative the Hooks Sample 502, for the selected Shear Displacement. In view of this, for the Hooks Sample 502 and LOOPS Sample 501 to be properly oriented relative each other on the fixtures, they should be placed thereon such that when engaged during the test in facing relationship they represent the manner in which the corresponding materials would be (a) oriented; and (b) urged by shearing force, relative each other when engaged on an article. In like fashion, any raw material samples are tested as they would be oriented on a finished article.

Remove the release backing on a LOOPS Sample. Gently place the LOOPS Sample on upward-facing surface 511, oriented as described above. After proper alignment, the LOOPS Sample should be affixed to surface 511 using a force of approximately 250 g, applied uniformly across the entire surface area of the sample, while surface 511 is oriented horizontally. Next, remove the release backing on a HOOKS Sample. Gently place the HOOKS Sample on downward-facing surface 522, oriented as described above. After proper alignment, the HOOKS Sample should be affixed to surface 522 using a force of approximately 250 g, applied uniformly across the entire surface area of the sample, while surface 522 is oriented horizontally, facing up.

Install the lower fixture 504 and upper fixture 503 onto the tensile tester. Set the gage length between surfaces 522 and 511 to 50 mm. Zero the load cell.

Activate the solenoid 516 to move the sliding plate 510 so that the plate guide 512 abuts the standoff 525. Adjust the micrometer 518 to extend the spindle 519 until it abuts the sliding plate 510. Zero the micrometer. Then, adjust the micrometer to retract the spindle 519 to the desired Shear Displacement (e.g., 1.00 mm, ±0.005 mm). Deactivate the solenoid 516 to allow the sliding plate 510 to move to the right so that it abuts the distal end of the micrometer spindle 519. (To assure calibration, the micrometer should be reset to the desired shear distance after every 20 samples.)

The tensile tester is programmed to move the crosshead down at 5.0 mm/sec until it moves 40 mm, and then further descend at a rate of 0.5 mm/sec, until 1.00 N of compressive force is applied to the Samples to engage them. After 3 seconds, the solenoid 516 is activated to move the sliding plate 510 to the left (Shear Displacement) position, and held for an additional 3 seconds. Next, set the crosshead to zero.

Start the tensile tester program to effect movement of the crosshead up 50 mm at 5 mm/sec and collect data. Plot the data as force (N) versus vertical crosshead displacement (mm).

Each LOOPS Sample and each HOOKS Sample may be used for only one test. During the test, confirm that neither of the samples partially delaminate from the surfaces 511, 522. If any delamination is detected, the result is invalid.

Following removal of a sample from a surface, clean the surface of any adhesive residue using appropriate solvent, and allow the surface to dry before affixing a new sample.

The following calculations are performed from the force/displacement curve:

1. Adjusted Crosshead Displacement ("ACD"): The positive displacement (mm) at which the force exceeds 0.0 N. If as a result of shearing the sample, the starting force exceeds 0.0 N, the adjusted crosshead displacement is taken as 0.00 mm. Reported to ±0.01 mm.
2. Vertical Peak Load: The maximum force (N) sustained by the sample pair, recorded between the ACD and 50 mm Vertical Displacement. Reported to ±0.01 N.
3. Displacement at Vertical Peak Load: The displacement (mm) from the ACD to the Vertical Peak Load. Reported to ±0.01 mm.
4. Greatest Vertical Load between 0.0 and 0.5 mm Vertical Displacement: The maximum force (N) sustained by the sample pair, recorded between the ACD and ACD+0.5 mm Vertical Displacement. Reported to ±0.1 N.
5. Greatest Vertical Load between 0.0 and 1.0 mm Vertical Displacement: The maximum force (N) sustained by the sample pair, recorded between ACD and ACD+1.0 mm Vertical Displacement. Reported to ±0.1 N.
6. Energy for Complete Removal: Energy (mJ), i.e., total area under the force/displacement curve, between ACD and 50 mm Vertical displacement. Report to ±0.1 mJ.
7. Energy to Resist Removal: Energy (mJ), i.e., total area under the force/displacement curve, between ACD and Vertical Displacement to Peak. Report to ±0.1 mJ.

For obtaining results for a selected loops and hooks combination for purposes herein, test a minimum of ten sample pairs (n=10) and report as an average.

The Vertical Pull Test may be used to compare the performance of any particular combination of loops material and hooks material with any other particular such fastening combination, and may be useful in determining which combination is more suitable for use in a particular application. Accordingly, the Vertical Pull Test may be used to select a fastening combination of loops material and hooks material suitable for use on a wearable article, such as, but not limited to, the article described herein.

Fastener Acoustic Test

Acoustic measurements on mechanical fastening systems were recorded as an engaged system undergoes a 90 degree tensile test. Recordings were made using 0.25 inch diaphragm, ultra-linear measurement microphone, such as the Earthworks M30 Ultra-linear microphone (Earthworks Inc., Milford, N.H.) with 16 bit preamplifier A/D D/A, capable of a minimum sampling rate of 44.1 kHz such as a PreSonus Firestudio Mobile Preamplifier, available from PreSonus Audio Electronics, Baton Rouge, La., or equivalent. +48 volt Phantom Power is supplied to the microphone by the preamplifier. SIA Smaart Acoustic Tools software package available from Rational Acoustics, Putnam, Conn. or equivalent is used to collect and process the acoustic recording. Calibration of the acoustic system is performed using a sound calibrator capable of 114 dB SPL sound @100 Hz, such as the Norsonic 1251 Sound Calibrator available from Scantech Inc., Columbia, Md. or equivalent.

Figure 13:
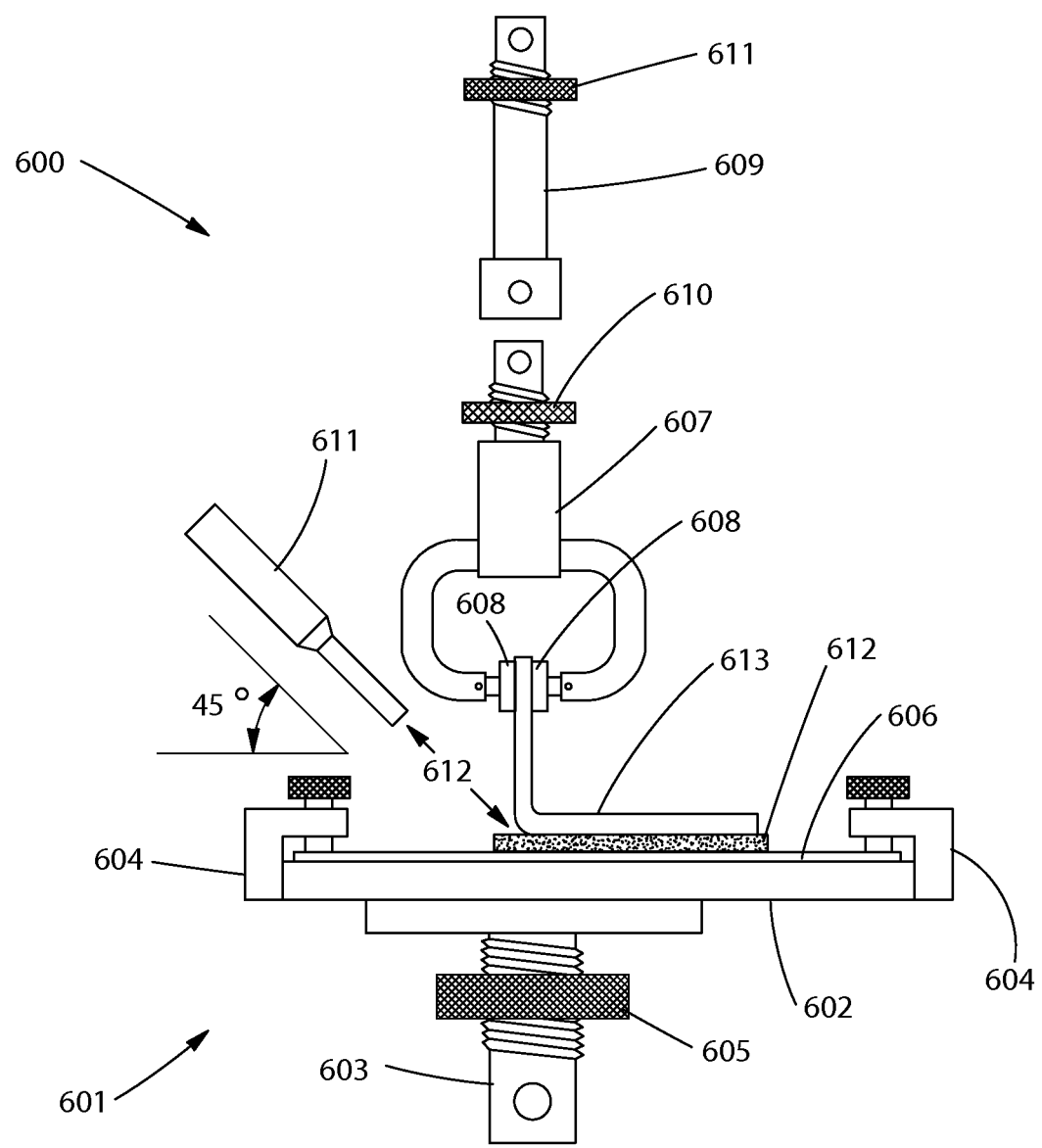
FIG. 13 is a view of a fixture and apparatus for measuring sound pressure levels generated by a fastening system upon disengagement.

The 90 degree peel force is measured using a constant rate of extension tensile tester with computer interface (a suitable instrument is a MTS Alliance under TestWorks 4 software, as available from MTS Systems Corp., Eden Prairie, Minn.) fitted with a appropriate load cell where the forces measured are between 10% and 90% of the cell's capacity. Referring to FIG. 13, the bottom fixture 601 consist of a 90° peel fixture consisting of a horizontally movable platform 602 mounted on a precision bearing assembly which allows for smooth left-right sliding action, and a mounting shaft 603 with locking collar 605 suitable for attaching to the non-movable base of the tensile tester. The movable platform 602, has clamps 604 that facilitate attaching a 5 cm (W) by 15 cm (L) by 2 mm (H) steel sample plate 606. A suitable 90° peel fixture is available from ChemInstruments, Inc., Fairfield, Ohio, Model No. TT-PF-90. When mounted properly the locking collar 605 is used to stabilize the bottom fixture 601 holding the movable platform 602 horizontally in the XY plane. The upper movable fixture is a pneumatic grip 607, fitted with rubber faced grips 608 wider than the width of the test specimen. A suitable grip set is the 10 N ADVANTAGE pneumatic grips available from MTS Systems Corp., Eden Prairie, Minn. Additionally an extension rod 609 of sufficient length is needed to allow clearance of the cross head above the acoustic isolation chamber. When assembled, locking collars 610 and 611 are used to stabilize the upper grip 607 and maintain alignment orthogonal to the movable platform 602. The tensile tester is programmed to move the crosshead up at a rate of 305 mm/min until the loops portion 613 completely separates from the hooks portion 612. Referring to FIG. 13, the microphone 611 is mounted at a 45° angle and a distance 612 of 50 mm±1 mm from the tip of the microphone to the base of the mounted sample.

The tensile tester fixtures shown in FIG. 13 are isolated from ambient noise. An isolation chamber 41 cm (W) by 61 cm (H) by 61 cm (D) made of 0.5 in. thick PVC walls is mounted on the tensile tester. The front of the chamber is hinged as a door. All sides are insulated with 2 in. thick Aurelex mineral fiber sound insulation available from Auralex Acoustics, Indianapolis, Ind. or equivalent. Two 80 mm diameter holes are cut into the top and bottom of the chamber to facilitate mounting of the top 600 and bottom 601 tensile fixtures.

Calibration of the Acoustic Equipment

The microphone is connected to the preamplifier using a high quality xlr cable. +48 volt Phantom Power is supplied to the microphone by the preamplifier. Attach the calibrator to the end of the microphone. Set the gain of the preamplifier to its lowest setting. Within the acoustic software select the microphone as input. Select a sampling rate of 44.1 kHz and 16 bits per second. Begin recording and collect data for 10 seconds. Apply a Fast Fourier Transform (FFT) processing with a size of 1 k, overlap of 50% and window set to Hanning Pick a slice from the frequency versus amplitude trace and display as 24 slices per octave. Record the amplitude at 1000 Hz. Repeat this procedure for each setting of the preamplifier gain until the gain setting generates a signal that clips.

Transfer the amplitude readings taken at 1000 Hz into Microsoft Excel, and plot amplitude versus gain settings and apply a least squares linear regression. This equation provides the constant offset to convert recorded amplitudes from dB FS (Full Scale Digital) to dB SPL (Sound Pressure Levels) as follows:

$$\Delta = 114 - (mx+b)$$

where
  m=slope from fitted regression
  x=gain setting
  b=intercept from fitted regression
  Δ=Delta value added to measured amplitude value (dB FS)

Sample Preparation

Precondition samples at 23° C.±2 C.° and 50%±2% relative humidity for 2 hours prior to testing. Identify the loops portion and the associated hooks portion on the surfaces of the article. Determine the ordinary direction of pull by the hooks portion on the loops material when the article is in use. Without damaging either piece, use scissors to cut the loops portion and hooks portion from the article. All layers attached underneath are left intact on the loops portion and hooks portion. Using a cyano-acrylate adhesive, mount the hooks portion specimen, hooks facing upward, onto a steel plate 606. The pull direction of the hooks portion should be parallel to the long edge of the steel plate 606. Place the loops portion, loops facing downward, on top of the hooks portion. Orientation is such that it coincides with the ordinary direction of pull by the hooks portion on the loops portion when the article is in use. Roll the loops portion and hooks portion 3 times with a 500 g roller. Attach the steel plate 606 to the movable platform via the clamps 604. Gentle lift the loops portion 613 and place into the pneumatic grips 607 and close. Align the specimen and test fixture such that the loops portion 613 in the upper grips hangs perpendicular to the test surface, and the specimen forms a 90 degree angle at the point of contact with the hooks portion 612. The vertical portion of the specimen should be taut but not exerting more than 0.05 N on the load cell. The original gage length can be adjusted as necessary to accommodate the length of the loops portion.

After the samples are loaded, zero the load cell and cross head position. Close the isolation chamber's door. Set the gain of the preamplifier to +30 dB. Within the acoustic software select the microphone as input. Select a sampling rate of 44.1 kHz and 16 bits per second. Begin recording and collecting of data and start the tensile software. The crosshead will ascend at 128 mm/min until separation of the loops portion and hooks portion is detected. Stop acoustic data collection. Three replicate loops portion/hooks portion combination harvested from identical articles are collected.

Data Analysis

Open the recorded wave file. Apply a fast Fourier transform (FFT) processing with a size of 1 k, overlap of 50% and window set to Hanning Average the intensity of amplitude as a function of frequency over the total time of the tensile pull. Plot the average amplitude (dB FS) versus frequency (Hz on a log narrow band scale).

Save the amplitude (dB FS) versus frequency (Hz) data to an ASCII file for import into Microsoft Excel. In Excel, add the Δ value at the specific recorded gain level to all amplitude values in order to convert from dB FS to calibrated dB SPL. After all three replicate peel data is imported, average the calibrated amplitudes from each peel measurement at each discrete frequency. Plot the average amplitude (dB SPL) verses frequency (Hz) from 20 to 20,000 Hz. Record the calibrated amplitude values at the closest frequency value to 500 Hz, 1,000 Hz and 2,000 Hz to the nearest 0.001 dB SPL.

Landing Zone Bending Stiffness Test

Landing zone bending stiffness is measured using a constant rate of extension tensile tester with computer interface (a suitable instrument is an MTS Alliance under TestWorks 4 software, as available from MTS Systems Corp., Eden Prairie, Minn.) fitted with a 10 N load cell. Referring again to FIGS. 8-11, a plunger blade 2100, shown in FIG. 9 (front view) and FIG. 10 (side view), is used for the upper movable test fixture. Base support platforms 2200, shown in FIG. 8, are used as the lower stationary test fixture. All testing is performed in a conditioned room maintained at about 23 C±2 C and about 50%±2% relative humidity. Herein, width and length of the test specimen are a lateral width and longitudinal length using the directional conventions corresponding to the outer cover sample from which the specimen is cut, as "lateral" and "longitudinal" are defined herein.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 3.25 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 25.00±0.02 mm between the two gap edges of the support platforms 2204, with the plunger blade 2103 accurately (±0.02 mm) centered in the gap. Program the tensile tester for a compression test. Set the gauge length from the bottom of the plunger blade 2103 to the top surface of the support platform 2204 to 15 mm.

Set the crosshead to lower at 500 mm/min for a distance of 25 mm. Set the data acquisition rate to 200 Hz.

Precondition outer cover samples at about 23 C±2 C and about 50%±2% relative humidity for 2 hours prior to testing.

To prepare a specimen for testing:
1. Lay a sample outer cover on a table, outer surface facing up. Identify the landing zone on the sample by the section(s) of loops material on the outside of the front waist region. Lay a straightedge oriented laterally and tangent to the lower extent (i.e., furthest from the waist edge toward the crotch region) of the section(s) of the loops material; if a seam(s) is (are) present joining the section(s) of loops material to adjacent material(s), the straightedge should be laid below the seam(s) such that the structure(s) of the seam(s) lie entirely above the straightedge. Using a sharp knife, cut along the straightedge and through all materials of the sample, so as to cleanly sever the portion of the front waist region bearing the landing zone from the rest of the sample outer cover.
2. Lay the straightedge across the severed portion, oriented laterally and tangent to the upper extent (i.e., closest the waist edge away from the crotch region) of the section(s) of the loops material; if a seam(s) is (are) present joining the section(s) of loops material to adjacent material(s), the straightedge should be laid above the seam(s) such that the structure(s) of the seam(s) lie below the straightedge. Using a sharp knife, cut along the straightedge and through all materials of the portion, so as to cleanly sever any materials in the front waist portion above the landing zone from the portion. (It will be understood that in some samples, the landing zone may extend entirely to the waist edge and there will be nothing to sever away in this step.) This step completes isolation of the specimen portion.
3. Remove any components (such as snap components, buttons or sections or patches of hooks or loops material, or other structures) disposed on the inside (wearer-facing) surfaces of the specimen for purposes of attaching an absorbent insert, in a manner that does not substantially damage the underlying materials (any further than they may have been damaged by installation of such components). This completes preparation of the specimen portion.
4. Measure the lateral width of the specimen (i.e., along the direction of lateral axis 45 in FIG. 14). Using a fine-tipped permanent marker, place marks on the inner/wearer-facing surface of specimen at 20% of the lateral width from the left end, the midpoint or 50% of the lateral width, and 20% of the lateral width from the right end. Place additional marks 10 mm laterally inward (toward the midpoint) from each end.

Lay the specimen flat onto the surface of the support platform 2204 over the gap 2209 with the inner/wearer facing surface facing up. The marks placed at 20% and 50% of the lateral width as described above mark the three bending stiffness measurement locations; for the bending stiffness measurement at each location, center the mark between the edges of the platforms 2204 that form the gap 2209, with the lateral width of the specimen oriented perpendicular the edges of the platforms 2204 that form the gap 2209 (i.e., longitudinal direction of the specimen is parallel to the edges of the platforms 2204 that form the gap 2209). Thus, when the specimen is properly located on the platforms, the bottom edge of the plunger blade 2103 will be aligned with the longitudinal direction of the specimen and with the selected mark, and the plunger blade will contact the specimen, form a longitudinal crease through the mark, and cause the specimen to bend about the longitudinal crease.

Zero the load cell; start the tensile tester and the data acquisition.

Program the software to calculate the maximum peak bending force (N) and Stiffness (N/m) from the constructed force (N) verses displacement (m) curve. Stiffness is calculated as the slope of the force/displacement curve for the linear region of the curve (see FIG. 11), using a minimum line segment of at least 25% of the total peak bending force to calculate the slope. Report peak bending force to the nearest 0.1 N and the landing zone bending stiffness to the nearest 0.1 N/m. Test five specimens and calculate average values for each bending stiffness measurement location.

Landing Zone Strain Test

The percent strain at 100 N is measured using a constant rate of extension tensile tester with computer interface (a suitable instrument is a MTS Alliance under TestWorks 4 software, as available from MTS Systems Corp., Eden Prairie, Minn.) fitted with a 250 N load cell. Both the movable (upper) and stationary (lower) pneumatic jaws are fitted with diamond faced grips (also available from MTS Systems Corp.) wider than the width of the test specimen. Perform all testing in a conditioned room maintained at about 23° C.±2 C.° and about 50%±2% relative humidity. Herein, width and length of the sample are a lateral width and longitudinal length as defined herein. Precondition samples at about 23° C.±2 C.° and about 50%±2% relative humidity for 2 hours prior to testing.

Test specimens are prepared in the manner described above in the Landing Zone Bending Stiffness Test, except that the marks placed at 20% and 50% of the lateral width are not required for the strain test.

Measure the lateral width of the specimen to the nearest 1 mm. Set the gage length between the grip faces to the lateral dimension minus 20 mm. Zero the crosshead position. Insert the specimen into the upper grips with the specimen's lateral direction aligned vertically within the upper and lower jaws. The top 10 mm (indicated by the 10 mm mark placed on the specimen) of the specimen is centered horizontally within the faces and the upper grips are closed. The portion of the specimen hanging freely down from the upper grips is inserted into the lower grips. Zero the load cell and close the lower grips. The specimen should be under enough tension to eliminate any slack, but less than 0.05 N of force on the load cell. Program the tensile tester to perform an extension test, collecting force verses extension data at an acquisition rate of 100 Hz as the crosshead raises at a rate of 100 mm/min until a force of 100 N is reached. Start the tensile test and data collection. Program the software to calculate the % Strain at 100 N:

% Strain=Extension at 100 N (mm)/original gage length (mm)×100

Repeat the test with 5 replicate specimens and calculate the average. Report the average as % Strain at 100 N to the nearest 0.1%.

An absorbent article having some or all of the features described herein may provide advantages over both conventional wholly reusable cloth diapers and conventional wholly disposable diapers. The potential for use of semi-durable materials, and more so durable materials, to form an outer cover, provides for an outer cover that may be used more than once, and, depending upon the materials selected, used and laundered many times. An outer cover having some or all of the features described herein may eliminate the necessity for a disposable outer cover structure, thereby reducing the volume of soiled waste the user must dispose of, as compared with typical disposable diapers. Additionally, because the possibility of a reusable outer cover that bears most of the structural loading generally imposed upon a disposable diaper is presented, disposable absorbent portions may have more simplified designs, reducing manufacturing and material costs as compared with those of disposable diapers. The possibility for making a disposable absorbent insert of non-traditional renewable materials (such as paper) is presented. At the same time, a disposable absorbent insert and outer cover having some or all of the features described herein may in many circumstances prevent most or all soiling of the outer cover by the wearer's exudates, thereby mitigating sanitation and odor problems associated with handling and storage, reducing the frequency of laundering necessary, and reducing the need for laundering resources, efforts and/or expenses, associated with conventional cloth diapers. A disposable absorbent insert having some or all of the features described herein also may provide better absorbency and better isolation of exudates from both the wearer's skin, and the wearer's clothing and environment, than conventional cloth diapers.

Use of durable materials for an outer cover also may provide other incidental benefits, in creating choices in use of materials for improved and/or more appealing comfort, fit, designs, colors, patterns, etc. as compared with disposable diapers. An outer cover having features described herein provides a wide variety of choices for making a wearable absorbent article look more attractive and/or more like an article of clothing or outerwear. In addition to the foregoing advantages, the use of an insert having an asymmetric structure together with orientation indicia allows for the design of an insert tailored to wearer anatomy and bodily functions as they differ front-to-rear, better performance, and increased economy in design, construction and use of materials, while enabling the user to ensure correct front-rear orientation of the insert within the outer cover. Other advantages are apparent from the description above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended that the appended claims cover all such changes and modifications, and that nothing in the foregoing description or the figures, but rather, only the appended claims, limit the scope of the invention.

What is claimed is:

1. A wearable two-piece absorbent article including an outer cover and a replaceable absorbent insert, wherein the outer cover comprises inner and outer surfaces, and comprises:
   a front waist region, a back waist region longitudinally opposite the front waist region, and a crotch region connecting the front and back waist regions;
   a landing zone disposed on a garment-facing surface of the front waist region and extending across substantially all of the front waist region, the landing zone comprising a loops material and having a perimeter;
   an insert fastener component disposed on the inner surface in the front waist region, the insert fastener component being secured directly to the loops material; and
   a stiffening member underlying at least a portion of the landing zone and extending across substantially all of the front waist region, wherein an outer layer of the front waist region consists essentially of the landing zone and the stiffening member, wherein the front waist region comprises an inner layer, and wherein the inner layer is joined to the outer layer only along the perimeter of the landing zone.

2. The article of claim 1 wherein the landing zone has a bending stiffness between about 60 and about 120 N/m.

3. The article of claim 1 comprising an unreinforced waistband along a longitudinally outboard edge of the front waist region.

4. The article of claim 3 wherein the unreinforced waistband extends along 50-90% of the longitudinally outboard edge of the front waist region, centered along a longitudinal centerline of the outer cover.

5. The article of claim 1 wherein the stiffening member is joined to the outer layer and the inner layer only along the perimeter of the landing zone.

6. The article of claim 1 wherein the stiffening member comprises a foam layer.

7. A wearable two-piece absorbent article including an outer cover and a replaceable absorbent insert, wherein the outer cover comprises an inner surface and an outer surface and comprises:
 a front waist region, a back waist region, and a crotch region connecting the front waist region and the back waist region;
 two fastener components disposed on a wearer-facing surface of the back waist region;
 a landing zone disposed on a garment-facing surface of the front waist region and extending laterally across substantially all of the front waist region, the landing zone comprising a loops material and having a perimeter;
 an insert fastener component disposed on the inner surface in the front waist region, the insert fastener component being secured directly to the loops material; and
 wherein the outer cover comprises an inner layer and an outer layer, wherein a stiffening member is disposed between the inner layer and the outer layer, and wherein the stiffening member is joined to the inner layer and the outer layer along the perimeter of the landing zone.

8. The article of claim 7 comprising a stiffening member disposed beneath the landing zone.

9. The article of claim 8 wherein the stiffening member is a foam layer.

10. The article of claim 8 wherein the stiffening member extends laterally across substantially all of the front waist region.

11. The article of claim 7 wherein the landing zone has a bending stiffness between about 60 and about 120 N/m or about 100 and about 300 N/m.

12. The article of claim 1 wherein the landing zone is laminated to the stiffening member.

* * * * *